US012584170B2

(12) United States Patent
Heron et al.

(10) Patent No.: US 12,584,170 B2

(45) Date of Patent: Mar. 24, 2026

(54) METHOD OF NANOPORE SEQUENCING OF CONCATENATED NUCLEIC ACIDS

(71) Applicant: Oxford Nanopore Technologies PLC, Oxford (GB)

(72) Inventors: Andrew John Heron, Oxford (GB); Daniel Ryan Garalde, Oxford (GB); James White, Oxford (GB)

(73) Assignee: Oxford Nanopore Technologies PLC, Oxford (GB)

(*) Notice: Subject to any disclaimer, the term of this patent is extended or adjusted under 35 U.S.C. 154(b) by 1224 days.

(21) Appl. No.: 17/379,931

(22) Filed: Jul. 19, 2021

(65) Prior Publication Data

US 2022/0090192 A1 Mar. 24, 2022

Related U.S. Application Data

(63) Continuation of application No. 16/304,101, filed as application No. PCT/GB2017/051493 on May 25, 2017, now Pat. No. 11,098,355.

(30) Foreign Application Priority Data

May 25, 2016 (GB) ..................................... 1609221

(51) Int. Cl.

| | |
|---|---|
| ***C12Q 1/6874*** | (2018.01) |
| ***C12N 15/10*** | (2006.01) |
| ***C40B 40/06*** | (2006.01) |

(52) U.S. Cl.

CPC ....... *C12Q 1/6874* (2013.01); *C12N 15/1093* (2013.01); *C12Q 2525/301* (2013.01); *C40B 40/06* (2013.01)

(58) Field of Classification Search

None

See application file for complete search history.

(56) References Cited

U.S. PATENT DOCUMENTS

| | | | |
|---|---|---|---|
| 6,465,193 | B2 | 10/2002 | Akeson et al. |
| 6,916,665 | B2 | 7/2005 | Bayley et al. |
| 7,947,454 | B2 | 5/2011 | Akeson et al. |
| 8,986,528 | B2 | 3/2015 | Denison et al. |
| 10,246,741 | B2 | 4/2019 | Clarke |
| 11,098,355 | B2 | 8/2021 | Heron et al. |
| 11,466,317 | B2 | 10/2022 | Clarke et al. |
| 11,789,014 | B2 | 10/2023 | Fordham |
| 11,920,193 | B2 | 3/2024 | Clarke et al. |
| 2002/0197618 | A1 | 12/2002 | Sampson |
| 2006/0003352 | A1 | 1/2006 | Lipkin et al. |
| 2012/0070818 | A1 | 3/2012 | Rowlen et al. |
| 2012/0115744 | A1 | 5/2012 | Raymond |
| 2013/0048499 | A1 | 2/2013 | Mayer et al. |
| 2013/0150253 | A1 | 6/2013 | Deciu et al. |
| 2014/0134618 | A1 | 5/2014 | Kokoris et al. |
| 2015/0024950 | A1 | 1/2015 | Bielas et al. |
| 2015/0152492 | A1 | 6/2015 | Brown et al. |
| 2015/0275289 | A1 | 10/2015 | Otwinowski et al. |
| 2015/0344945 | A1 | 12/2015 | Mandell et al. |
| 2016/0041179 | A1 | 2/2016 | Ju et al. |
| 2016/0237488 | A1 | 8/2016 | Ke et al. |
| 2016/0318016 | A1 | 11/2016 | Hou et al. |
| 2016/0326578 | A1 | 11/2016 | Bielas |
| 2017/0044605 | A1 | 2/2017 | Merriman et al. |
| 2017/0073734 | A1 | 3/2017 | Hancock et al. |
| 2018/0273933 | A1 | 9/2018 | Gunderson et al. |
| 2019/0284603 | A1 | 9/2019 | Shema-Yaacoby et al. |
| 2019/0352709 | A1 | 11/2019 | Clarke et al. |
| 2020/0010887 | A1 | 1/2020 | Heron et al. |
| 2021/0148903 | A1 | 5/2021 | Fordham |
| 2021/0363577 | A1 | 11/2021 | Clarke et al. |
| 2023/0084931 | A1 | 3/2023 | Clarke et al. |
| 2024/0060969 | A1 | 2/2024 | Fordham |

FOREIGN PATENT DOCUMENTS

| | | | |
|---|---|---|---|
| CN | 1860370 | A | 11/2006 |
| CN | 103695530 | A | 4/2014 |
| WO | WO 2000/028312 | A1 | 5/2000 |
| WO | WO 2000/034527 | A2 | 6/2000 |
| WO | WO 2001/042782 | A1 | 6/2001 |
| WO | WO 2002/028312 | A1 | 4/2002 |
| WO | WO 2005/124888 | A1 | 12/2005 |
| WO | WO 2006/100484 | A2 | 9/2006 |
| WO | WO 2008/102120 | A1 | 8/2008 |
| WO | WO 2008/102121 | A1 | 8/2008 |
| WO | WO 2009/035647 | A1 | 3/2009 |
| WO | WO 2009/077734 | A2 | 6/2009 |
| WO | WO 2010/004265 | A1 | 1/2010 |
| WO | WO 2010/004273 | A1 | 1/2010 |
| WO | WO 2010/055307 | A1 | 5/2010 |
| WO | WO 2010/086602 | A1 | 8/2010 |

(Continued)

OTHER PUBLICATIONS

International Search Report and Written Opinion for Application No. PCT/GB2017/051493, mailed Oct. 24, 2017.

International Preliminary Report on Patentability for Application No. PCT/GB2017/051493, mailed Dec. 6, 2018.

International Search Report and Written Opinion for Application No. PCT/GB2017/053603, mailed Apr. 6, 2018.

International Preliminary Report on Patentability for Application No. PCT/GB2017/053603, mailed Jun. 13, 2019.

International Search Report and Written Opinion for Application No. PCT/GB2019/051571, mailed Sep. 10, 2019.

(Continued)

*Primary Examiner* — Kaijiang Zhang

(74) *Attorney, Agent, or Firm* — Wolf, Greenfield & Sacks, P.C.

(57) ABSTRACT

The invention relates to a new method of characterising two or more target polynucleotides using a pore. The method involves sequentially attaching to a first polynucleotide one or more subsequent polynucleotides to form a concatenated polynucleotide.

18 Claims, 11 Drawing Sheets

Specification includes a Sequence Listing.

(56) References Cited

FOREIGN PATENT DOCUMENTS

| | | | |
|---|---|---|---|
| WO | WO 2010/086603 A1 | 8/2010 | |
| WO | WO 2010/086620 A1 | 8/2010 | |
| WO | WO 2011/067559 A1 | 6/2011 | |
| WO | WO 2012/003330 A2 | 1/2012 | |
| WO | WO 2012/042226 A2 | 4/2012 | |
| WO | WO 2012/107778 A2 | 8/2012 | |
| WO | WO 2012/164270 A1 | 12/2012 | |
| WO | WO 2013/014451 A1 | 1/2013 | |
| WO | WO 2013/041878 A1 | 3/2013 | |
| WO | WO 2013/057495 A2 | 4/2013 | |
| WO | WO 2013/098561 A1 | 7/2013 | |
| WO | WO 2013/098562 A2 | 7/2013 | |
| WO | WO 2013/109970 A1 | 7/2013 | |
| WO | WO 2013/153359 A1 | 10/2013 | |
| WO | WO 2013/185137 A1 | 12/2013 | |
| WO | WO-2013181170 A1 * | 12/2013 | ........... C12Q 1/6844 |
| WO | WO 2014/013259 A1 | 1/2014 | |
| WO | WO 2014/013260 A1 | 1/2014 | |
| WO | WO 2014/013262 A1 | 1/2014 | |
| WO | WO 2014/064443 A2 | 5/2014 | |
| WO | WO 2014/064444 A1 | 5/2014 | |
| WO | WO 2014/074922 A1 | 5/2014 | |
| WO | WO 2014/135838 A1 | 9/2014 | |
| WO | WO 2015/014035 A1 | 2/2015 | |
| WO | WO 2015/022544 A1 | 2/2015 | |
| WO | WO 2015/055981 A2 | 4/2015 | |
| WO | WO 2015/110777 A1 | 7/2015 | |
| WO | WO 2015/110813 A1 | 7/2015 | |
| WO | WO 2015/124935 A1 | 8/2015 | |
| WO | WO 2015/127387 A1 | 8/2015 | |
| WO | WO 2015/150786 A1 | 10/2015 | |
| WO | WO 2015/150787 A1 | 10/2015 | |
| WO | WO 2015/166275 A1 | 11/2015 | |
| WO | WO 2015/176034 A1 | 11/2015 | |
| WO | WO 2016/034591 A2 | 3/2016 | |
| WO | WO 2016/055777 A2 | 4/2016 | |
| WO | WO 2016/059363 A1 | 4/2016 | |
| WO | WO 2016/059375 A1 | 4/2016 | |
| WO | WO 2016/059427 A1 | 4/2016 | |
| WO | WO 2016/059436 A1 | 4/2016 | |
| WO | WO 2016/099673 A1 | 6/2016 | |
| WO | WO 2016/161402 A1 | 10/2016 | |
| WO | WO 2017/125565 A1 | 7/2017 | |
| WO | PCT/GB2017/051493 | 10/2017 | |
| WO | WO 2017/203269 A1 | 11/2017 | |
| WO | PCT/GB2017/053603 | 4/2018 | |
| WO | WO 2018/100370 A1 | 6/2018 | |
| WO | PCT/GB2019/051571 | 9/2019 | |

OTHER PUBLICATIONS

International Preliminary Report on Patentability for Application No. PCT/GB2019/051571, mailed Dec. 17, 2020.

Altschul et al., Basic local alignment search tool. J Mol Biol. Oct. 5, 1990;215(3):403-10.

Altschul, A protein alignment scoring system sensitive at all evolutionary distances. J Mol Evol. Mar. 1993;36(3):290-300.

Biswas et al., Click Addition of a DNA Thread to the N-Termini of Peptides for Their Translocation through Solid-State Nanopores. ACS Nano. Oct. 27, 2015;9(10):9652-64. doi: 10.1021/acsnano.5b04984. Epub Sep. 16, 2015.

Braha et al., Designed protein pores as components for biosensors. Chem Biol. Jul. 1997;4(7):497-505.

Case 1:17-cv-00275-LPS Document 18. Notice of subsequent events relating to Oxford's motion to dismiss (D.I. 9). Oct. 18, 2017.

Case 1:17-cv-00275-LPS Document 19. Oxford Nanopore Technologies, Inc.'s response to Pacific Biosciences of California, Inc.'s notice of subsequent events. Oct. 24, 2017.

Case 1:17-cv-00275-RGA Document 10. Oxford's opening brief in support of its motion to dismiss PacBio's complaint for patent infringement. May 8, 2017.

Case 1:17-cv-00275-RGA Document 14. PacBio's response to Oxford's motion to dismiss. Jun. 5, 2017.

Case 1:17-cv-00275-RGA Document 16. Oxford's reply brief in support of its motion to dismiss PacBio's complaint for patent infringement. Jun. 26, 2017.

Case 1:17-cv-01353-LPS Document 13. First Amended Complaint for Patent Infringement. Nov. 30, 2017.

Case 1:17-cv-01353-LPS Document 15. Plaintiff's response to Oxford Nanopore Techologies, Inc.'s Motion to Dismiss and Request for Scheduling Conference. Nov. 30, 2017.

Case 1:17-cv-01353-RGA Document 10. Oxford's opening brief in support of its motion to partially dismiss Pacbio's complaint for patent infringement. Nov. 16, 2017.

Chandler et al., A new microparticle size calibration standard for use in measuring smaller microparticles using a new flow cytometer. J Thromb Haemost. Jun. 2011;9(6):1216-24. doi: 10.1111/j.1538-7836.2011.04283.x.

Chen et al., High spatial resolution nanoslit SERS for single-molecule nucleobase sensing. Nat Commun. Apr. 30, 2018;9(1):1733. doi: 10.1038/s41467-018-04118-7.

Colas et al., Microscopical investigations of nisin-loaded nanoliposomes prepared by Mozafari method and their bacterial targeting. Micron. 2007;38(8):841-7.

Devereux et al., A comprehensive set of sequence analysis programs for the VAX. Nucleic Acids Res. Jan. 11, 1984;12(1 Pt 1):387-95.

Eliseev et al., Molecular Recognition of Nucleotides, Nucleosides, and Sugars by Aminocyclodextrins. J. Am. Chem. Soc., 1994;116:6081-6088.

Feng et al., Nanopore-based fourth-generation DNA sequencing technology. Genomics Proteomics Bioinformatics. Feb. 2015;13(1):4-16. doi: 10.1016/j.gpb.2015.01.009. Epub Mar. 2, 2015. Erratum in: Genomics Proteomics Bioinformatics. Dec. 2015;13(6):383. Erratum in: Genomics Proteomics Bioinformatics. Jun. 2015;13(3):200-201. Erratum in: Genomics Proteomics Bioinformatics. Dec. 2015;13(6):383.

Gonzalez-Perez et al., Biomimetic triblock copolymer membrane arrays: a stable template for functional membrane proteins. Langmuir. Sep. 15, 2009;25(18):10447-50. doi: 10.1021/la902417m.

Grant et al., A facile method for attaching nitroxide spin labels at the 5' terminus of nucleic acids. Nucleic Acids Res. 2007;35(10):e77. Epub May 21, 2007.

Heron et al., Simultaneous measurement of ionic current and fluorescence from single protein pores. J Am Chem Soc. Feb. 11, 2009;131(5):1652-3. doi: 10.1021/ja808128s.

Holden et al., Direct introduction of single protein channels and pores into lipid bilayers. J Am Chem Soc. May 11, 2005;127(18):6502-3.

Holden et al., Functional bionetworks from nanoliter water droplets. J Am Chem Soc. Jul. 11, 2007;129(27):8650-5. Epub Jun. 16, 2007.

Hornblower et al., Single-molecule analysis of DNA-protein complexes using nanopores. Nat Methods. Apr. 2007;4(4):315-7. Epub Mar. 4, 2007.

Howorka et al., A Protein Pore with a Single Polymer Chain Tethered within the Lumen. J. Am. Chem. Soc. Feb. 29, 2000;122(11): 2411-2416. https://doi.org/10.1021/ja993221h.

Howorka et al., Probing distance and electrical potential within a protein pore with tethered DNA. Biophys J. Dec. 2002;83(6):3202-10.

Howorka et al., Sequence-specific detection of individual DNA strands using engineered nanopores. Nat Biotechnol. Jul. 2001;19(7):636-9.

Ivanov et al., DNA tunneling detector embedded in a nanopore. Nano Lett. Jan. 12, 2011;11(1):279-85. doi: 10.1021/nl103873a. Epub Dec. 6, 2010.

Kocalka et al., Rapid and efficient DNA strand cross-linking by click chemistry. Chembiochem. May 23, 2008;9(8):1280-5. doi:10.1002/cbic.200800006.

Kolb et al., Click Chemistry: Diverse Chemical Function from a Few Good Reactions. Angew Chem Int Ed Engl. Jun. 1, 2001;40(11):2004-2021.

Kozarewa et al., 96-plex molecular barcoding for the Illumina Genome Analyzer. Methods Mol Biol. 2011;733:279-98. doi: 10.1007/978-1-61779-089-8_20.

(56) References Cited

OTHER PUBLICATIONS

Kumar et al., Nonradioactive labeling of synthetic oligonucleotide probes with terminal deoxynucleotidyl transferase. Anal Biochem. Mar. 1988;169(2):376-82. Erratum in: Anal Biochem Sep. 1988;173(2):469.
Langecker et al., Synthetic lipid membrane channels formed by designed DNA nanostructures. Science. Nov. 16, 2012;338(6109):932-6. doi: 10.1126/science.1225624.
Lieberman et al., Processive replication of single DNA molecules in a nanopore catalyzed by phi29 DNA polymerase. J Am Chem Soc. Dec. 22, 2010;132(50):17961-72. doi:10.1021/ja1087612. Epub Dec. 1, 2010.
Liu et al., Adding new chemistries to the genetic code. Annu Rev Biochem. 2010;79:413-44. doi: 10.1146/annurev.biochem.052308.105824.
Montal et al., Formation of bimolecular membranes from lipid monolayers and a study of their electrical properties. Proc Natl Acad Sci U S A. Dec. 1972;69(12):3561-6.
Nikolov et al., Behavior of giant vesicles with anchored DNA molecules. Biophys J. Jun. 15, 2007;92(12):4356-68. Epub Mar. 23, 2007.
Pfeiffer et al., Bivalent cholesterol-based coupling of oligonucleotides to lipid membrane assemblies. J Am Chem Soc. Aug. 25, 2004;126(33):10224-5.
Smith et al., Capture, Unfolding, and Detection of Individual tRNA Molecules Using a Nanopore Device. Front Bioeng Biotechnol. Jun. 24, 2015;3:91. doi: 10.3389/fbioe.2015.00091.
Soni et al., Synchronous optical and electrical detection of biomolecules traversing through solid-state nanopores. Rev Sci Instrum. Jan. 2010;81(1):014301. doi: 10.1063/1.3277116. 7 pages.
Stoddart et al., Single-nucleotide discrimination in immobilized DNA oligonucleotides with a biological nanopore. Proc Natl Acad Sci U S A. May 12, 2009;106(19):7702-7. doi: 10.1073/pnas.0901054106. Epub Apr. 20, 2009.
Stranges et al., Design and characterization of a nanopore-coupled polymerase for single-molecule DNA sequencing by synthesis on an electrode array. Proc Natl Acad Sci U S A. Nov. 1, 2016;113(44):E6749-E6756. doi: 10.1073/pnas.1608271113. Epub Oct. 11, 2016.
Troutt et al., Ligation-anchored PCR: a simple amplification technique with single-sided specificity. Proc Natl Acad Sci U S A. Oct. 15, 1992;89(20):9823-5. Erratum in: Proc Natl Acad Sci U S A Apr. 15, 1993;90(8):3775.
United States District Court for the District of Delaware Order. *Pacific Biosciences of California, Inc.* v. *Oxford Nanopore Technolgoies, Inc.* Civil Action No. 17-275-RGA. Nov. 9, 2017.
Van Lengerich et al., Covalent attachment of lipid vesicles to a fluid-supported bilayer allows observation of DNA-mediated vesicle interactions. Langmuir. Jun. 1, 2010;26(11):8666-72. doi: 10.1021/la904822f.
Wendell et al., Translocation of double-stranded DNA through membrane-adapted phi29 motor protein nanopores. Nat Nanotechnol. Nov. 2009;4(11):765-72. doi: 10.1038/nnano.2009.259. Epub Sep. 27, 2009. Author Manuscript.
Yoshina-Ishii et al., Arrays of mobile tethered vesicles on supported lipid bilayers. J Am Chem Soc. Apr. 2, 2003;125(13):3696-7.
Yusko et al., Controlling the translocation of proteins through nanopores with bioinspired fluid walls. Nat Nanotechnol. Nat Nanotechnol. Apr. 2011; 6(4): 253-260. EPub Feb. 20, 2011. doi: 10.1038/nnano.2011.12 Author manuscript; available in PMC Oct. 1, 2011.
International Search Report and Written Opinion for Application No. PCT/GB2018/051190, mailed Jul. 26, 2018.
International Preliminary Report on Patentability for Application No. PCT/GB2018/051190, mailed Nov. 14, 2019.
Anderson, The clinical plasma proteome: a survey of clinical assays for proteins in plasma and serum. Clin Chem. Feb. 2010;56(2):177-85. doi: 10.1373/clinchem.2009.126706. Epub Nov. 2, 2009.
Chan et al., Recent advances and method development for drug target identification. Trends Pharmacol Sci. Feb. 2010;31(2):82-8. doi: 10.1016/j.tips.2009.11.002. Epub Dec. 7, 2009.
Edwards et al., The role of proteomics in clinical cardiovascular biomarker discovery. Mol Cell Proteomics. Oct. 2008;7(10):1824-37. doi: 10.1074/mcp.R800007-MCP200. Epub Jul. 30, 2008.
Hu et al., Detection and analysis of DNA recapture through a solid-state nanopore. Chinese science bulletin. Dec. 2014;59(35):4953-9.
Jacquet et al., Identification of cardiac myosin-binding protein C as a candidate biomarker of myocardial infarction by proteomics analysis. Mol Cell Proteomics. Dec. 2009;8(12):2687-99. doi: 10.1074/mcp.M900176-MCP200. Epub Aug. 31, 2009.
Jiang et al., miR2Disease: a manually curated database for microRNA deregulation in human disease. Nucleic Acids Res. Jan. 2009;37(Database issue):D98-104. doi: 10.1093/nar/gkn714. Epub Oct. 15, 2008.
Köhler et al., Continuous cultures of fused cells secreting antibody of predefined specificity. Nature. Aug. 7, 1975;256(5517):495-7. doi: 10.1038/256495a0.
Li et al., Structural elucidation of post-translational modifications in monoclonal antibodies. State-of-the-art and emerging technologies for therapeutic monoclonal antibody characterization vol. 2. Biopharmaceutical characterization: ACS Symposium Series; American Chemical Society. 2015. Chapter 3 (pp. 119-183).
Maddox et al., Elevated serum levels in human pregnancy of a molecule immunochemically similar to eosinophil granule major basic protein. J Exp Med. Oct. 1, 1983;158(4):1211-26. doi: 10.1084/jem.158.4.1211.
Patz et al., Panel of serum biomarkers for the diagnosis of lung cancer. J Clin Oncol. Dec. 10, 2007;25(35):5578-83. doi: 10.1200/JCO.2007.13.5392.
Peng et al., Reverse DNA translocation through a solid-state nanopore by magnetic tweezers. Nanotechnology. May 6, 2009;20(18):185101. doi: 10.1088/0957-4484/20/18/185101. Epub Apr. 14, 2009.
Ylera et al., Off-rate screening for selection of high-affinity anti-drug antibodies. Anal Biochem. Oct. 15, 2013;441(2):208-13. doi: 10.1016/j.ab.2013.07.025. Epub Jul. 29, 2013.

* cited by examiner

3

METHOD OF NANOPORE SEQUENCING OF CONCATENATED NUCLEIC ACIDS

Related Applications

This Application is a continuation of U.S. application Ser. No. 16/304,101, filed Nov. 21, 2018, which is a national stage filing under 35 U.S.C. § 371 of international application number PCT/GB2017/051493, filed May 25, 2017, and claims the benefit of GB application number 1609221.5, filed May 25, 2016, each of which is herein incorporated by reference in its entirety.

FIELD OF THE INVENTION

The invention relates to a new method of characterising two or more target polynucleotides using a pore.

BACKGROUND OF THE INVENTION

There is currently a need for rapid and cheap polynucleotide (e.g. DNA or RNA) sequencing and identification technologies across a wide range of applications. Existing technologies are slow and expensive mainly because they rely on amplification techniques to produce large volumes of polynucleotide and require a high quantity of specialist fluorescent chemicals for signal detection.

Transmembrane pores (nanopores) have great potential as direct, electrical biosensors for polymers and a variety of small molecules. In particular, recent focus has been given to nanopores as a potential DNA sequencing technology.

When a potential is applied across a nanopore, there is a change in the current flow when an analyte, such as a nucleotide, resides transiently in the barrel for a certain period of time. Nanopore detection of the nucleotide gives a current change of known signature and duration. In the strand sequencing method, a single polynucleotide strand is passed through the pore and the identities of the nucleotides are derived. Strand sequencing can involve the use of a molecular brake to control the movement of the polynucleotide through the pore.

SUMMARY OF THE INVENTION

The inventors have surprisingly demonstrated that it is possible to improve the efficiency of transmembrane pore-based characterisation of two or more target polynucleotides by sequentially attaching the target polynucleotides together to form a concatenated polynucleotide. If the binding of a second target polynucleotide to a first polynucleotide occurs selectively in the sense that binding only occurs as the first target polynucleotide moves through the pore, the time taken for the second target polynucleotide to contact the pore is reduced and binding of the target polynucleotides present in a sample in the absence of the pore is avoided. Concatenation of the target polynucleotides is only achieved when a first target polynucleotide moves through a pore. This is important because concatenation of the target polynucleotides in solution would result in a reduction of the number of free ends that could be captured by a pore.

Accordingly, the invention provides a method of characterising two or more target polynucleotides. The method involves sequentially attaching to a first polynucleotide one or more subsequent polynucleotides to form a concatenated polynucleotide. The method comprises:

(a) contacting a first target polynucleotide with a transmembrane pore in a membrane such that the first target polynucleotide moves through the pore;

(b) sequentially attaching to the first target polynucleotide one or more subsequent target polynucleotides to provide a concatenated polynucleotide within which the target polynucleotides move through the pore in attachment order, wherein a subsequent target polynucleotide is selectively attached to the preceding target polynucleotide in the attachment order when the preceding target polynucleotide moves through the pore; and (c) taking one or more measurements which are indicative of one or more characteristics of the concatenated polynucleotide as it moves with respect to the pore.

Also provided is a population of two or more polynucleotide Y adaptors for characterising two or more double stranded target polynucleotides, wherein each adaptor comprises first and second parts which are capable of hybridising together and wherein each first part is initially protected from hybridisation to the second part.

In addition, a kit for characterising two or more double stranded target polynucleotides comprising a population of Y adaptors of the invention and a population of hairpin loops is provided.

Figure 1:
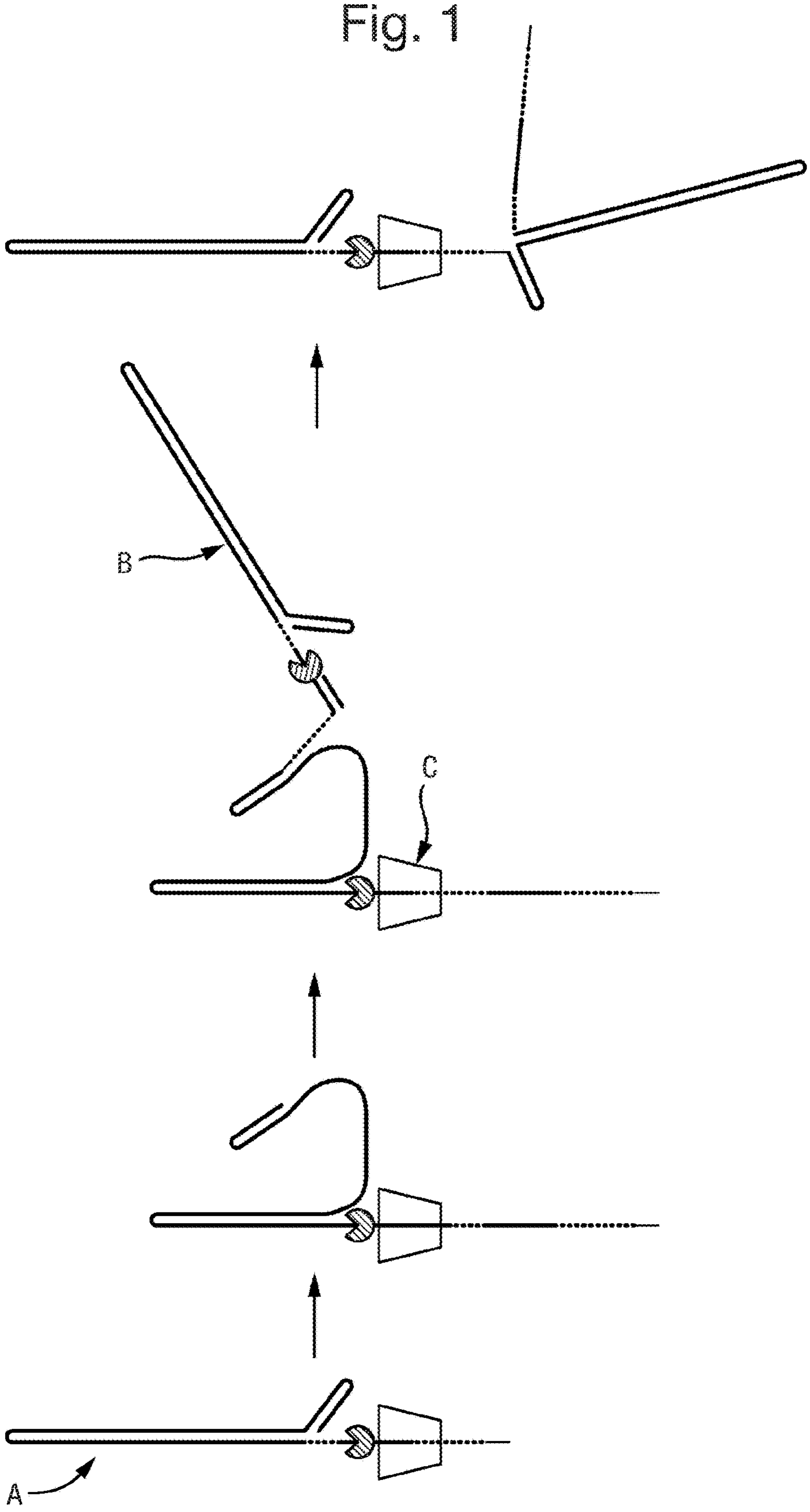
FIG. 1 shows the attachment of a subsequent target polynucleotide (labelled B) to the first target polynucleotide (labelled A) to produce a concatenated polynucleotide. The attachment point in the first target polynucleotide was revealed for attachment as the first polynucleotide moved through the pore (labelled C).
Figure 2:
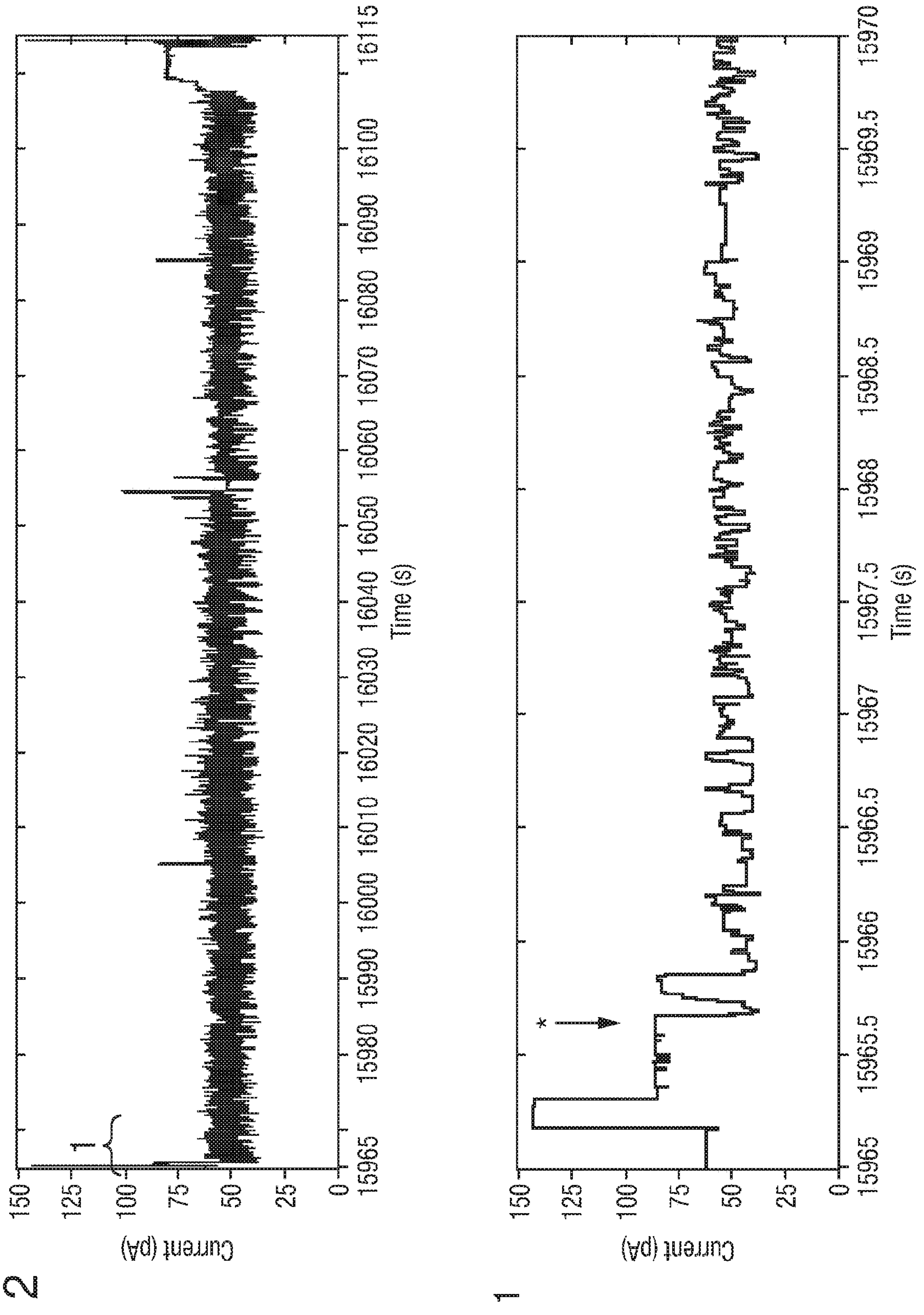
FIG. 2 shows example current traces (y-axis label=Current (pA), x-axis label=Time (s) for both traces) of when a helicase T4 Dda-(E94C/F98W/C109A/C136A/A360C) (SEQ ID NO: 24 with mutations E94C/F98W/C109A/C136A/A360C and then (ΔM1)G1G2 (where (ΔM1)G1G2=deletion of M1 and then addition G1 and G2)) controlled the translocation of the concatenated polynucleotide through an MspA nanopore. The top trace shows the controlled translocation of the concatenated polynucleotide and the lower trace labelled 1 shows zoomed in region 1 of the top trace.
Figure 3:
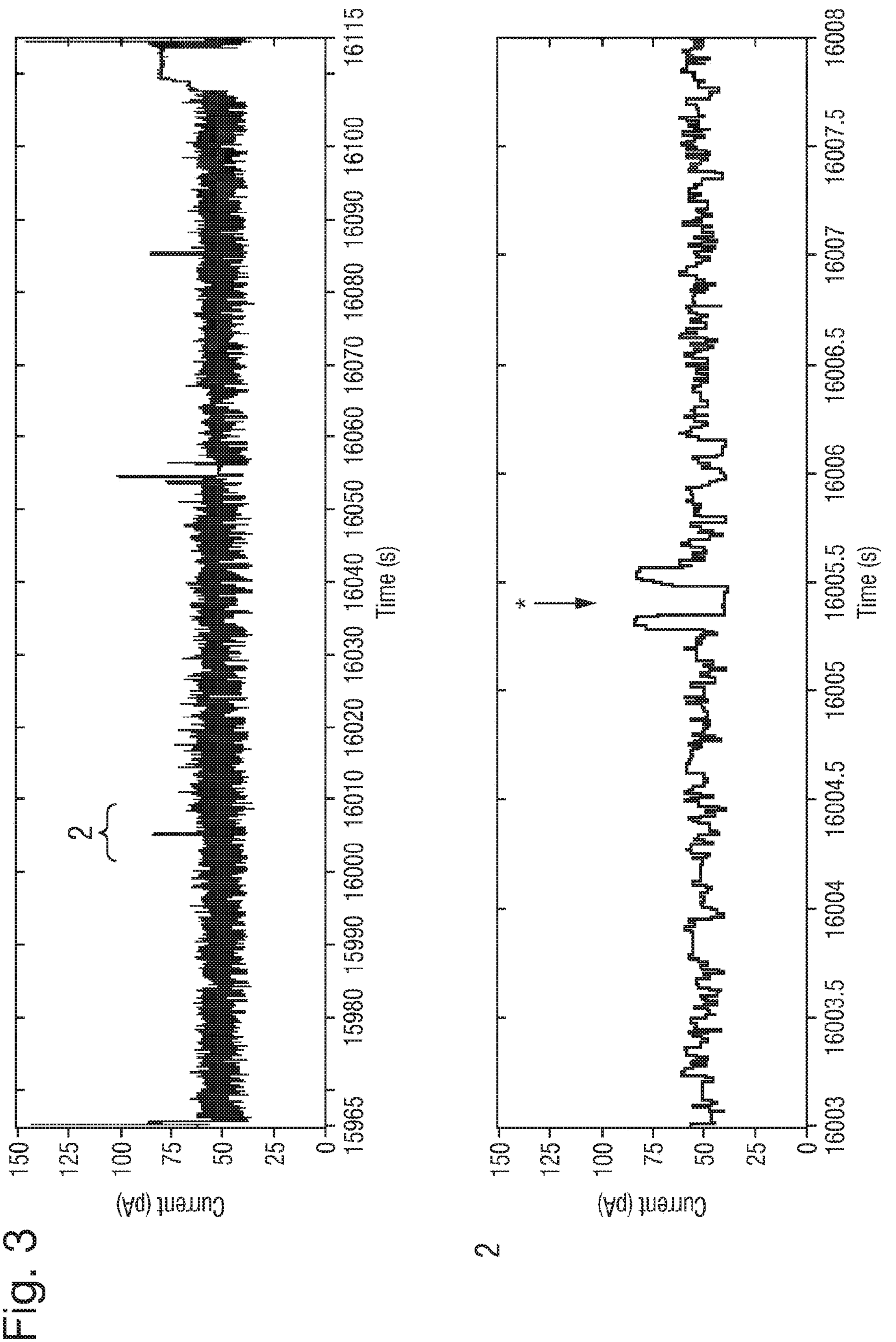
FIG. 3 shows example current traces (y-axis label=Current (pA), x-axis label=Time (s) for both traces) of when a helicase T4 Dda-(E94C/F98W/C109A/C136A/A360C) controlled the translocation of the concatenated polynucleotide through an MspA nanopore. The top trace shows the controlled translocation of the concatenated polynucleotide and the lower trace labelled 2 shows zoomed in region 2 of the top trace.
Figure 4:
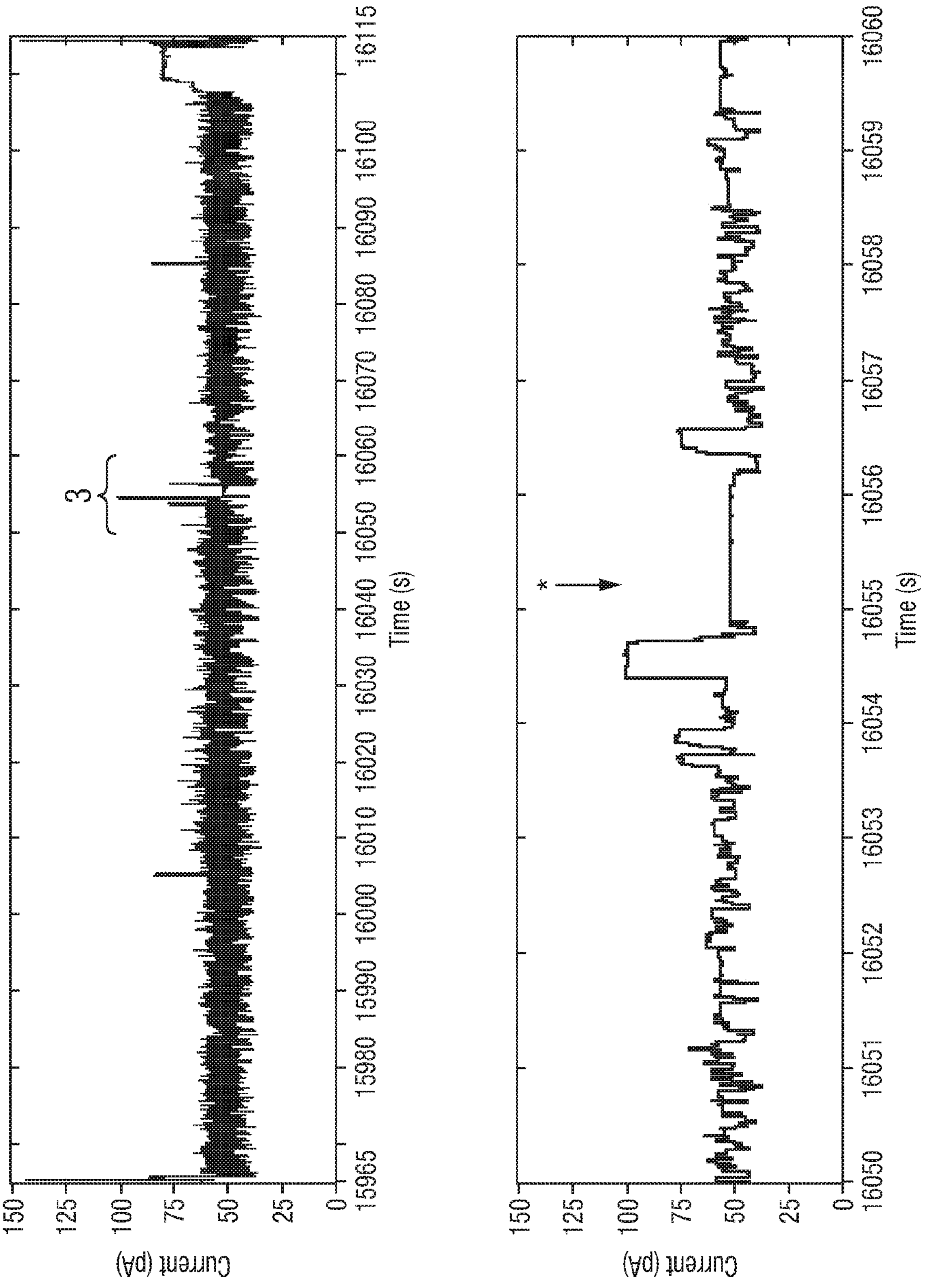
FIG. 4 shows example current traces (y-axis label=Current (pA), x-axis label=Time (s) for both traces) of when a helicase T4 Dda-(E94C/F98W/C109A/C136A/A360C) controlled the translocation of the concatenated polynucleotide through an MspA nanopore. The top trace shows the controlled translocation of the concatenated polynucleotide and the lower trace labelled 3 shows zoomed in region 3 of the top trace.
Figure 5:
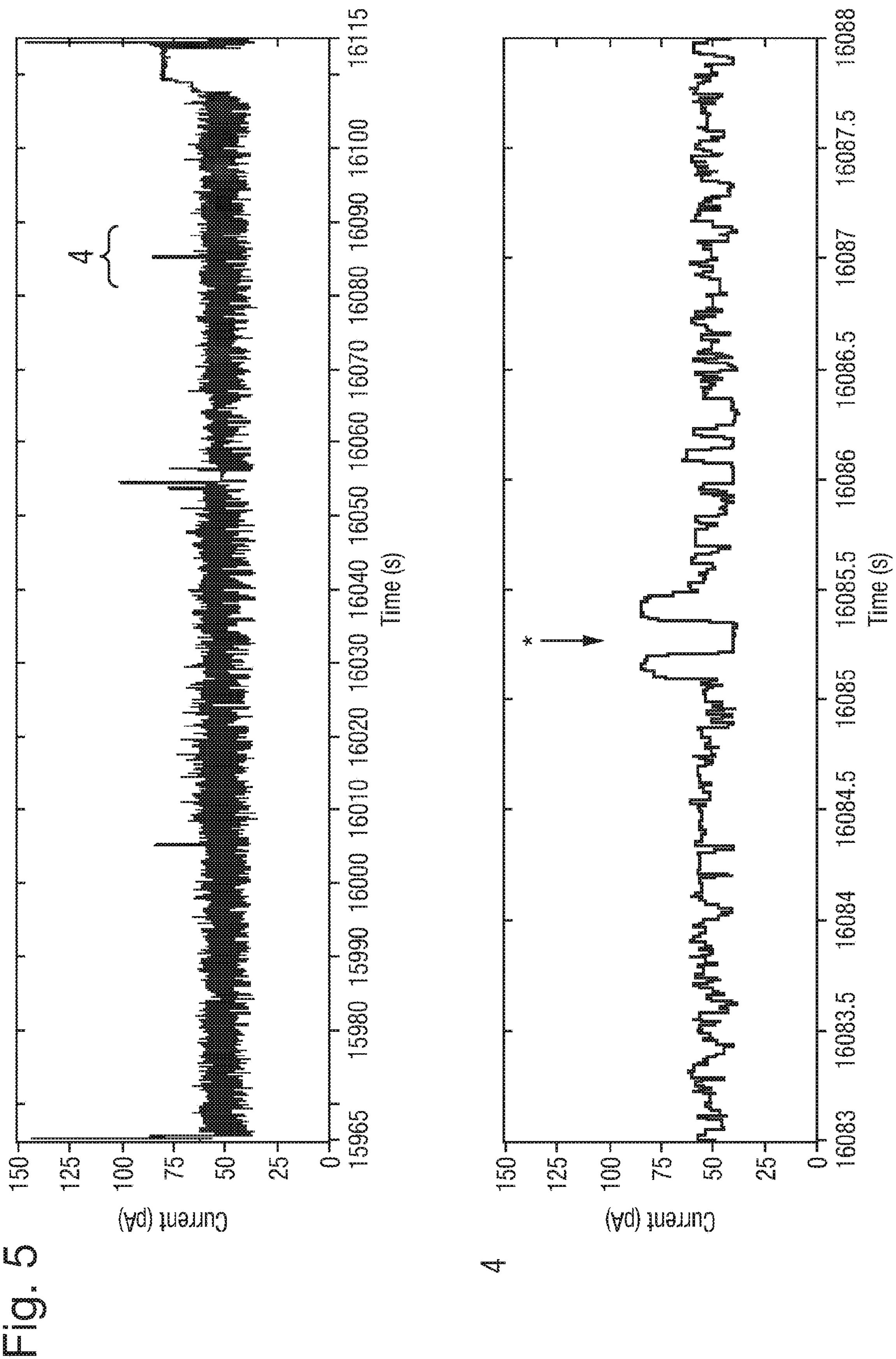
FIG. 5 shows example current traces (y-axis label=Current (pA), x-axis label=Time (s) for both traces) of when a helicase T4 Dda-(E94C/F98W/C109A/C136A/A360C) controlled the translocation of the concatenated polynucleotide through an MspA nanopore. The top trace shows the controlled translocation of the concatenated polynucleotide and the lower trace labelled 4 shows zoomed in region 4 of the top trace.
Figure 6:
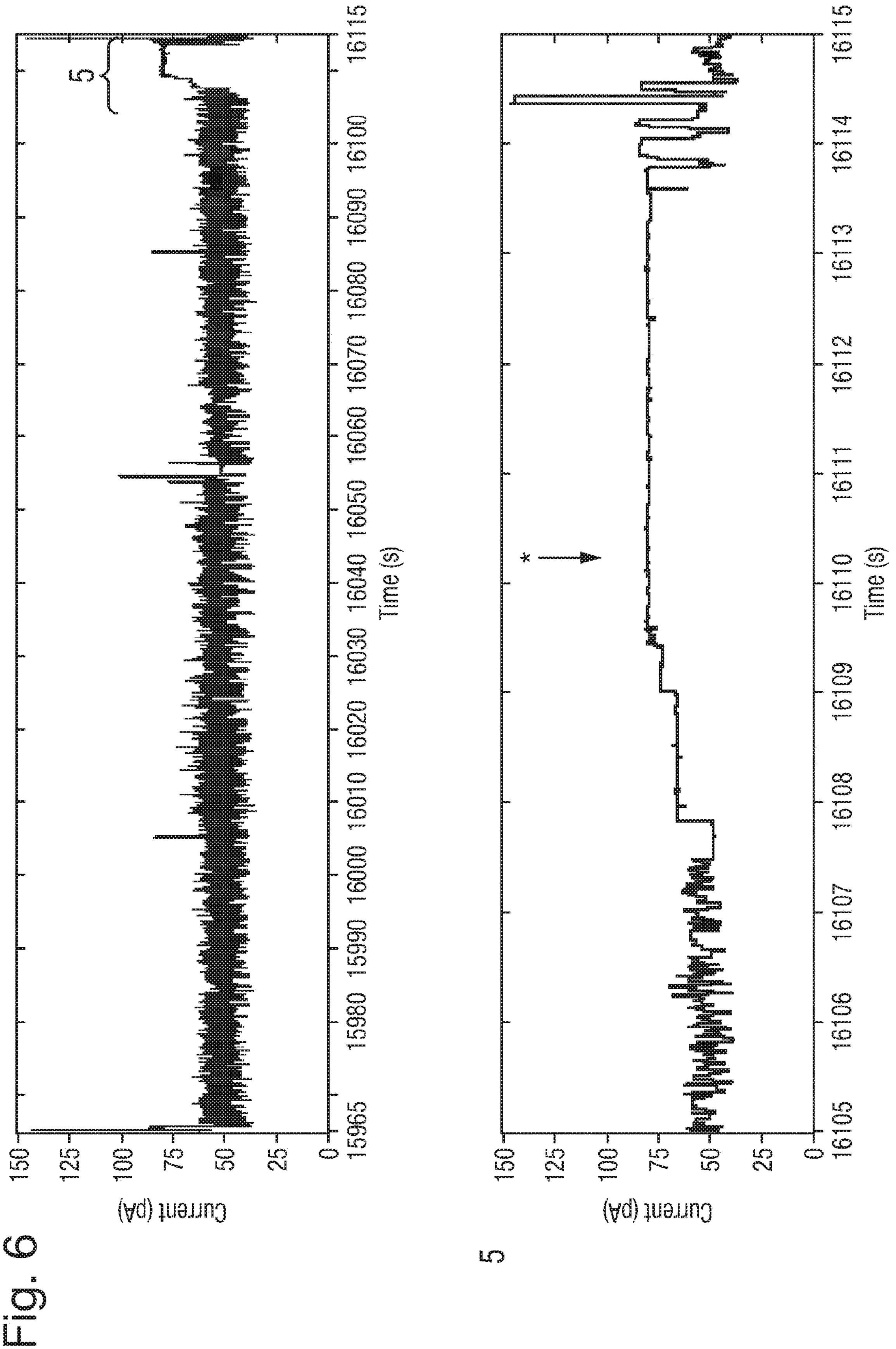
FIG. 6 shows example current traces (y-axis label=Current (pA), x-axis label=Time (s) for both traces) of when a helicase T4 Dda-(E94C/F98W/C109A/C136A/A360C) controlled the translocation of the concatenated polynucleotide through an MspA nanopore. The top trace shows the controlled translocation of the concatenated polynucleotide and the lower trace labelled 5 shows zoomed in region 5 of the top trace.

It is to be understood that Figures are for the purpose of illustrating particular embodiments of the invention only, and are not intended to be limiting.

DESCRIPTION OF THE SEQUENCE LISTING

SEQ ID NO: 1 shows the codon optimised polynucleotide sequence encoding the MS-B1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NO: 3 shows the polynucleotide sequence encoding one monomer of α-hemolysin-E111N/K147N (α-HL-NN; Stoddart et al., PNAS, 2009; 106(19): 7702-7707).

SEQ ID NO: 4 shows the amino acid sequence of one monomer of α-HL-NN.

SEQ ID NOs: 5 to 7 show the amino acid sequences of MspB, C and D.

SEQ ID NO: 8 shows the polynucleotide sequence encoding the Phi29 DNA polymerase.

SEQ ID NO: 9 shows the amino acid sequence of the Phi29 DNA polymerase.

SEQ ID NO: 10 shows the codon optimised polynucleotide sequence derived from the sbcB gene from *E. coli*. It encodes the exonuclease I enzyme (EcoExo I) from *E. coli*.

SEQ ID NO: 11 shows the amino acid sequence of exonuclease I enzyme (EcoExo I) from *E. coli*.

SEQ ID NO: 12 shows the codon optimised polynucleotide sequence derived from the xthA gene from *E. coli*. It encodes the exonuclease III enzyme from *E. coli*.

SEQ ID NO: 13 shows the amino acid sequence of the exonuclease III enzyme from *E. coli*. This enzyme performs distributive digestion of 5' monophosphate nucleosides from one strand of double stranded DNA (dsDNA) in a 3'-5' direction. Enzyme initiation on a strand requires a 5' overhang of approximately 4 nucleotides.

SEQ ID NO: 14 shows the codon optimised polynucleotide sequence derived from the recJ gene from *T. thermophilus*. It encodes the RecJ enzyme from *T. thermophilus* (TthRecJ-cd).

SEQ ID NO: 15 shows the amino acid sequence of the RecJ enzyme from *T. thermophilus* (TthRecJ-cd). This enzyme performs processive digestion of 5' monophosphate nucleosides from ssDNA in a 5'-3' direction. Enzyme initiation on a strand requires at least 4 nucleotides.

SEQ ID NO: 16 shows the codon optimised polynucleotide sequence derived from the bacteriophage lambda exo (redX) gene. It encodes the bacteriophage lambda exonuclease.

SEQ ID NO: 17 shows the amino acid sequence of the bacteriophage lambda exonuclease. The sequence is one of three identical subunits that assemble into a trimer. The enzyme performs highly processive digestion of nucleotides from one strand of dsDNA, in a 5'-3'direction (www.neb.com/nebecomm/products/productM0262.asp). Enzyme initiation on a strand preferentially requires a 5' overhang of approximately 4 nucleotides with a 5' phosphate.

SEQ ID NO: 18 shows the amino acid sequence of Hel308 Mbu.

SEQ ID NO: 19 shows the amino acid sequence of Hel308 Csy.

SEQ ID NO: 20 shows the amino acid sequence of Hel308 Tga.

SEQ ID NO: 21 shows the amino acid sequence of Hel308 Mhu.

SEQ ID NO: 22 shows the amino acid sequence of TraI Eco.

SEQ ID NO: 23 shows the amino acid sequence of XPD Mbu.

SEQ ID NO: 24 shows the amino acid sequence of Dda 1993.

SEQ ID NO: 25 shows the amino acid sequence of Trwc Cba.

SEQ ID NO: 26 shows the codon optimised polynucleotide sequence encoding the wild-type CsgG monomer from *Escherichia coli* Str. K-12 substr. MC4100. This monomer lacks the signal sequence.

SEQ ID NO: 27 shows the amino acid sequence of the mature form of the wild-type CsgG monomer from *Escherichia coli* Str. K-12 substr. MC4100. This monomer lacks the signal sequence. The abbreviation used for this CsgG=CsgG-Eco.

SEQ ID NOs: 28 to 42 show the sequences used in the Examples.

It is to be understood that sequences are not intended to be limiting.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a polynucleotide" includes two or more polynucleotides, reference to "an anchor" refers to two or more anchors, reference to "a helicase" includes two or more helicases, and reference to "a transmembrane pore" includes two or more pores and the like.

In this specification, where different amino acids at a specific position are separated by the symbol "/", the / symbol "/" means "or". For instance, P108R/K means P108R or P108K. In this specification where different positions or different substitutions are separated by the symbol "/", the "/" symbol means "and". For example, E94/P108 means E94 and P108 or E94D/P108K means E94D and P108K.

All publications, patents and patent applications cited herein, whether supra or infra, are hereby incorporated by reference in their entirety.

Method of the Invention

The methods devised by the inventors have various advantages. In known methods of polynucleotide characterization using a transmembrane nanopore, the pore is open for some time after characterising one polynucleotide before a subsequent polynucleotide contacts the pore. The new method significantly reduces the open pore time between polynucleotides because the subsequent polynucleotide is being recruited as the preceding polynucleotide is being characterised. In some embodiments, open pore time may be abolished, substantially abolished or minimised. Not only does a reduced open pore time mean that the pore is doing more characterisation (processing more polynucleotides) than a pore in a conventional method, but it also means that there is a reduced chance of pore blocking (the likelihood of the pore becoming blocked is low, or relatively low compared to in conventional methods). Pore blocking tends to occur when there is an open pore state. If a polynucleotide strand is in the pore then there is a reduced chance of blocking occurring as the pore is already "occupied". Therefore, if the open pore state time is reduced the chance of blocking is also reduced. A reduced open pore also means that the concentration of polynucleotides needed for characterisation is also reduced.

Any number of target polynucleotides can be investigated or characterised using the invention. For instance, the method of the invention may concern characterising two or more polynucleotides, such as 3 or more, 4 or more, 5 or more, 6 or more, 7 or more, 8 or more, 9 or more, 10 or more, 20 or more, 30 or more, 50 or more, 100 or more, 500 or more, 1,000 or more, 5,000 or more, 10,000 or more, 50,000 or more 100,000 or more, 1,000,000 or more or 5,000,000 or more, polynucleotides. In particular, 2 or more, 5 or more, 10 or more, 20 or more, 50 or more, 100 or more, 500 or more, 1,000 or more, 5,000 or more, 10,000 or more, 50,000 or more, 100,000 or more, 500,000 or more, 1,000,000 or more or 5,000,000 or more subsequent target polynucleotides are attached to the first target polynucleotide.

The two or more target polynucleotides may be different from one another. The two or more polynucleotides may be two or more instances of the same polynucleotide. This allows proof reading. The two or more target polynucleotides may be derived from the fragmentation of a longer target polynucleotide.

Concatenated Polynucleotide

The method comprises sequentially attaching to a first target polynucleotide one or more subsequent target polynucleotides to provide a concatenated polynucleotide. The concatenated polynucleotide comprises at least two target polynucleotides attached together.

The target polynucleotides move through the pore in attachment order. For instance, the first target polynucleotide moves through the pore immediately before the second target polynucleotide. The second target polynucleotide moves through the pore immediately before the third target polynucleotide and so on. In other words, the first target polynucleotide moves through the pore followed by the second target polynucleotide. The second target polynucleotide moves through the pore followed by the third target polynucleotide and so on.

Attachment

As target polynucleotides move through a pore, a subsequent target polynucleotide is selectively attached to the preceding target polynucleotide in the attachment order when the preceding target polynucleotide moves through the pore. For instance, the second target polynucleotide is selectively attached to the first target polynucleotide when the first target polynucleotide moves through the pore. The third target polynucleotide is selectively attached to the second target polynucleotide when the second target polynucleotide moves through the pore and so on.

In other words, the target polynucleotides are not attached to one another until a first target polynucleotide interacts with the pore. The interaction of a first target polynucleotide with the pore facilitates the attachment of the first target polynucleotide to a second target polynucleotide. The interaction with the pore may result in a conformational change in the first polynucleotide, such as for example dehybridisation/separation of the two strands of a double stranded target polynucleotide, or removal of a protecting molecule to reveal or expose a site on the first polynucleotide that can interact with a site on the second polynucleotide. After the said site on the first polynucleotide is revealed or exposed, the first polynucleotide attaches to the second polynucleotide. The occurrence of the attachment only when the first polynucleotide interacts with the pore is referred to herein as "selective attachment". This is distinct from "selective hybridisation" which is used herein to describe base pair binding between complementary regions of a first polynucleotide and a second polynucleotide.

Thus, the attachment is selective in the sense that a subsequent target polynucleotide cannot attach to the preceding target polynucleotide in the absence of the pore or until the preceding target polynucleotide moves through the pore. For instance, the attachment is selective in the sense that the second target polynucleotide cannot attach to the first target polynucleotide in the absence of the pore or until the first target polynucleotide moves through the pore. The third target polynucleotide cannot attach to the second target polynucleotide in the absence of the pore or until the second target polynucleotide moves through the pore and so on.

Selective attachment may be achieved in any way. A part of the preceding target polynucleotide (e.g. a site on a first polypeptide which binds to a site on a second polypeptide) is initially protected from attachment to the subsequent target polynucleotide and is revealed for attachment as the preceding target polynucleotide moves through the pore. For instance, a part of the first target polynucleotide is initially protected from attachment to the second target polynucleotide and is revealed for attachment as the first target polynucleotide moves through the pore. A part of the second target polynucleotide is initially protected from attachment to the third target polynucleotide and is revealed for attachment as the second target polynucleotide moves through the pore and so on.

The part may be protected in any way. The part is typically protected by a molecule which prevents attachment. Movement of the preceding target polynucleotide through the pore may remove the molecule and reveal the part for attachment. Any molecule may be used. For instance, a molecule may occlude one of the click reactive groups discussed below. This might be, for example, pyrene to stack with the DBCO. If the part comprises Ni-NTA groups (which can attach to polyhistidine, such as 6×His, in the subsequent target polynucleotide), the part may be protected with polyhistidine, such as 6×His, in the same target polynucleotide and vice versa, i.e. the part comprises polyhistidine, such as 6×His, and is protected by Ni-NTA groups. If the part comprises cyclodextrin (which can attach to amantadine in the subsequent polynucleotide), the part may be protected by amantadine in the same target polynucleotide or vice versa. The part and the protecting molecule may be present on opposite strands of a double stranded target polynucleotide. Separation of the strands by the pore may then separate the protecting molecule from the part and reveal the part for attachment.

The part of the preceding target polynucleotide may be protected by hybridisation to a protecting polynucleotide. The protecting polynucleotide may be separated from the part as the target polynucleotide moves through the pore. The protecting polynucleotide may form part of the target polynucleotide as discussed in more detail below. The protecting polynucleotide may be a separate polynucleotide. As discussed in more detail below, the protecting polynucleotide may protect the part from hybridisation to a part of the subsequent target polynucleotide. Alternatively, the protecting polynucleotide may prevent the action of a single strand ligase on the part. The presence protecting polynucleotide (forming a double stranded region with the part) means the ligase cannot function. Release of the protecting polynucleotide would reveal the part as a substrate for the ligase.

A part of the subsequent target polynucleotide preferably selectively hybridises to a part of the preceding polynucleotide, e.g. the site revealed on the preceding target polynucleotide as a result of its interaction with the pore is a nucleotide sequence that is complementary to a nucleotide sequence on the subsequent polynucleotide. For instance, a part of the second target polynucleotide preferably selectively hybridises to a part of the first polynucleotide. A part of the third target polynucleotide preferably selectively hybridises to a part of the second target polynucleotide and so on.

The part of the preceding target polynucleotide is preferably initially protected from hybridisation to the part of the subsequent target polynucleotide and is revealed for hybridisation as the preceding target polynucleotide moves through the pore. For instance, the part of the second target polynucleotide is preferably initially protected from hybridisation to the part of the first target polynucleotide and is revealed for hybridisation as the first target polynucleotide moves through the pore. The part of the third target polynucleotide is preferably initially protected from hybridisation to the part of the second target polynucleotide and is revealed for hybridisation as the second target polynucleotide moves through the pore and so on.

The part of the preceding target polynucleotide preferably specifically hybridises to the part of the subsequent target polynucleotide. The parts of the target polynucleotides specifically hybridise when they hybridise with preferential or high affinity to each other but do not substantially hybridise, do not hybridise or hybridise with only low affinity to other polynucleotides or sequences. The part of the preceding target polynucleotide specifically hybridises to the part of the subsequent target polynucleotide if it hybridises to the part of the subsequent target polynucleotide with a melting temperature ($T_m$) that is at least 2° C., such as at least 3° C., at least 4° C., at least 5° C., at least 6° C., at least 7° C., at least 8° C., at least 9° C. or at least 10° C., greater than its $T_m$ for other sequences. More preferably, the part of the preceding target polynucleotide hybridises to the part of the subsequent target polynucleotide with a $T_m$ that is at least 2° C., such as at least 3° C., at least 4° C., at least 5° C., at least 6° C., at least 7° C., at least 8° C., at least 9° C., at least 10° C., at least 20° C., at least 30° C. or at least 40° C., greater than its $T_m$ for other sequences. Preferably, the part of the preceding target polynucleotide hybridises to the part of the subsequent target polynucleotide with a $T_m$ that is at least 2° C., such as at least 3° C., at least 4° C., at least 5° C., at least 6° C., at least 7° C., at least 8° C., at least 9° C., at least 10° C., at least 20° C., at least 30° C. or at least 40° C., greater than its $T_m$ for a sequence which differs from the part of the subsequent target polynucleotide by one or more nucleotides, such as by 1, 2, 3, 4 or 5 or more nucleotides. The part of the preceding target polynucleotide typically hybridises to the part of the subsequent target polynucleotide with a $T_m$ of at least 90° C., such as at least 92° C. or at least 95° C. $T_m$ can be measured experimentally using known techniques, including the use of DNA microarrays, or can be calculated using publicly available $T_m$ calculators, such as those available over the internet.

Conditions that permit the hybridisation are well-known in the art (for example, Sambrook et al., 2001, Molecular Cloning: a laboratory manual, 3rd edition, Cold Spring Harbour Laboratory Press; and Current Protocols in Molecular Biology, Chapter 2, Ausubel et al., Eds., Greene Publishing and Wiley-Interscience, New York (1995)). Hybridisation can be carried out under low stringency conditions, for example in the presence of a buffered solution of 30 to 35% formamide, 1 M NaCl and 1% SDS (sodium dodecyl sulfate) at 37° C. followed by a 20 wash in from 1× (0.1650 M $Na^+$) to 2× (0.33 M $Na^+$) SSC (standard sodium citrate) at 50° C. Hybridisation can be carried out under moderate stringency conditions, for example in the presence of a buffer solution of 40 to 45% formamide, 1 M NaCl, and 1% SDS at 37° C., followed by a wash in from 0.5× (0.0825 M $Na^+$) to 1× (0.1650 M $Na^+$) SSC at 55° C. Hybridisation can be carried out under high stringency conditions, for example in the presence of a buffered solution of 50% formamide, 1 M NaCl, 1% SDS at 37° C., followed by a wash in 0.1× (0.0165 M $Na^+$) SSC at 60° C.

The part of the preceding target polynucleotide is preferably substantially complementary to the part of the subsequent target polynucleotide. The part of the preceding target polynucleotide may therefore have 1, 2, 3, 4, 5, 6, 7, 8, 9, 10 or more mismatches across a region of 5, 10, 15, 20, 21, 22, 30, 40 or 50 nucleotides compared with the part of the subsequent target polynucleotide. The part of the preceding target polynucleotide is preferably complementary to the part of the subsequent target polynucleotide.

Each part is typically 50 nucleotides or fewer, such as 40 nucleotides or fewer, 30 nucleotides or fewer, 20 nucleotides or fewer, 12 nucleotides or fewer, 10 nucleotides or fewer or 5 nucleotides or fewer. Each part is typically at least 4 nucleotides in length, such as at least 5 nucleotides, at least 10 nucleotides or at least 12 nucleotides in length.

Each target polynucleotide may comprise the same parts, one which selectively hybridises to a part of the preceding polynucleotide (when it is the subsequent target polynucleotide) and one which selectively hybridises to a part of the subsequent polynucleotide (when it is the preceding polynucleotide). In such embodiment, the two parts in each target polynucleotide must be protected from one another so that they do not attach to each other and only attach to a different target polynucleotide. The parts may be protected from one another in any of the ways discussed above.

In one embodiment, the part of the preceding, e.g. first, polynucleotide that is revealed for attachment to the subsequent, e.g. second, polynucleotide is at, or close to, the opposite end of the preceding polynucleotide to the end that is fed into the pore. Where the polynucleotide passes through the pore in a 5' to 3' direction, the part of the preceding polynucleotide that attaches to the subsequent polynucleotide is at, or close to, the 3' end of the preceding polynucleotide. The part of the subsequent polynucleotide that attaches to the preceding polynucleotide is then at, or close to, the 5' end of the subsequent polynucleotide. A part close to the end of a polynucleotide is typically within, for example, 1 to 30 bases of the end of the polynucleotide, such as within 2 to 25, 3 to 20, 4 to 15 or 5 to 10 bases from the end of the polynucleotide.

In a preferred embodiment, the preceding target polynucleotide is double stranded, the part (attachment site) of the preceding target polynucleotide is in one strand (a first strand) and is hybridised to the other strand (a second strand), and the part (attachment site) is revealed for hybridisation as the two (first and second) strands separate as the preceding target polynucleotide moves through the pore. In this embodiment, the other (second) strand of the target polynucleotide is the protecting molecule. If the second strand moves through the pore, the two strands separate and the part (attachment site on the first strand) is revealed for hybridisation to the part (attachment site) on the subsequent target polynucleotide. A specific version of this embodiment is shown in FIG. 1.

The one (first) strand in the preceding target polynucleotide preferably forms a loop structure at its end. The part (attachment site) of the preceding target polynucleotide which hybridises to the part (attachment site) of the subsequent target polynucleotide is preferably adjacent to, but not part of the loop structure. In such an embodiment, hybridisation of the part in the subsequent target polynucleotide to the part in the preceding target polynucleotide elongates the loop. This embodiment results in the preceding and subsequent target polynucleotides being attached by a loop which may dehybridise and move through the pore. A specific version of this embodiment is shown in FIG. 1.

In one embodiment, both strands of the double stranded preceding target polynucleotide are preferably linked at one end by a hairpin loop. Hairpin loops are discussed in more detail below. If the two strands are linked, the two strands separate, the part is revealed for hybridisation to the part on subsequent target polynucleotide, the hairpin moves through the pore and then the strand comprising the part attached to the subsequent target polynucleotide moves through the pore.

The other (second) strand at the other end of the preceding target polynucleotide preferably comprises a leader sequence which preferentially threads into the pore. This ensures that the other (second) strand enters the pore and the part (attachment site) is revealed for hybridisation as the two strands separate. Suitable leader sequences are discussed in more detail below.

The subsequent target polynucleotide is preferably attached to the one (first) strand at the other end of the preceding target polynucleotide. As the other (second) strand, which preferably comprises a leader sequence, moves through the pore, the part (attachment site) on the one (first) strand is preferably revealed for attachment or hybridisation to the part (attachment site) on the subsequent target polynucleotide.

The subsequent target polynucleotide is preferably double stranded. In one embodiment, the two strands are preferably linked at one end by a hairpin loop. The other end of the subsequent target polynucleotide from the hairpin loop is preferably selectively attached to the preceding target polynucleotide. In particular, the other end of the subsequent target polynucleotide from the hairpin loop preferably comprises a leader sequence which is capable of selectively attaching to the preceding target polynucleotide. The free end of the leader sequence is preferably capable of hybridizing to the part of the preceding target polynucleotide. The free end of the leader sequence is preferably the part of the subsequent target polynucleotide which specifically hybridises to the part of the preceding target polynucleotide. As discussed above, the part of the preceding target polynucleotide is preferably adjacent to a loop structure in the preceding target polynucleotide.

The end of the leader sequence may be hybridised to a bridging polynucleotide which forms an overhang which is capable of selectively attaching to the preceding target polynucleotide. The overhang is preferably capable of hybridizing to the part (attachment site) of the preceding target polynucleotide. The overhang is preferably the part of the subsequent target polynucleotide which specifically hybridises to the part of the preceding target polynucleotide. In other words, the overhang comprises or constitutes the attachment site in the subsequent target polynucleotide. Hybridisation of the overhang to the part (attachment site) in the preceding target polynucleotide positions the leader of the subsequent polynucleotide adjacent to the part (attachment site) in the preceding target polynucleotide and the two parts (attachment sites) may be attached to one another. The bridging polynucleotide and/or the overhang can be any length and formed from any of the polynucleotides discussed below.

The second (subsequent) target polynucleotide is preferably selectively covalently attached to the first (preceding) target polynucleotide. For instance, in one embodiment, the part of the preceding target polynucleotide may hybridise with the part of the second target polynucleotide (e.g. where the attachment sites in the first and second polynucleotides are complementary to one another) and then the two polynucleotides may be covalently attached. Any form of covalent attachment may be used.

The subsequent (second) target polynucleotide is preferably covalently attached to the preceding (first) target polynucleotide using a ligase, a topoisomerase or by click chemistry. The ligase, topoisomerase or click chemistry results in the formation of one or more covalent bonds between the first and second target polynucleotides.

Any ligase may be used, such as T4 DNA ligase, *E. coli* DNA ligase, Taq DNA ligase, Tma DNA ligase and 9° N DNA ligase. The ligase is preferably T3 DNA ligase. This commercially available, for instance from, New England BioLabs® Inc.

Any topoisomerase may be used. Suitable topoisomerases include, but are not limited to, Vaccinia DNA Topoisomerase or Human DNA Topoisomerase I.

Click chemistry is advantageous because it does not typically involve the use of enzymes. Click chemistry is a term first introduced by Kolb et al. in 2001 to describe an expanding set of powerful, selective, and modular building blocks that work reliably in both small- and large-scale applications (Kolb H C, Finn, M G, Sharpless K B, Click chemistry: diverse chemical function from a few good reactions, Angew. Chem. Int. Ed. 40 (2001) 2004-2021). They have defined the set of stringent criteria for click chemistry as follows: "The reaction must be modular, wide in scope, give very high yields, generate only inoffensive byproducts that can be removed by nonchromatographic methods, and be stereospecific (but not necessarily enantioselective). The required process characteristics include simple reaction conditions (ideally, the process should be insensitive to oxygen and water), readily available starting materials and reagents, the use of no solvent or a solvent that is benign (such as water) or easily removed, and simple product isolation. Purification if required must be by non-chromatographic methods, such as crystallization or distillation, and the product must be stable under physiological conditions".

Suitable example of click chemistry include, but are not limited to, the following:

(a) copper-free variant of the 1,3 dipolar cycloaddition reaction, where an azide reacts with an alkyne under strain, for example in a cyclooctane ring;

(b) the reaction of an oxygen nucleophile on one linker with an epoxide or aziridine reactive moiety on the other; and (c) the Staudinger ligation, where the alkyne moiety can be replaced by an aryl phosphine, resulting in a specific reaction with the azide to give an amide bond.

Preferably the click chemistry reaction is the Cu (I) catalysed 1,3 dipolar cycloaddition reaction between an alkyne and an azide. In a preferred embodiment, the first group is an azide group and the second group is an alkyne group. Nucleic acid bases have already been synthesised incorporating azide and alkyne groups in preferred positions (for example Kocalka P, El-Sagheer A H, Brown T, Rapid and efficient DNA strand cross-linking by click chemistry, Chembiochem. 2008. 9(8):1280-5). Alkyne groups are available commercially from Berry Associates (Michigan, USA) and azide groups are synthesised by ATDBio.

If the preceding and subsequent polynucleotides or part thereof are modified to include groups that can form covalent bonds, the modified nucleotides are preferably offset from one another by one nucleotide in order to achieve the link. This follows the published work of Tom Brown (Kocalka et al. (2008) ChemBiochem 9 8 1280-1285).

Other preferred groups for use in the invention are shown in the following Table 1.

TABLE 1

Some preferred groups capable of forming covalent bonds

| Name | Reacts with | Structure |
|---|---|---|
| 1,4-Bis[3-(2-pyridyldithio)propionamido]butane | Thiols | 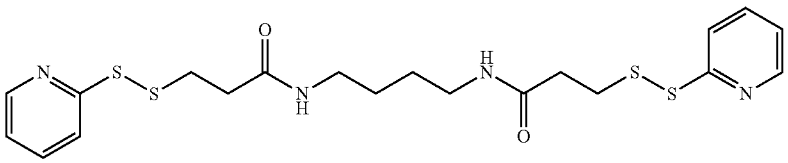 [SMILES: O=C(CCSSc1ccccn1)NCCCCNC(=O)CCSSc1ccccn1] |
| 1,11-bis-Maleimidotriethyleneglycol | Thiols | 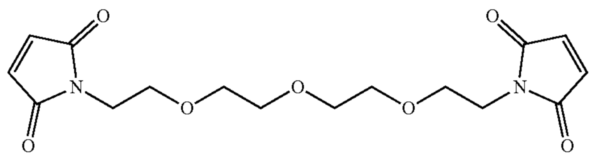 [SMILES: O=C1C=CC(=O)N1CCOCCOCCOCCN1C(=O)C=CC1=O] |

TABLE 1-continued

| Some preferred groups capable of forming covalent bonds | | |
|---|---|---|
| Name | Reacts with | Structure |
| 3,3'-Dithiodipropionic acid di(N-hydroxysuccinimide ester) | Primary amines | 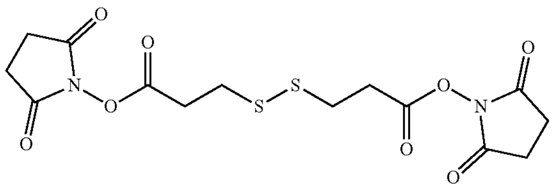 [SMILES: O=C(CCSSCCC(=O)ON1C(=O)CCC1=O)ON1C(=O)CCC1=O] |
| Ethylene glycol-bis(succinic acid N-hydroxysuccinimide ester) | Primary amines | 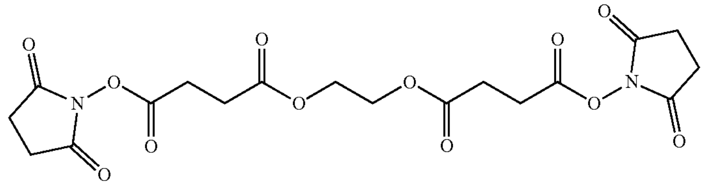 [SMILES: O=C(CCC(=O)ON1C(=O)CCC1=O)OCCOC(=O)CCC(=O)ON1C(=O)CCC1=O] |
| 4,4'-Diisothiocyanatostilbene-2,2'-disulfonic acid disodium salt | Primary amines | 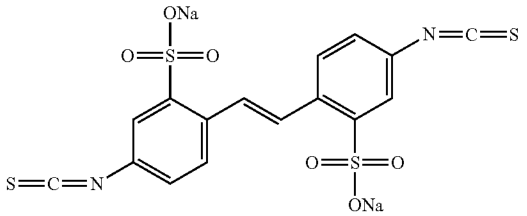 |
| Bis[2-(4-azidosalicylamido)ethyl] disulfide | Photo-activated, non-specific | 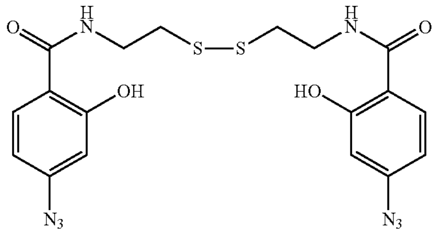 [SMILES: [N-]=[N+]=Nc1ccc(C(=O)NCCSSCCNC(=O)c2ccc(N=[N+]=[N-])cc2O)c(O)c1] |
| 3-(2-Pyridyldithio)propionic acid N-hydroxysuccinimide ester | Thiols, primary amines | 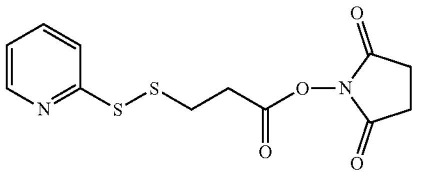 [SMILES: O=C(CCSSc1ccccn1)ON1C(=O)CCC1=O] |
| 4-Maleimidobutyric acid N-hydroxysuccinimide ester | Thiols, primary amines | 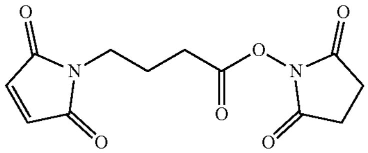 [SMILES: O=C(CCCN1C(=O)C=CC1=O)ON1C(=O)CCC1=O] |
| Iodoacetic acid N-hydroxysuccinimide ester | Thiols, primary amines | 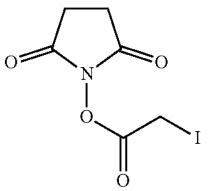 [SMILES: O=C(CI)ON1C(=O)CCC1=O] |

TABLE 1-continued

Some preferred groups capable of forming covalent bonds

| Name | Reacts with | Structure |
|---|---|---|
| S-Acetylthioglycolic acid N-hydroxysuccinimide ester | Thiols, primary amines | 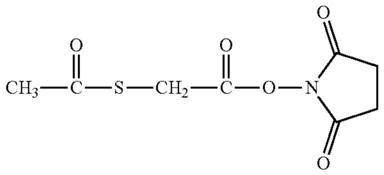 |
| Azide-PEG-maleimide | Thiols, alkyne | 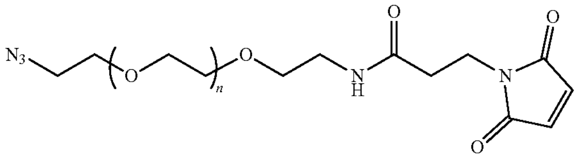<br>n = 5, 10 |
| Alkyne-PEG-maleimide | Thiols, azide | 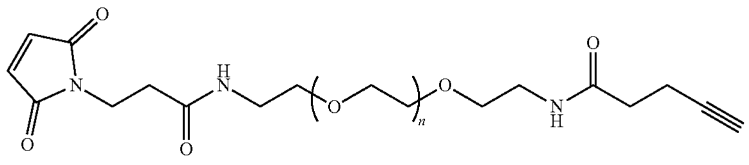<br>n = 6, 10 |

Copper free click chemistry can be used in the invention because of its desirable properties. For example, it is fast, clean and not poisonous towards proteins. A good example of this is maleimide or iodoacetamide linking with a cyclooctyne functional group (DIBO). However, other suitable bio-orthogonal chemistries include, but are not limited to, Staudinger chemistry, hydrazine or hydrazide/aldehyde or ketone reagents (HyNic+4FB chemistry, including all Solulink™ reagents), Diels-Alder reagent pairs and boronic acid/salicyhydroxamate reagents.

Preferably the reactive groups are azide and hexynl groups such as 3AzideN and 5'-hexynl-G.

Preferred pairs of non-covalent reactive groups include, but are not limited to, (i) Ni-NTA and polyhistidine, such as 6×His, and (ii) cyclodextrin and adamantine.

Polynucleotide

The two more target polynucleotides may be any type of polynucleotide. A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the polynucleotide can be oxidised or methylated. One or more nucleotides in the polynucleotide may be damaged. For instance, the polynucleotide may comprise a pyrimidine dimer. Such dimers are typically associated with damage by ultraviolet light and are the primary cause of skin melanomas. One or more nucleotides in the polynucleotide may be modified, for instance with a label or a tag. Suitable labels are described below. The polynucleotide may comprise one or more spacers.

A nucleotide typically contains a nucleobase, a sugar and at least one phosphate group. The nucleobase and sugar form a nucleoside.

The nucleobase is typically heterocyclic. Nucleobases include, but are not limited to, purines and pyrimidines and more specifically adenine (A), guanine (G), thymine (T), uracil (U) and cytosine (C).

The sugar is typically a pentose sugar. Nucleotide sugars include, but are not limited to, ribose and deoxyribose. The sugar is preferably a deoxyribose.

The polynucleotide preferably comprises the following nucleosides: deoxyadenosine (dA), deoxyuridine (dU) and/or thymidine (dT), deoxyguanosine (dG) and deoxycytidine (dC).

The nucleotide is typically a ribonucleotide or deoxyribonucleotide. The nucleotide typically contains a monophosphate, diphosphate or triphosphate. The nucleotide may comprise more than three phosphates, such as 4 or 5 phosphates. Phosphates may be attached on the 5' or 3' side of a nucleotide. Nucleotides include, but are not limited to, adenosine monophosphate (AMP), guanosine monophosphate (GMP), thymidine monophosphate (TMP), uridine monophosphate (UMP), 5-methylcytidine monophosphate, 5-hydroxymethylcytidine monophosphate, cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP), deoxycytidine monophosphate (dCMP) and deoxymethylcytidine monophosphate. The nucleotides are preferably selected from AMP, TMP, GMP, CMP, UMP, dAMP, dTMP, dGMP, dCMP and dUMP.

A nucleotide may be abasic (i.e. lack a nucleobase). A nucleotide may also lack a nucleobase and a sugar (i.e. is a C3 spacer).

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide may be single stranded or double stranded. At least a portion of the polynucleotide is preferably double stranded.

The polynucleotide can be a nucleic acid, such as deoxyribonucleic acid (DNA) or ribonucleic acid (RNA). The polynucleotide can comprise one strand of RNA hybridised to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains. The PNA backbone is composed of repeating N-(2-aminoethyl)-glycine units linked by peptide bonds. The GNA backbone is composed of repeating glycol units linked by phosphodiester bonds. The TNA backbone is composed of repeating threose sugars linked together by phosphodiester bonds. LNA is formed from ribonucleotides as discussed above having an extra bridge connecting the 2' oxygen and 4' carbon in the ribose moiety.

The polynucleotide is most preferably ribonucleic nucleic acid (RNA) or deoxyribonucleic acid (DNA).

The polynucleotide can be any length. For example, the polynucleotide can be at least 10, at least 50, at least 100, at least 150, at least 200, at least 250, at least 300, at least 400 or at least 500 nucleotides or nucleotide pairs in length. The polynucleotide can be 1000 or more nucleotides or nucleotide pairs, 5000 or more nucleotides or nucleotide pairs in length or 100000 or more nucleotides or nucleotide pairs in length.

Sample

The target polynucleotides may be present in any suitable sample. The sample may be a biological sample. The invention may be carried out in vitro using at least one sample obtained from or extracted from any organism or microorganism. The organism or microorganism is typically archaeal, prokaryotic or eukaryotic and typically belongs to one of the five kingdoms: plantae, animalia, fungi, monera and protista. The invention may be carried out in vitro on at least one sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep, fish, chickens or pigs or may alternatively be pets such as cats or dogs. Alternatively, the sample may be of plant origin, such as a sample obtained from a commercial crop, such as a cereal, legume, fruit or vegetable, for example wheat, barley, oats, canola, maize, soya, rice, rhubarb, bananas, apples, tomatoes, potatoes, grapes, tobacco, beans, lentils, sugar cane, cocoa, broccoli or cotton.

The sample may be a non-biological sample. The non-biological sample is preferably a fluid sample. Examples of non-biological samples include surgical fluids, water such as drinking water, sea water or river water, and reagents for laboratory tests.

The sample is typically processed prior to being used in the invention, for example by centrifugation or by passage through a membrane that filters out unwanted molecules or cells, such as red blood cells. The sample may be measured immediately upon being taken. The sample may also be typically stored prior to assay, preferably below −70° C.

Membrane

The polynucleotides are contacted with a transmembrane pore in a membrane. Any membrane may be used in accordance with the invention. Suitable membranes are well-known in the art. The membrane is preferably an amphiphilic layer. An amphiphilic layer is a layer formed from amphiphilic molecules, such as phospholipids, which have both hydrophilic and lipophilic properties. The amphiphilic molecules may be synthetic or naturally occurring. Non-naturally occurring amphiphiles and amphiphiles which form a monolayer are known in the art and include, for example, block copolymers (Gonzalez-Perez et al., Langmuir, 2009, 25, 10447-10450). Block copolymers are polymeric materials in which two or more monomer sub-units are polymerised together to create a single polymer chain. Block copolymers typically have properties that are contributed by each monomer sub-unit. However, a block copolymer may have unique properties that polymers formed from the individual sub-units do not possess. Block copolymers can be engineered such that one of the monomer sub-units is hydrophobic (i.e. lipophilic), whilst the other sub-unit(s) are hydrophilic whilst in aqueous media. In this case, the block copolymer may possess amphiphilic properties and may form a structure that mimics a biological membrane. The block copolymer may be a diblock (consisting of two monomer sub-units), but may also be constructed from more than two monomer sub-units to form more complex arrangements that behave as amphiphiles. The copolymer may be a triblock, tetrablock or pentablock copolymer. The membrane is preferably a triblock copolymer membrane.

Archaebacterial bipolar tetraether lipids are naturally occurring lipids that are constructed such that the lipid forms a monolayer membrane. These lipids are generally found in extremophiles that survive in harsh biological environments, thermophiles, halophiles and acidophiles. Their stability is believed to derive from the fused nature of the final bilayer. It is straightforward to construct block copolymer materials that mimic these biological entities by creating a triblock polymer that has the general motif hydrophilic-hydrophobic-hydrophilic. This material may form monomeric membranes that behave similarly to lipid bilayers and encompass a range of phase behaviours from vesicles through to laminar membranes. Membranes formed from these triblock copolymers hold several advantages over biological lipid membranes. Because the triblock copolymer is synthesised, the exact construction can be carefully controlled to provide the correct chain lengths and properties required to form membranes and to interact with pores and other proteins.

Block copolymers may also be constructed from sub-units that are not classed as lipid sub-materials; for example a hydrophobic polymer may be made from siloxane or other non-hydrocarbon based monomers. The hydrophilic sub-section of block copolymer can also possess low protein binding properties, which allows the creation of a membrane that is highly resistant when exposed to raw biological samples. This head group unit may also be derived from non-classical lipid head-groups.

Triblock copolymer membranes also have increased mechanical and environmental stability compared with biological lipid membranes, for example a much higher operational temperature or pH range. The synthetic nature of the block copolymers provides a platform to customise polymer based membranes for a wide range of applications.

The membrane is most preferably one of the membranes disclosed in International Application No. PCT/GB2013/052766 (published as WO 2014/064443) or PCT/GB2013/052767 (published as WO 2014/064444).

The amphiphilic molecules may be chemically-modified or functionalised to facilitate coupling of the polynucleotide.

The amphiphilic layer may be a monolayer or a bilayer. The amphiphilic layer is typically planar. The amphiphilic layer may be curved. The amphiphilic layer may be supported. The amphiphilic layer may be concave. The amphiphilic layer may be suspended from raised pillars such that the peripheral region of the amphiphilic layer (which is attached to the pillars) is higher than the amphiphilic layer region. This may allow the microparticle to travel, move, slide or roll along the membrane as described above.

Amphiphilic membranes are typically naturally mobile, essentially acting as two dimensional fluids with lipid diffusion rates of approximately $10^{-8}$ cm s-1. This means that the pore and coupled polynucleotide can typically move within an amphiphilic membrane.

The membrane may be a lipid bilayer. Lipid bilayers are models of cell membranes and serve as excellent platforms for a range of experimental studies. For example, lipid bilayers can be used for in vitro investigation of membrane proteins by single-channel recording. Alternatively, lipid bilayers can be used as biosensors to detect the presence of a range of substances. The lipid bilayer may be any lipid bilayer. Suitable lipid bilayers include, but are not limited to, a planar lipid bilayer, a supported bilayer or a liposome. The lipid bilayer is preferably a planar lipid bilayer. Suitable lipid bilayers are disclosed in International Application No. PCT/GB08/000563 (published as WO 2008/102121), International Application No. PCT/GB08/004127 (published as WO 2009/077734) and International Application No. PCT/GB2006/001057 (published as WO 2006/100484).

Methods for forming lipid bilayers are known in the art. Suitable methods are disclosed in the Example. Lipid bilayers are commonly formed by the method of Montal and Mueller (Proc. Natl. Acad. Sci. USA., 1972; 69: 3561-3566), in which a lipid monolayer is carried on aqueous solution/air interface past either side of an aperture which is perpendicular to that interface. The lipid is normally added to the surface of an aqueous electrolyte solution by first dissolving it in an organic solvent and then allowing a drop of the solvent to evaporate on the surface of the aqueous solution on either side of the aperture. Once the organic solvent has evaporated, the solution/air interfaces on either side of the aperture are physically moved up and down past the aperture until a bilayer is formed. Planar lipid bilayers may be formed across an aperture in a membrane or across an opening into a recess.

The method of Montal & Mueller is popular because it is a cost-effective and relatively straightforward method of forming good quality lipid bilayers that are suitable for protein pore insertion. Other common methods of bilayer formation include tip-dipping, painting bilayers and patch-clamping of liposome bilayers.

Tip-dipping bilayer formation entails touching the aperture surface (for example, a pipette tip) onto the surface of a test solution that is carrying a monolayer of lipid. Again, the lipid monolayer is first generated at the solution/air interface by allowing a drop of lipid dissolved in organic solvent to evaporate at the solution surface. The bilayer is then formed by the Langmuir-Schaefer process and requires mechanical automation to move the aperture relative to the solution surface.

For painted bilayers, a drop of lipid dissolved in organic solvent is applied directly to the aperture, which is submerged in an aqueous test solution. The lipid solution is spread thinly over the aperture using a paintbrush or an equivalent. Thinning of the solvent results in the formation of a lipid bilayer. However, complete removal of the solvent from the bilayer is difficult and consequently the bilayer formed by this method is less stable and more prone to noise during electrochemical measurement.

Patch-clamping is commonly used in the study of biological cell membranes. The cell membrane is clamped to the end of a pipette by suction and a patch of the membrane becomes attached over the aperture. The method has been adapted for producing lipid bilayers by clamping liposomes which then burst to leave a lipid bilayer sealing over the aperture of the pipette. The method requires stable, giant and unilamellar liposomes and the fabrication of small apertures in materials having a glass surface.

Liposomes can be formed by sonication, extrusion or the Mozafari method (Colas et al. (2007) Micron 38:841-847).

In a preferred embodiment, the lipid bilayer is formed as described in International Application No. PCT/GB08/004127 (published as WO 2009/077734). Advantageously in this method, the lipid bilayer is formed from dried lipids. In a most preferred embodiment, the lipid bilayer is formed across an opening as described in WO2009/077734 (PCT/GB08/004127).

A lipid bilayer is formed from two opposing layers of lipids. The two layers of lipids are arranged such that their hydrophobic tail groups face towards each other to form a hydrophobic interior. The hydrophilic head groups of the lipids face outwards towards the aqueous environment on each side of the bilayer. The bilayer may be present in a number of lipid phases including, but not limited to, the liquid disordered phase (fluid lamellar), liquid ordered phase, solid ordered phase (lamellar gel phase, interdigitated gel phase) and planar bilayer crystals (lamellar sub-gel phase, lamellar crystalline phase).

Any lipid composition that forms a lipid bilayer may be used. The lipid composition is chosen such that a lipid bilayer having the required properties, such as surface charge, ability to support membrane proteins, packing density or mechanical properties, is formed. The lipid composition can comprise one or more different lipids. For instance, the lipid composition can contain up to 100 lipids. The lipid composition preferably contains 1 to 10 lipids. The lipid composition may comprise naturally-occurring lipids and/or artificial lipids.

The lipids typically comprise a head group, an interfacial moiety and two hydrophobic tail groups which may be the same or different. Suitable head groups include, but are not limited to, neutral head groups, such as diacylglycerides (DG) and ceramides (CM); zwitterionic head groups, such as phosphatidylcholine (PC), phosphatidylethanolamine (PE) and sphingomyelin (SM); negatively charged head groups, such as phosphatidylglycerol (PG); phosphatidylserine (PS), phosphatidylinositol (PI), phosphatic acid (PA) and cardiolipin (CA); and positively charged headgroups, such as trimethylammonium-Propane (TAP). Suitable interfacial moieties include, but are not limited to, naturally-occurring interfacial moieties, such as glycerol-based or ceramide-based moieties. Suitable hydrophobic tail groups include, but are not limited to, saturated hydrocarbon chains, such as lauric acid (n-Dodecanolic acid), myristic acid (n-Tetradecononic acid), palmitic acid (n-Hexadecanoic acid), stearic acid (n-Octadecanoic) and arachidic (n-Eicosanoic); unsaturated hydrocarbon chains, such as oleic acid (cis-9-Octadecanoic); and branched hydrocarbon chains, such as phytanoyl. The length of the chain and the position and number of the double bonds in the unsaturated hydrocarbon chains can vary. The length of the chains and the position and number of the branches, such as methyl groups, in the branched hydrocarbon chains can vary. The hydrophobic tail groups can be linked to the interfacial moiety as an ether or an ester. The lipids may be mycolic acid.

The lipids can also be chemically-modified. The head group or the tail group of the lipids may be chemically-modified. Suitable lipids whose head groups have been chemically-modified include, but are not limited to, PEG-modified lipids, such as 1,2-Diacyl-sn-Glycero-3-Phosphoethanolamine-N-[Methoxy(Polyethylene glycol)-2000]; functionalised PEG Lipids, such as 1,2-Distearoyl-sn-Glycero-3 Phosphoethanolamine-N-[Biotinyl(Polyethylene Glycol)2000]; and lipids modified for conjugation, such as 1,2-Dioleoyl-sn-Glycero-3-Phosphoethanolamine-N-(succinyl) and 1,2-Dipalmitoyl-sn-Glycero-3-Phosphoethanolamine-N-(Biotinyl). Suitable lipids whose tail groups have been chemically-modified include, but are not limited to, polymerisable lipids, such as 1,2-bis(10,12-tricosadiynoyl)-sn-Glycero-3-Phosphocholine; fluorinated lipids, such as 1-Palmitoyl-2-(16-Fluoropalmitoyl)-sn-Glycero-3-Phosphocholine; deuterated lipids, such as 1,2-Dipalmitoyl-D62-sn-Glycero-3-Phosphocholine; and ether linked lipids, such as 1,2-Di-O-phytanyl-sn-Glycero-3-Phosphocholine. The lipids may be chemically-modified or functionalised to facilitate coupling of the polynucleotide.

The amphiphilic layer, for example the lipid composition, typically comprises one or more additives that will affect the properties of the layer. Suitable additives include, but are not limited to, fatty acids, such as palmitic acid, myristic acid and oleic acid; fatty alcohols, such as palmitic alcohol, myristic alcohol and oleic alcohol; sterols, such as cholesterol, ergosterol, lanosterol, sitosterol and stigmasterol; lysophospholipids, such as 1-Acyl-2-Hydroxy-sn-Glycero-3-Phosphocholine; and ceramides.

In another preferred embodiment, the membrane is a solid state layer. Solid state layers can be formed from both organic and inorganic materials including, but not limited to, microelectronic materials, insulating materials such as $HfO_2$, $Si_3N_4$, $A1_2O_3$, and SiO, organic and inorganic polymers such as polyamide, plastics such as Teflon® or elastomers such as two-component addition-cure silicone rubber, and glasses. The solid state layer may be by atomic layer deposition (ALD). The ALD solid state layer may comprise alternating layers of $HfO_2$ and $A1_2O_3$. The solid state layer may be formed from monatomic layers, such as graphene, or layers that are only a few atoms thick. Suitable graphene layers are disclosed in International Application No. PCT/US2008/010637 (published as WO 2009/035647). Yusko et al., Nature Nanotechnology, 2011; 6: 253-260 and US Patent Application No. 2013/0048499 describe the delivery of proteins to transmembrane pores in solid state layers without the use of microparticles. The method of the invention may be used to improve the delivery in the methods disclosed in these documents.

The method is typically carried out using (i) an artificial amphiphilic layer comprising a pore, (ii) an isolated, naturally-occurring lipid bilayer comprising a pore, or (iii) a cell having a pore inserted therein. The method is typically carried out using an artificial amphiphilic layer, such as an artificial triblock copolymer layer. The layer may comprise other transmembrane and/or intramembrane proteins as well as other molecules in addition to the pore. Suitable apparatus and conditions are discussed below. The method of the invention is typically carried out in vitro.

Transmembrane Pore

A transmembrane pore is a structure that crosses the membrane to some degree. Typically, a transmembrane pore comprises a first opening and a second opening with a lumen extending between the first opening and the second opening. The transmembrane pore permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well, gap, channel, trench or slit in the membrane along which or into which hydrated ions may flow.

Any transmembrane pore may be used in the invention. The pore may be biological or artificial. Suitable pores include, but are not limited to, protein pores, polynucleotide pores and solid state pores. The pore may be a DNA origami pore (Langecker et al., Science, 2012; 338: 932-936).

The transmembrane pore is preferably a transmembrane protein pore. A transmembrane protein pore is a polypeptide or a collection of polypeptides that permits hydrated ions, such as polynucleotide, to flow from one side of a membrane to the other side of the membrane. In the present invention, the transmembrane protein pore is capable of forming a pore that permits hydrated ions driven by an applied potential to flow from one side of the membrane to the other. The transmembrane protein pore preferably permits polynucleotides to flow from one side of the membrane, such as a triblock copolymer membrane, to the other. The transmembrane protein pore allows a polynucleotide, such as DNA or RNA, to be moved through the pore.

The transmembrane protein pore may be a monomer or an oligomer. The pore is preferably made up of several repeating subunits, such as at least 6, at least 7, at least 8, at least 9, at least 10, at least 11, at least 12, at least 13, at least 14, at least 15, or at least 16 subunits. The pore is preferably a hexameric, heptameric, octameric or nonameric pore. The pore may be a homo-oligomer or a hetero-oligomer.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with s, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA, MspB, MspC or MspD, CsgG, outer membrane porin F (OmpF), outer membrane porin G (OmpG), outer membrane phospholipase A and *Neisseria* autotransporter lipoprotein (NalP) and other pores, such as lysenin. α-helix bundle pores comprise a barrel or channel that is formed from α-helices. Suitable α-helix bundle pores include, but are not limited to, inner membrane proteins and α outer membrane proteins, such as WZA and ClyA toxin. The transmembrane pore may be derived from lysenin. Suitable pores derived from CsgG are disclosed in International Application No. PCT/EP2015/069965. Suitable pores derived from lysenin are disclosed in International Application No. PCT/GB2013/050667 (published as WO 2013/153359). The transmembrane pore may be derived from or based on Msp, α-hemolysin (α-HL), lysenin, CsgG, ClyA, Sp1 and haemolytic protein fragaceatoxin C (FraC). The wild type α-hemolysin pore is formed of 7 identical monomers or sub-units (i.e., it is heptameric). The sequence of one monomer or sub-unit of α-hemolysin-NN is shown in SEQ ID NO: 4.

The transmembrane protein pore is preferably derived from Msp, more preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp typically comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a triblock copolymer membrane such that it diffuses to the membrane and is inserted by binding to the membrane and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid similarity or identity. More preferably, the variant may be at least 55%, at least 60%, at least 65%, at least 70%, at least 75%, at least 80%, at least 85%, at least 90% and more preferably at least 95%, 97% or 99% homologous based on amino acid similarity or identity to the amino acid sequence of SEQ ID NO: 2 over the entire sequence. There may be at least 80%, for example at least 85%, 90% or 95%, amino acid similarity or identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et al (1984) Nucleic Acids Research 12, p387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S.F et al (1990) J Mol Biol 215:403-10. Software for performing BLAST analyses is publicly available through the National Center for Biotechnology Information (www.ncbi.nlm.nih.gov/). Similarity can be measured using pairwise identity or by applying a scoring matrix such as BLOSUM62 and converting to an equivalent identity. Since they represent functional rather than evolved changes, deliberately mutated positions would be masked when determining homology. Similarity may be determined more sensitively by the application of position-specific scoring matrices using, for example, PSIBLAST on a comprehensive database of protein sequences. A different scoring matrix could be used that reflect amino acid chemico-physical properties rather than frequency of substitution over evolutionary time scales (e.g. charge).

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation L88N. A variant of SEQ ID NO: 2 has the mutation L88N in addition to all the mutations of MS-B1 and is called MS-(B2)8. The pore used in the invention is preferably MS-(B2)8. The variant of SEQ ID NO: 2 preferably comprises one or more of D56N, D56F, E59R, G75S, G77S, A96D and Q126R. A variant of SEQ ID NO: 2 has the mutations G75S/G77S/L88N/Q126R in addition to all the mutations of MS-B1 and is called MS-B2C. The pore used in the invention is preferably MS-(B2)8 or MS-(B2C)8. The variant of SEQ ID NO: 2 preferably comprises N93D. The variant more preferably comprises the mutations G75S/G77S/L88N/N93D/Q126R.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid.

The transmembrane protein pore is preferably derived from CsgG, more preferably from CsgG from *E. coli* Str. K-12 substr. MC4100. Such a pore will be oligomeric and typically comprises 7, 8, 9 or 10 monomers derived from CsgG. The pore may be a homo-oligomeric pore derived from CsgG comprising identical monomers. Alternatively, the pore may be a hetero-oligomeric pore derived from CsgG comprising at least one monomer that differs from the others.

A monomer derived from CsgG typically comprises the sequence shown in SEQ ID NO: 27 or a variant thereof. A variant of SEQ ID NO: 27 is a polypeptide that has an amino acid sequence which varies from that of SEQ ID NO: 27 and which retains its ability to form a pore. The ability of a variant to form a pore can be assayed using any method known in the art as discussed above.

Over the entire length of the amino acid sequence of any one of SEQ ID NO: 27, a variant will preferably be at least 50% homologous to that sequence based on amino acid similarity or identity. More preferably, the variant may be at least 55%, at least 60%, at least 65%, at least 70%, at least 75%, at least 80%, at least 85%, at least 90% and more preferably at least 95%, 97% or 99% homologous based on amino acid similarity or identity to the amino acid sequence of SEQ ID NO: 27 over the entire sequence. There may be at least 80%, for example at least 85%, 90% or 95%, amino acid similarity or identity over a stretch of 100 or more, for example 125, 150, 175 or 200 or more, contiguous amino acids ("hard homology"). Homology can be measured as discussed above.

The variant of SEQ ID NO: 27 may comprise any of the mutations disclosed in International Application No. PCT/GB2015/069965 (published as WO 2016/034591). The variant of SEQ ID NO: 27 preferably comprises one or more of the following (i) one or more mutations at the following positions (i.e. mutations at one or more of the following positions) N40, D43, E44, S54, S57, Q62, R97, E101, E124, E131, R142, T150 and R192, such as one or more mutations at the following positions (i.e. mutations at one or more of the following positions) N40, D43, E44, S54, S57, Q62, E101, E131 and T150 or N40, D43, E44, E101 and E131; (ii) mutations at Y51/N55, Y51/F56, N55/F56 or Y51/N55/F56; (iii) Q42R or Q42K; (iv) K49R; (v) N102R, N102F, N102Y or N102W; (vi) D149N, D149Q or D149R; (vii) E185N, E185Q or E185R; (viii) D195N, D195Q or D195R; (ix) E201N, E201Q or E201R; (x) E203N, E203Q or E203R; and (xi) deletion of one or more of the following positions F48, K49, P50, Y51, P52, A53, S54, N55, F56 and S57. The variant may comprise any combination of (i) to (xi). If the variant comprises any one of (i) and (iii) to (xi), it may further comprise a mutation at one or more of Y51, N55 and F56, such as at Y51, N55, F56, Y51/N55, Y51/F56, N55/F56 or Y51/N55/F56.

Preferred variants of SEQ ID NO: 27 which form pores in which fewer nucleotides contribute to the current as the polynucleotide moves through the pore comprise Y51A/F56A, Y51A/F56N, Y51I/F56A, Y51L/F56A, Y51T/F56A, Y51I/F56N, Y51L/F56N or Y51T/F56N or more preferably Y51I/F56A, Y51L/F56A or Y51T/F56A.

Preferred variants of SEQ ID NO: 27 which form pores displaying an increased range comprise mutations at the following positions:

Y51, F56, D149, E185, E201 and E203;
N55 and F56;
Y51 and F56;
Y51, N55 and F56; or
F56 and N102.

Preferred variants of SEQ ID NO: 27 which form pores displaying an increased range comprise:

Y51N, F56A, D149N, E185R, E201N and E203N;
N55S and F56Q;
Y51A and F56A;
Y51A and F56N;
Y51I and F56A;
Y51L and F56A;
Y51T and F56A;
Y51I and F56N;
Y51L and F56N;
Y51T and F56N;
Y51T and F56Q;
Y51A, N55S and F56A;
Y51A, N55S and F56N;
Y51T, N55S and F56Q; or
F56Q and N102R.

Preferred variants of SEQ ID NO: 27 which form pores in which fewer nucleotides contribute to the current as the polynucleotide moves through the pore comprise mutations at the following positions:

N55 and F56, such as N55X and F56Q, wherein X is any amino acid; or

Y51 and F56, such as Y51X and F56Q, wherein X is any amino acid.

Preferred variants of SEQ ID NO: 27 which form pores displaying an increased throughput comprise mutations at the following positions:

D149, E185 and E203;
D149, E185, E201 and E203; or
D149, E185, D195, E201 and E203.

Preferred variants which form pores displaying an increased throughput comprise:

D149N, E185N and E203N;
D149N, E185N, E201N and E203N;
D149N, E185R, D195N, E201N and E203N; or
D149N, E185R, D195N, E201R and E203N.

Preferred variants of SEQ ID NO: 7 which form pores in which capture of the polynucleotide is increased comprise the following mutations:

D43N/Y51T/F56Q;
E44N/Y51T/F56Q;
D43N/E44N/Y51T/F56Q;
Y51T/F56Q/Q62R;
D43N/Y51T/F56Q/Q62R;
E44N/Y51T/F56Q/Q62R; or
D43N/E44N/Y51T/F56Q/Q62R.

Preferred variants of SEQ ID NO: 27 comprise the following mutations:

D149R/E185R/E201R/E203R or Y51T/F56Q/D149R/E185R/E201R/E203R;
D149N/E185N/E201N/E203N or Y51T/F56Q/D149N/E185N/E201N/E203N;
E201R/E203R or Y51T/F56Q/E201R/E203R
E201N/E203R or Y51T/F56Q/E201N/E203R;
E203R or Y51T/F56Q/E203R;
E203N or Y51T/F56Q/E203N;
E201R or Y51T/F56Q/E201R;
E201N or Y51T/F56Q/E201N;
E185R or Y51T/F56Q/E185R;
E185N or Y51T/F56Q/E185N;
D149R or Y51T/F56Q/D149R;
D149N or Y51T/F56Q/D149N;
R142E or Y51T/F56Q/R142E;
R142N or Y51T/F56Q/R142N;
R192E or Y51T/F56Q/R192E; or
R192N or Y51T/F56Q/R192N.

Preferred variants of SEQ ID NO: 27 comprise the following mutations:

Y51A/F56Q/E101N/N102R;
Y51A/F56Q/R97N/N102G;
Y51A/F56Q/R97N/N102R;
Y51A/F56Q/R97N;
Y51A/F56Q/R97G;
Y51A/F56Q/R97L;
Y51A/F56Q/N102R;
Y51A/F56Q/N102F;
Y51A/F56Q/N102G;
Y51A/F56Q/E101R;
Y51A/F56Q/E101F;
Y51A/F56Q/E101N; or
Y51A/F56Q/E101G

The variant of SEQ ID NO: 27 may comprise any of the substitutions present in another CsgG homologue. Preferred CsgG homologues are shown in SEQ ID NOs: 3 to 7 and 26 to 41 of International Application No. PCT/GB2015/069965 (published as WO 2016/034591).

Any of the proteins described herein, such as the transmembrane protein pores, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the pore or construct. An example of this would be to react a gel-shift reagent to a cysteine engineered on the outside of the pore. This has been demonstrated as a method for separating hemolysin hetero-oligomers (Chem Biol. 1997 July; 4(7):497-505).

The pore may be labelled with a revealing label. The revealing label may be any suitable label which allows the pore to be detected. Suitable labels include, but are not limited to, fluorescent molecules, radioisotopes, e.g. $^{125}I$, $^{35}S$, enzymes, antibodies, antigens, polynucleotides and ligands such as biotin.

Any of the proteins described herein, such as the transmembrane protein pores, may be made synthetically or by recombinant means. For example, the pore may be synthesised by in vitro translation and transcription (IVTT). The amino acid sequence of the pore may be modified to include non-naturally occurring amino acids or to increase the stability of the protein. When a protein is produced by synthetic means, such amino acids may be introduced during production. The pore may also be altered following either synthetic or recombinant production.

Any of the proteins described herein, such as the transmembrane protein pores, can be produced using standard methods known in the art. Polynucleotide sequences encoding a pore or construct may be derived and replicated using standard methods in the art. Polynucleotide sequences encoding a pore or construct may be expressed in a bacterial host cell using standard techniques in the art. The pore may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

The pore may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

Microparticle

A microparticle may be used to deliver the target polynucleotide to the transmembrane pore. Any number of microparticles can be used in the method of the invention. For instance, the method of the invention may use a single microparticle or 2, 3, 4, 5, 6, 7, 8, 9, 10, 20, 30, 50, 100, 1,000, 5,000, 10,000, 100,000, 500,000 or 1,000,000 or more microparticles. If two or more microparticles are used, the microparticles may be the same. Alternatively, a mixture of different microparticles may be used.

Each microparticle may have one polynucleotide attached. Alternatively, each microparticle may have two or more polynucleotides, such as 3 or more, 4 or more, 5 or more, 6 or more, 7 or more, 8 or more, 9 or more, 10 or more, 20 or more, 30 or more, 50 or more, 100 or more, 500 or more, 1,000 or more, 5,000 or more, 10,000 or more, 100,000 or more, 1000,000 or more or 5000,000 or more polynucleotides, attached. A microparticle may be substantially or completed coated or covered with polynucleotide. A microparticle may have a polynucleotide attached over substantially all of or all of its surface. A microparticle may be attached to a polynucleotide via an adaptor. The adaptor may be a Y-adaptor or a hairpin adaptor (see below)

A polynucleotide, i.e. a single instance of an polynucleotide, may be attached to two or more microparticles. A polynucleotide, i.e. a single instance of an polynucleotide, may be attached to any number of the microparticles discussed above.

A microparticle is a microscopic particle whose size is typically measured in micrometres (μm). Microparticles may also known as microspheres or microbeads. The microparticle may be a nanoparticle. A nanoparticle is a microscopic particle whose size is typically measured in nanometres (nm).

A microparticle typically has a particle size of from about 0.001 μm to about 500 μm. For instance, a nanoparticle may have a particle size of from about 0.01 μm to about 200 μm or about 0.1 μm to about 100 μm. More often, a microparticle has a particle size of from about 0.5 μm to about 100 μm, or for instance from about 1 μm to about 50 μm. The microparticle may have a particle size of from about 1 nm to about 1000 nm, such as from about 10 nm to about 500 nm, about 20 nm to about 200 nm or from about 30 nm to about 100 nm.

A microparticle may be spherical or non-spherical. Spherical microparticles may be called microspheres. Non-spherical particles may for instance be plate-shaped, needle-shaped, irregular or tubular. The term "particle size" as used herein means the diameter of the particle if the particle is spherical or, if the particle is non-spherical, the volume-based particle size. The volume-based particle size is the diameter of the sphere that has the same volume as the non-spherical particle in question.

If two or more microparticles are used in the method, the average particle size of the microparticles may be any of the sizes discussed above, such as from about 0.5 μm to about 500 μm. A population of two or more microparticles preferably has a coefficient of variation (ratio of the standard deviation to the mean) of 10% or less, such as 5% or less or 2% or less.

Any method may be used to determine the size of the microparticle. Suitable methods include, but are not limited to, flow cytometry (see, for example, Chandler et al., J Thromb Haemost. 2011 June; 9(6):1216-24).

The microparticle may be formed from any material. The microparticle is preferably formed from a ceramic, glass, silica, a polymer or a metal. The polymer may be a natural polymer, such as polyhydroxyalkanoate, dextran, polylactide, agarose, cellulose, starch or chitosan, or a synthetic polymer, such as polyurethane, polystyrene, poly(vinyl chloride), silane or methacrylate. Suitable microparticles are known in the art and are commercially available. Ceramic and glass microspheres are commercially available from 3M®. Silica and polymer microparticles are commercially available from EPRUI Nanoparticles & Microspheres Co. Ltd. Microparticles are also commercially available from Polysciences Inc., Bangs Laboratories Inc. and Life Technologies.

The microparticle may be solid. The microparticle may be hollow. The microparticle may be formed from polymer fibers.

The microparticle may be derived from the kit used to extract and isolate the polynucleotide.

The surface of the microparticle may interact with and attach the polynucleotide. The surface may naturally interact with the polynucleotide without functionalisation. The surface of the microparticle is typically functionalised to facilitate attachment of the polynucleotide. Suitable functionalisations are known in the art. For instance, the surface of the microparticle may be functionalised with a polyhistidine-tag (hexa histidine-tag, 6×His-tag, His6 tag or His-Tag®), Ni-NTA, streptavidin, biotin, an oligonucleotide, a polynucleotide (such as DNA, RNA, PNA, GNA, TNA or LNA), carboxyl groups, quaternary amine groups, thiol groups, azide groups, alkyne groups, DIBO, lipid, FLAG-tag (FLAG octapeptide, polynucleotide binding proteins (including any of those discussed below), peptides, proteins, antibodies or antibody fragments. Antibody fragments are discussed in more detail below. The microparticle may also be functionalised with any of the linkers or groups discussed below with reference to attachment.

The microparticle may be functionalised with a molecule or group which specifically binds to the polynucleotide. In this instance, the polynucleotide which will be attached to the microparticle and delivered to the transmembrane pore may be called the target polynucleotide. This allows the microparticle to select or capture the target polynucleotide from a sample containing other polynucleotides. A molecule or group specifically binds to the target polynucleotide if it binds to the target polynucleotide with preferential or high affinity, but does not bind or binds with only low affinity to other or different polynucleotides. A molecule or group binds with preferential or high affinity if it binds with a Kd of $1\times10^{-6}$ M or less, more preferably $1\times10^{-7}$ M or less, $5\times10^{-8}$ M or less, more preferably $1\times10^{-8}$ M or less or more preferably $5\times10^{-9}$ M or less. A molecule or group binds with low affinity if it binds with a Kd of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

Preferably, the molecule or group binds to the target polynucleotide with an affinity that is at least 10 times, such as at least 50, at least 100, at least 200, at least 300, at least 400, at least 500, at least 1000 or at least 10,000 times, greater than its affinity for other polynucleotides. Affinity can be measured using known binding assays, such as those that make use of fluorescence and radioisotopes. Competitive binding assays are also known in the art. The strength of binding between peptides or proteins and polynucleotides can be measured using nanopore force spectroscopy as described in Hornblower et al., Nature Methods. 4: 315-317. (2007).

The microparticle may be functionalised with an oligonucleotide or a polynucleotide (such as any of those discussed above) which specifically hybridises to the target polynucleotide or comprises a portion or region which is complementary to a portion or region of the target polynucleotide. This allows the microparticle to select or capture the target polynucleotide from a sample containing other polynucleotides. An oligonucleotide or polynucleotide specifically hybridises to a target polynucleotide when it hybridises with preferential or high affinity to the target polynucleotide but does not substantially hybridise, does not hybridise or hybridises with only low affinity to other polynucleotide. An oligonucleotide or polynucleotide specifically hybridises if it hybridises to the target polynucleotide with a melting temperature ($T_m$) that is at least 2° C., such as at least 3° C., at least 4° C., at least 5° C., at least 6° C., at least 7° C., at least 8° C., at least 9° C. or at least 10° C., greater than its $T_m$ for other sequences. More preferably, the oligonucleotide or polynucleotide hybridises to the target polynucleotide with a $T_m$ that is at least 2° C., such as at least 3° C., at least 4° C., at least 5° C., at least 6° C., at least 7° C., at least 8° C., at least 9° C., at least 10° C., at least 20° C., at least 30° C. or at least 40° C., greater than its $T_m$ for other nucleic acids. Preferably, the oligonucleotide or polynucleotide hybridises to the target polynucleotide with a $T_m$ that is at least 2° C., such as at least 3° C., at least 4° C., at least 5° C., at least 6° C., at least 7° C., at least 8° C., at least 9° C., at least 10° C., at least 20° C., at least 30° C. or at least 40° C., greater than its $T_m$ for a sequence which differs from the target polynucleotide by one or more nucleotides, such as by 1, 2, 3, 4 or 5 or more nucleotides. The oligonucleotide or polynucleotide typically hybridises to the target polynucleotide with a $T_m$ of at least 90° C., such as at least 92° C. or at least 95° C. $T_m$ can be measured experimentally using known techniques, including the use of DNA microarrays, or can be calculated using publicly available $T_m$ calculators, such as those available over the internet.

Conditions that permit the hybridisation are well-known in the art (for example, Sambrook et al., 2001, Molecular Cloning: a laboratory manual, 3rd edition, Cold Spring Harbour Laboratory Press; and Current Protocols in Molecular Biology, Chapter 2, Ausubel et al., Eds., Greene Publishing and Wiley-lnterscience, New York (1995)). Hybridisation can be carried out under low stringency conditions, for example in the presence of a buffered solution of 30 to 35% formamide, 1 M NaCl and 1% SDS (sodium dodecyl sulfate) at 37° C. followed by a 20 wash in from 1× (0.1650 M $Na^+$) to 2× (0.33 M $Na^+$) SSC (standard sodium citrate) at 50° C. Hybridisation can be carried out under moderate stringency conditions, for example in the presence of a buffer solution of 40 to 45% formamide, 1 M NaCl, and 1% SDS at 37° C., followed by a wash in from 0.5× (0.0825 M $Na^+$) to 1× (0.1650 M $Na^+$) SSC at 55° C. Hybridisation can be carried out under high stringency conditions, for example in the presence of a buffered solution of 50% formamide, 1 M NaCl, 1% SDS at 37° C., followed by a wash in 0.1× (0.0165 M $Na^+$) SSC at 60° C.

The oligonucleotide or polynucleotide may comprise a portion or region which is substantially complementary to a portion or region of the target polynucleotide. The region or portion of the oligonucleotide or polynucleotide may therefore have 1, 2, 3, 4, 5, 6, 7, 8, 9, 10 or more mismatches across a region of 5, 10, 15, 20, 21, 22, 30, 40 or 50 nucleotides compared with the portion or region in the target polynucleotide.

A portion of region is typically 50 nucleotides or fewer, such as 40 nucleotides or fewer, 30 nucleotides or fewer, 20 nucleotides or fewer, 10 nucleotides or fewer or 5 nucleotides or fewer.

The microparticle is preferably paramagnetic or magnetic. The microparticle preferably comprises a paramagnetic or a superparamagnetic material or a paramagnetic or a superparamagnetic metal, such as iron. Any suitable magnetic microparticle may be used. For instance, magnetic beads commercially available from, for instance, Clontech, Promega, Invitrogen ThermoFisher Scientific and NEB, may be used. In some embodiments, the microparticle comprises a magnetic particle with an organic group such as a metal-chelating group, such as nitrilotriacetic acid (NTA), attached. The organic component may, for instance, comprise a group selected from —C(═O)O—, —C—O—C—, —C(═O)—, —NH—, —C(═O)—NH, —C(═O)—$CH_2$—I, —S(═O)$_2$— and —S—. The organic component may comprise a metal chelating group, such as NTA (nitrilotriacetic acid). Usually, a metal such as gold, iron, nickel or cobalt is also attached to the metal-chelating group. Magnetic beads of this sort are commonly used for capturing His-tagged proteins, but are also suitable for use in the invention.

The microparticle is most preferably a His-Tag Dynabead® which is commercially available from Life Technologies, Mag Strep beads from IBA, Streptavidin magnetic beads from NEB, Solid Phase Reversible Immobilization (SPRI) beads or Agencourt AMPure XP beads from Beckman Coulter or Dynabeads® MyOne™ Streptavidin C1 (ThermoFisher Scientific).

Coupling

The first target polynucleotide and/or the one or more subsequent target polynucleotides preferably comprise one or more anchors which are capable of coupling to the membrane. The method preferably further comprises coupling the target polynucleotide to the membrane using the one or more anchors.

The anchor comprises a group which couples (or binds) to the polynucleotide and a group which couples (or binds) to the membrane. Each anchor may covalently couple (or bind) to the polynucleotide and/or the membrane.

The polynucleotide may be coupled to the membrane using any number of anchors, such as 2, 3, 4 or more anchors. For instance, the polynucleotide may be coupled to the membrane using two anchors each of which separately couples (or binds) to both the polynucleotide and membrane.

The one or more anchors may comprise one or more molecular brakes. Each anchor may comprise one or more molecular brakes. The molecular brake(s) may be any of those discussed below.

If the membrane is an amphiphilic layer, such as a triblock copolymer membrane, the one or more anchors preferably comprise a polypeptide anchor present in the membrane and/or a hydrophobic anchor present in the membrane. The hydrophobic anchor is preferably a lipid, fatty acid, sterol, carbon nanotube, polypeptide, protein or amino acid, for example cholesterol, palmitate or tocopherol. In preferred embodiments, the one or more anchors are not the pore.

The components of the membrane, such as the amphiphilic molecules, copolymer or lipids, may be chemically-modified or functionalised to form the one or more anchors. Examples of suitable chemical modifications and suitable ways of functionalising the components of the membrane are discussed in more detail below. Any proportion of the membrane components may be functionalised, for example at least 0.01%, at least 0.1%, at least 1%, at least 10%, at least 25%, at least 50% or 100%.

The polynucleotide may be coupled directly to the membrane. The one or more anchors used to couple the polynucleotide to the membrane preferably comprise a linker. The one or more anchors may comprise one or more, such as 2, 3, 4 or more, linkers. One linker may be used to couple more than one, such as 2, 3, 4 or more, polynucleotides to the membrane.

Preferred linkers include, but are not limited to, polymers, such as polynucleotides, polyethylene glycols (PEGs), polysaccharides and polypeptides. These linkers may be linear, branched or circular. For instance, the linker may be a circular polynucleotide. The polynucleotide may hybridise to a complementary sequence on the circular polynucleotide linker.

The one or more anchors or one or more linkers may comprise a component that can be cut or broken down, such as a restriction site or a photolabile group.

Functionalised linkers and the ways in which they can couple molecules are known in the art. For instance, linkers functionalised with maleimide groups will react with and attach to cysteine residues in proteins. In the context of this invention, the protein may be present in the membrane, may be the polynucleotide itself or may be used to couple (or bind) to the polynucleotide. This is discussed in more detail below.

Crosslinkage of polynucleotides can be avoided using a "lock and key" arrangement. Only one end of each linker may react together to form a longer linker and the other ends of the linker each react with the polynucleotide or membrane respectively. Such linkers are described in International Application No. PCT/GB10/000132 (published as WO 2010/086602).

The use of a linker is preferred in the sequencing embodiments discussed below. If a polynucleotide is permanently coupled directly to the membrane in the sense that it does not uncouple when interacting with the pore, then some sequence data will be lost as the sequencing run cannot continue to the end of the polynucleotide due to the distance between the membrane and the pore. If a linker is used, then the polynucleotide can be processed to completion.

The coupling may be permanent or stable. In other words, the coupling may be such that the polynucleotide remains coupled to the membrane when interacting with the pore.

The coupling may be transient. In other words, the coupling may be such that the polynucleotide may decouple from the membrane when interacting with the pore. For certain applications, such as aptamer detection and polynucleotide sequencing, the transient nature of the coupling is preferred. If a permanent or stable linker is attached directly to either the 5' or 3' end of a polynucleotide and the linker is shorter than the distance between the membrane and the transmembrane pore's channel, then some sequence data will be lost as the sequencing run cannot continue to the end of the polynucleotide. If the coupling is transient, then when the coupled end randomly becomes free of the membrane, then the polynucleotide can be processed to completion. Chemical groups that form permanent/stable or transient links are discussed in more detail below. The polynucleotide may be transiently coupled to an amphiphilic layer or triblock copolymer membrane using cholesterol or a fatty acyl chain. Any fatty acyl chain having a length of from 6 to 30 carbon atom, such as hexadecanoic acid, may be used.

In preferred embodiments, a polynucleotide, such as a nucleic acid, is coupled to an amphiphilic layer such as a triblock copolymer membrane or lipid bilayer. Coupling of nucleic acids to synthetic lipid bilayers has been carried out previously with various different tethering strategies. These are summarised in Table 2 below.

TABLE 2

| Anchor comprising | Type of coupling | Reference |
|---|---|---|
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with anchored DNA molecules." *Biophys J* 92(12): 4356-68 |
| Cholesterol | Transient | Pfeiffer, I. and F. Hook (2004). "Bivalent cholesterol-based coupling of oligonucletides to lipid membrane assemblies." *J Am Chem Soc* 126(33): 10224-5 |

TABLE 2-continued

| Anchor comprising | Type of coupling | Reference |
|---|---|---|
| Surfactant (e.g. Lipid, Palmitate, etc) | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Synthetic polynucleotides and/or linkers may be functionalised using a modified phosphoramidite in the synthesis reaction, which is easily compatible for the direct addition of suitable anchoring groups, such as cholesterol, tocopherol, palmitate, thiol, lipid and biotin groups. These different attachment chemistries give a suite of options for attachment to polynucleotides. Each different modification group couples the polynucleotide in a slightly different way and coupling is not always permanent so giving different dwell times for the polynucleotide to the membrane. The advantages of transient coupling are discussed above.

Coupling of polynucleotides to a linker or to a functionalised membrane can also be achieved by a number of other means provided that a complementary reactive group or an anchoring group can be added to the polynucleotide. The addition of reactive groups to either end of a polynucleotide has been reported previously. A thiol group can be added to the 5' of ssDNA or dsDNA using T4 polynucleotide kinase and ATPγS (Grant, G. P. and P. Z. Qin (2007). "A facile method for attaching nitroxide spin labels at the 5' terminus of nucleic acids." *Nucleic Acids Res* 35(10): e77). An azide group can be added to the 5'-phosphate of ssDNA or dsDNA using T4 polynucleotide kinase and γ-[2-Azidoethyl]-ATP or γ-[6-Azidohexyl]-ATP. Using thiol or Click chemistry a tether, containing either a thiol, iodoacetamide OPSS or maleimide group (reactive to thiols) or a DIBO (dibenzocyclooxtyne) or alkyne group (reactive to azides), can be covalently attached to the polynucleotide. A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." *Anal Biochem* 169(2): 376-82). Streptavidin/biotin and/or streptavidin/desthiobiotin coupling may be used for any other polynucleotide. The Examples below describes how a polynucleotide can be coupled to a membrane using streptavidin/biotin and streptavidin/desthiobiotin. It may also be possible that anchors may be directly added to polynucleotides using terminal transferase with suitably modified nucleotides (e.g. cholesterol or palmitate).

The one or more anchors preferably couple the polynucleotide to the membrane via hybridisation. The hybridisation may be present in any part of the one or more anchors, such as between the one or more anchors and the polynucleotide, within the one or more anchors or between the one or more anchors and the membrane. Hybridisation in the one or more anchors allows coupling in a transient manner as discussed above. For instance, a linker may comprise two or more polynucleotides, such as 3, 4 or 5 polynucleotides, hybridised together. The one or more anchors may hybridise to the polynucleotide. The one or more anchors may hybridise directly to the polynucleotide, directly to a Y adaptor and/or leader sequence attached to the polynucleotide or directly to a hairpin loop adaptor attached to the polynucleotide (as discussed in more detail below). Alternatively, the one or more anchors may be hybridised to one or more, such as 2 or 3, intermediate polynucleotides (or "splints") which are hybridised to the polynucleotide, to a Y adaptor and/or leader sequence attached to the polynucleotide or to a hairpin loop adaptor attached to the polynucleotide (as discussed in more detail below).

The one or more anchors may comprise a single stranded or double stranded polynucleotide. One part of the anchor may be ligated to a single stranded or double stranded polynucleotide analyte. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." Proc Natl Acad Sci USA 89(20): 9823-5). Alternatively, either a single stranded or double stranded polynucleotide can be ligated to a double stranded polynucleotide and then the two strands separated by thermal or chemical denaturation. To a double stranded polynucleotide, it is possible to add either a piece of single stranded polynucleotide to one or both of the ends of the duplex, or a double stranded polynucleotide to one or both ends. For addition of single stranded polynucleotides to the double stranded polynucleotide, this can be achieved using T4 RNA ligase I as for ligation to other regions of single stranded polynucleotides. For addition of double stranded polynucleotides to a double stranded polynucleotide then ligation can be "blunt-ended", with complementary 3' dA/dT tails on the polynucleotide and added polynucleotide respectively (as is routinely done for many sample prep applications to prevent concatemer or dimer formation) or using "sticky-ends" generated by restriction digestion of the polynucleotide and ligation of compatible adapters. Then, when the duplex is melted, each single strand will have either a 5' or 3' modification if a single stranded polynucleotide was used for ligation or a modification at the 5' end, the 3' end or both if a double stranded polynucleotide was used for ligation.

If the polynucleotide is a synthetic strand, the one or more anchors can be incorporated during the chemical synthesis of the polynucleotide. For instance, the polynucleotide can be synthesised using a primer having a reactive group attached to it.

Adenylated polynucleotides are intermediates in ligation reactions, where an adenosine-monophosphate is attached to the 5'-phosphate of the polynucleotide. Various kits are available for generation of this intermediate, such as the 5' DNA Adenylation Kit from NEB. By substituting ATP in the reaction for a modified nucleotide triphosphate, then addition of reactive groups (such as thiols, amines, biotin, azides, etc) to the 5' of a polynucleotide can be possible. It may also be possible that anchors could be directly added to polynucleotides using a 5' DNA adenylation kit with suitably modified nucleotides (e.g. cholesterol or palmitate).

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. Single or multiple nucleotides can be added to 3' end of single or double stranded DNA by employing a polymerase. Examples of polymerases which could be used include, but are not limited to, Terminal Transferase, Klenow and *E. coli* Poly(A) polymerase). By substituting ATP in the reaction for a modified nucleotide triphosphate then anchors, such as cholesterol, thiol, amine, azide, biotin or lipid, can be incorporated into double stranded polynucleotides. Therefore, each copy of the amplified polynucleotide will contain an anchor.

Ideally, the polynucleotide is coupled to the membrane without having to functionalise the polynucleotide. This can be achieved by coupling the one or more anchors, such as a molecular brake or a chemical group, to the membrane and allowing the one or more anchors to interact with the polynucleotide or by functionalizing the membrane. The one or more anchors may be coupled to the membrane by any of the methods described herein. In particular, the one or more anchors may comprise one or more linkers, such as maleimide functionalised linkers.

In this embodiment, the polynucleotide is typically RNA, DNA, PNA, TNA or LNA and may be double or single stranded. This embodiment is particularly suited to genomic DNA polynucleotides.

The one or more anchors can comprise any group that couples to, binds to or interacts with single or double stranded polynucleotides, specific nucleotide sequences within the polynucleotide or patterns of modified nucleotides within the polynucleotide, or any other ligand that is present on the polynucleotide.

Suitable binding proteins for use in anchors include, but are not limited to, *E. coli* single stranded binding protein, P5 single stranded binding protein, T4 gp32 single stranded binding protein, the TOPO V dsDNA binding region, human histone proteins, *E. coli* HU DNA binding protein and other archaeal, prokaryotic or eukaryotic single stranded or double stranded polynucleotide (or nucleic acid) binding proteins, including those listed below.

The specific nucleotide sequences could be sequences recognised by transcription factors, ribosomes, endonucleases, topoisomerases or replication initiation factors. The patterns of modified nucleotides could be patterns of methylation or damage.

The one or more anchors can comprise any group which couples to, binds to, intercalates with or interacts with a polynucleotide. The group may intercalate or interact with the polynucleotide via electrostatic, hydrogen bonding or Van der Waals interactions. Such groups include a lysine monomer, poly-lysine (which will interact with ssDNA or dsDNA), ethidium bromide (which will intercalate with dsDNA), universal bases or universal nucleotides (which can hybridise with any polynucleotide) and osmium complexes (which can react to methylated bases). A polynucleotide may therefore be coupled to the membrane using one or more universal nucleotides attached to the membrane. Each universal nucleotide may be coupled to the membrane using one or more linkers. The universal nucleotide preferably comprises one of the following nucleobases: hypoxanthine, 4-nitroindole, 5-nitroindole, 6-nitroindole, formylindole, 3-nitropyrrole, nitroimidazole, 4-nitropyrazole, 4-nitrobenzimidazole, 5-nitroindazole, 4-aminobenzimidazole or phenyl (C6-aromatic ring). The universal nucleotide more preferably comprises one of the following nucleosides: 2'-deoxyinosine, inosine, 7-deaza-2'-deoxyinosine, 7-deaza-inosine, 2-aza-deoxyinosine, 2-aza-inosine, 2-O'-methyl-inosine, 4-nitroindole 2'-deoxyribonucleoside, 4-nitroindole ribonucleoside, 5-nitroindole 2'-deoxyribonucleoside, 5-nitroindole ribonucleoside, 6-nitroindole 2'-deoxyribonucleoside, 6-nitroindole ribonucleoside, 3-nitropyrrole 2'-deoxyribonucleoside, 3-nitropyrrole ribonucleoside, an acyclic sugar analogue of hypoxanthine, nitroimidazole 2'-deoxyribonucleoside, nitroimidazole ribonucleoside, 4-nitropyrazole 2'-deoxyribonucleoside, 4-nitropyrazole ribonucleoside, 4-nitrobenzimidazole 2'-deoxyribonucleoside, 4-nitrobenzimidazole ribonucleoside, 5-nitroindazole 2'-deoxyribonucleoside, 5-nitroindazole ribonucleoside, 4-aminobenzimidazole 2'-deoxyribonucleoside, 4-aminobenzimidazole ribonucleoside, phenyl C-ribonucleoside, phenyl C-2'-deoxyribosyl nucleoside, 2'-deoxynebularine, 2'-deoxyisoguanosine, K-2'-deoxyribose, P-2'-deoxyribose and pyrrolidine. The universal nucleotide more preferably comprises 2'-deoxyinosine. The universal nucleotide is more preferably IMP or dIMP. The universal nucleotide is most preferably dPMP (2'-Deoxy-P-nucleoside monophosphate) or dKMP (N6-methoxy-2, 6-diaminopurine monophosphate).

The one or more anchors may couple to (or bind to) the polynucleotide via Hoogsteen hydrogen bonds (where two nucleobases are held together by hydrogen bonds) or reversed Hoogsteen hydrogen bonds (where one nucleobase is rotated through 180° with respect to the other nucleobase). For instance, the one or more anchors may comprise one or more nucleotides, one or more oligonucleotides or one or more polynucleotides which form Hoogsteen hydrogen bonds or reversed Hoogsteen hydrogen bonds with the polynucleotide. These types of hydrogen bonds allow a third polynucleotide strand to wind around a double stranded helix and form a triplex. The one or more anchors may couple to (or bind to) a double stranded polynucleotide by forming a triplex with the double stranded duplex.

In this embodiment at least 1%, at least 10%, at least 25%, at least 50% or 100% of the membrane components may be functionalised.

Where the one or more anchors comprise a protein, they may be able to anchor directly into the membrane without further functionalisation, for example if it already has an external hydrophobic region which is compatible with the membrane. Examples of such proteins include, but are not limited to, transmembrane proteins, intramembrane proteins and membrane proteins. Alternatively the protein may be expressed with a genetically fused hydrophobic region which is compatible with the membrane. Such hydrophobic protein regions are known in the art.

The one or more anchors are preferably mixed with the polynucleotide before delivery to the membrane, but the one or more anchors may be contacted with the membrane and subsequently contacted with the polynucleotide.

In another aspect the polynucleotide may be functionalised, using methods described above, so that it can be recognised by a specific binding group. Specifically the polynucleotide may be functionalised with a ligand such as biotin (for binding to streptavidin), amylose (for binding to maltose binding protein or a fusion protein), Ni-NTA (for binding to poly-histidine or poly-histidine tagged proteins) or peptides (such as an antigen).

According to a preferred embodiment, the one or more anchors may be used to couple a polynucleotide to the membrane when the polynucleotide is attached to a leader sequence which preferentially threads into the pore. Leader sequences are discussed in more detail below. Preferably, the polynucleotide is attached (such as ligated) to a leader sequence which preferentially threads into the pore. Such a leader sequence may comprise a homopolymeric polynucleotide or an abasic region. The leader sequence is typically designed to hybridise to the one or more anchors either directly or via one or more intermediate polynucleotides (or splints). In such instances, the one or more anchors typically comprise a polynucleotide sequence which is complementary to a sequence in the leader sequence or a sequence in the one or more intermediate polynucleotides (or splints). In such instances, the one or more splints typically comprise a polynucleotide sequence which is complementary to a sequence in the leader sequence.

Any of the methods discussed above for coupling polynucleotides to membranes, such as amphiphilic layers, can of course be applied to other polynucleotide and membrane combinations. In some embodiments, an amino acid, peptide, polypeptide or protein is coupled to an amphiphilic layer, such as a triblock copolymer layer or lipid bilayer. Various methodologies for the chemical attachment of such polynucleotides are available. An example of a molecule used in chemical attachment is EDC (1-ethyl-3-[3-dimethylaminopropyl]carbodiimide hydrochloride). Reactive groups can also be added to the 5' of polynucleotides using commercially available kits (Thermo Pierce, Part No. 22980). Suitable methods include, but are not limited to, transient affinity attachment using histidine residues and Ni-NTA, as well as more robust covalent attachment by reactive cysteines, lysines or non natural amino acids.

Polynucleotide Characterisation

The method of the invention involves characterising the target polynucleotides. As the target polynucleotides are contacted with the pore, one or more measurements which are indicative of one or more characteristics of the target polynucleotides are taken as the concatenated polynucleotide moves with respect to the pore.

The polynucleotides can be naturally occurring or artificial. For instance, the method may be used to verify the sequence of two or more manufactured oligonucleotides. The methods are typically carried out in vitro.

The method may involve measuring two, three, four or five or more characteristics of each polynucleotide. The one or more characteristics are preferably selected from (i) the length of the polynucleotide, (ii) the identity of the polynucleotide, (iii) the sequence of the polynucleotide, (iv) the secondary structure of the polynucleotide and (v) whether or not the polynucleotide is modified. Any combination of (i) to (v) may be measured in accordance with the invention, such as {i}, {ii}, {iii}, {iv}, {v}, {i,ii}, {i,iii}, {i,iv}, {i,v}, {ii,iii}, {ii,iv}, {ii,v}, {iii,iv}, {iii,v}, {iv,v}, {i,ii,iii}, {i,ii,iv}, {i,ii,v}, {i,iii,iv}, {i,iii,v}, {i,iv,v}, {ii,iii,iv}, {ii,iii,v}, {ii,iv,v}, {iii,iv,v}, {i,ii,iii,iv}, {i,ii,iii,v}, {i,ii,iv,v}, {i,iii,iv,v}, {ii,iii,iv,v} or {i,ii,iii,iv,v}.

For (i), the length of the polynucleotide may be measured for example by determining the number of interactions between the polynucleotide and the pore or the duration of interaction between the polynucleotide and the pore.

For (ii), the identity of the polynucleotide may be measured in a number of ways. The identity of the polynucleotide may be measured in conjunction with measurement of the sequence of the polynucleotide or without measurement of the sequence of the polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the polynucleotide is modified by methylation, by oxidation, by damage, with one or more proteins or with one or more labels, tags or spacers. Specific modifications will result in specific interactions with the pore which can be measured using the methods described below. For instance, methylcyotsine may be distinguished from cytosine on the basis of the current flowing through the pore during its interaction with each nucleotide.

The methods may be carried out using any apparatus that is suitable for investigating a membrane/pore system in which a pore is present in a membrane. The method may be carried out using any apparatus that is suitable for transmembrane pore sensing. For example, the apparatus comprises a chamber comprising an aqueous solution and a barrier that separates the chamber into two sections. The barrier typically has an aperture in which the membrane containing the pore is formed. Alternatively the barrier forms the membrane in which the pore is present.

The methods may be carried out using the apparatus described in International Application No. PCT/GB08/000562 (WO 2008/102120).

A variety of different types of measurements may be made. This includes without limitation: electrical measurements and optical measurements. A suitable optical method involving the measurement of fluorescence is disclosed by J. Am. Chem. Soc. 2009, 131 1652-1653. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined with electrical measurements (Soni G V et al., Rev Sci Instrum. 2010 January; 81(1):014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO 2000/28312. Alternatively, electrical measurements may be made using a multi-channel system, for example as described in International Application WO 2009/077734 and International Application WO 2011/067559.

The method is preferably carried out with a potential applied across the membrane. The applied potential may be a voltage potential. Alternatively, the applied potential may be a chemical potential. An example of this is using a salt gradient across a membrane, such as an amphiphilic layer. A salt gradient is disclosed in Holden et al., J Am Chem Soc. 2007 Jul. 11; 129(27):8650-5. In some instances, the current passing through the pore as a polynucleotide moves with respect to the pore is used to estimate or determine the sequence of the polynucleotide. This is strand sequencing.

The methods may involve measuring the current passing through the pore as the polynucleotide moves with respect to the pore. Therefore the apparatus may also comprise an electrical circuit capable of applying a potential and measuring an electrical signal across the membrane and pore.

The methods may be carried out using a patch clamp or a voltage clamp. The methods preferably involve the use of a voltage clamp.

The methods of the invention may involve the measuring of a current passing through the pore as the polynucleotide moves with respect to the pore. Suitable conditions for measuring ionic currents through transmembrane protein pores are known in the art and disclosed in the Example. The method is typically carried out with a voltage applied across the membrane and pore. The voltage used is typically from +5 V to −5 V, such as from +4 V to −4 V, +3 V to −3 V or +2 V to −2 V. The voltage used is typically from −600 mV to +600 mV or −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl), caesium chloride (CsCl) or a mixture of potassium ferrocyanide and potassium ferricyanide is typically used. KCl, NaCl and a mixture of potassium ferrocyanide and potassium ferricyanide are preferred. The charge carriers may be asymmetric across the membrane. For instance, the type and/or concentration of the charge carriers may be different on each side of the membrane.

The salt concentration may be at saturation. The salt concentration may be 3 M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is phosphate buffer. Other suitable buffers are HEPES and Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

Molecular Brake

The movement of the concatenated polynucleotide through the pore is preferably controlled by a molecular brake. The molecular brake is preferably bound to the first target polynucleotide before it is contacted with the transmembrane pore and the protein controls the movement of the entire concatenated polynucleotide through the pore. The molecular brake may be attached to a Y adaptor present on the first target polynucleotide as discussed below. The one or more subsequent polynucleotides preferably do not have a molecular brake bound to them before they are attached to the first target polynucleotide.

Any molecular brake may be used including any of those disclosed in International Application No. PCT/GB2014/052737 (published as WO 2015/110777).

The molecular brake is preferably a polynucleotide binding protein. The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

The polynucleotide binding protein is preferably derived from a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the polynucleotide and controlling its movement through the pore. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases, translocases and topoisomerases, such as gyrases. Suitable enzymes include, but are not limited to, exonuclease I from *E. coli* (SEQ ID NO: 11), exonuclease III enzyme from *E. coli* (SEQ ID NO: 13), RecJ from *T. thermophilus* (SEQ ID NO: 15) and bacteriophage lambda exonuclease (SEQ ID NO: 17), TatD exonuclease and variants thereof. Three subunits comprising the sequence shown in SEQ ID NO: 15 or a variant thereof interact to form a trimer exonuclease. The polymerase may be PyroPhage® 3173 DNA Polymerase (which is commercially available from Lucigen® Corporation), SD Polymerase (commercially available from Bioron®) or variants thereof. The enzyme is preferably Phi29 DNA polymerase (SEQ ID NO: 9) or a variant thereof. The topoisomerase is preferably a member of any of the Moiety Classification (EC) groups 5.99.1.2 and 5.99.1.3.

The enzyme is most preferably derived from a helicase. The helicase may be or be derived from a Hel308 helicase, a RecD helicase, such as TraI helicase or a TrwC helicase, a XPD helicase or a Dda helicase. The helicase may be or be derived from Hel308 Mbu (SEQ ID NO: 18), Hel308 Csy (SEQ ID NO: 19), Hel308 Tga (SEQ ID NO: 20), Hel308 Mhu (SEQ ID NO: 21), TraI Eco (SEQ ID NO: 22), XPD Mbu (SEQ ID NO: 23) or a variant thereof.

The helicase may be any of the helicases, modified helicases or helicase constructs disclosed in International Application Nos. PCT/GB2012/052579 (published as WO 2013/057495); PCT/GB2012/053274 (published as WO 2013/098562); PCT/GB2012/053273 (published as WO2013098561); PCT/GB2013/051925 (published as WO 2014/013260); PCT/GB2013/051924 (published as WO 2014/013259); PCT/GB2013/051928 (published as WO 2014/013262) and PCT/GB2014/052736 (published as WO/2015/055981).

The helicase preferably comprises the sequence shown in SEQ ID NO: 25 (Trwc Cba) or as variant thereof, the sequence shown in SEQ ID NO: 18 (Hel308 Mbu) or a variant thereof or the sequence shown in SEQ ID NO: 24 (Dda) or a variant thereof. Variants may differ from the native sequences in any of the ways discussed below for transmembrane pores. A preferred variant of SEQ ID NO: 24 comprises (a) E94C and A360C or (b) E94C, A360C, C109A and C136A and then optionally (ΔM1)G1 (i.e. deletion of M1 and then addition G1). It may also be termed M1G. Any of the variants discussed above may further comprise M1G.

The Dda helicase preferably comprises any of the modifications disclosed in International Application Nos. PCT/GB2014/052736 and PCT/GB2015/052916 (published as WO/2015/055981 and WO 2016/055777).

Any number of helicases may be used in accordance with the invention. For instance, 1, 2, 3, 4, 5, 6, 7, 8, 9, 10 or more helicases may be used. In some embodiments, different numbers of helicases may be used.

The method of the invention preferably comprises contacting the polynucleotide with two or more helicases. The two or more helicases are typically the same helicase. The two or more helicases may be different helicases.

The two or more helicases may be any combination of the helicases mentioned above. The two or more helicases may be two or more Dda helicases. The two or more helicases may be one or more Dda helicases and one or more TrwC helicases. The two or more helicases may be different variants of the same helicase.

The two or more helicases are preferably attached to one another. The two or more helicases are more preferably covalently attached to one another. The helicases may be attached in any order and using any method. Preferred helicase constructs for use in the invention are described in International Application Nos. PCT/GB2013/051925 (published as WO 2014/013260); PCT/GB2013/051924 (published as WO 2014/013259); PCT/GB2013/051928 (published as WO 2014/013262) and PCT/GB2014/052736.

A variant of SEQ ID NO: 9, 11, 13, 15, 17, 18, 19, 20, 21, 22, 23, 24 or 25 is an enzyme that has an amino acid sequence which varies from that of SEQ ID NO: 9, 11, 13, 15, 17, 18, 19, 20, 21, 22, 23, 24 or 25 and which retains polynucleotide binding ability. This can be measured using any method known in the art. For instance, the variant can be contacted with a polynucleotide and its ability to bind to and move along the polynucleotide can be measured. The variant may include modifications that facilitate binding of the polynucleotide and/or facilitate its activity at high salt concentrations and/or room temperature. Variants may be modified such that they bind polynucleotides (i.e. retain polynucleotide binding ability) but do not function as a helicase (i.e. do not move along polynucleotides when provided with all the necessary components to facilitate movement, e.g. ATP and $Mg^{2+}$). Such modifications are known in the art. For instance, modification of the $Mg^{2+}$ binding domain in helicases typically results in variants which do not function as helicases. These types of variants may act as molecular brakes (see below).

Over the entire length of the amino acid sequence of SEQ ID NO: 9, 11, 13, 15, 17, 18, 19, 20, 21, 22, 23, 24 or 25, a variant will preferably be at least 50% homologous to that sequence based on amino acid similarity or identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid similarity or identity to the amino acid sequence of SEQ ID NO: 9, 11, 13, 15, 17, 18, 19, 20, 21, 22, 23, 24 or 25 over the entire sequence. There may be at least 80%, for example at least 85%, 90% or 95%, amino acid similarity or identity over a stretch of 200 or more, for example 230, 250, 270, 280, 300, 400, 500, 600, 700, 800, 900 or 1000 or more, contiguous amino acids ("hard homology"). Homology is determined as described above. The variant may differ from the wild-type sequence in any of the ways discussed above with reference to SEQ ID NO: 2 and 4 above. The enzyme may be covalently attached to the pore. Any method may be used to covalently attach the enzyme to the pore.

A preferred molecular brake is TrwC Cba-Q594A (SEQ ID NO: 25 with the mutation Q594A). This variant does not function as a helicase (i.e. binds polynucleotides but does not move along them when provided with all the necessary components to facilitate movement, e.g. ATP and $Mg^{2+}$).

In strand sequencing, the polynucleotide is translocated through the pore either with or against an applied potential. Exonucleases that act progressively or processively on double stranded polynucleotides can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

Any helicase may be used in the method. Helicases may work in two modes with respect to the pore. First, the method is preferably carried out using a helicase such that it moves the polynucleotide through the pore with the field resulting from the applied voltage. In this mode the 5' end of the polynucleotide is first captured in the pore, and the helicase moves the polynucleotide into the pore such that it is passed through the pore with the field until it finally translocates through to the trans side of the membrane.

Alternatively, the method is preferably carried out such that a helicase moves the polynucleotide through the pore against the field resulting from the applied voltage. In this mode the 3' end of the polynucleotide is first captured in the pore, and the helicase moves the polynucleotide through the pore such that it is pulled out of the pore against the applied field until finally ejected back to the cis side of the membrane.

The method may also be carried out in the opposite direction. The 3' end of the polynucleotide may be first captured in the pore and the helicase may move the polynucleotide into the pore such that it is passed through the pore with the field until it finally translocates through to the trans side of the membrane.

When the helicase is not provided with the necessary components to facilitate movement or is modified to hinder or prevent its movement, it can bind to the polynucleotide and act as a brake slowing the movement of the polynucleotide when it is pulled into the pore by the applied field. In the inactive mode, it does not matter whether the polynucleotide is captured either 3' or 5' down, it is the applied field which pulls the polynucleotide into the pore towards the trans side with the enzyme acting as a brake. When in the inactive mode, the movement control of the polynucleotide by the helicase can be described in a number of ways including ratcheting, sliding and braking. Helicase variants which lack helicase activity can also be used in this way.

The polynucleotide may be contacted with the polynucleotide binding protein and the pore in any order. It is preferred that, when the polynucleotide is contacted with the polynucleotide binding protein, such as a helicase, and the pore, the polynucleotide firstly forms a complex with the protein. When the voltage is applied across the pore, the polynucleotide/protein complex then forms a complex with the pore and controls the movement of the polynucleotide through the pore.

Any steps in the method using a polynucleotide binding protein are typically carried out in the presence of free nucleotides or free nucleotide analogues and an enzyme cofactor that facilitates the action of the polynucleotide binding protein. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the construct to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

The molecular brakes may be any compound or molecule which binds to the polynucleotide and slows the movement of the polynucleotide through the pore. The molecular brake may be any of those discussed above. The molecular brake preferably comprises a compound which binds to the polynucleotide. The compound is preferably a macrocycle.

Suitable macrocycles include, but are not limited to, cyclodextrins, calixarenes, cyclic peptides, crown ethers, cucurbiturils, pillararenes, derivatives thereof or a combination thereof. The cyclodextrin or derivative thereof may be any of those disclosed in Eliseev, A. V., and Schneider, H-J. (1994) *J. Am. Chem. Soc.* 116, 6081-6088. The cyclodextrin is more preferably heptakis-6-amino-β-cyclodextrin ($am_7$-βCD), 6-monodeoxy-6-monoamino-β-cyclodextrin ($am_1$-βCD) or heptakis-(6-deoxy-6-guanidino)-cyclodextrin ($gu_7$-βCD).

Spacers in the Target Polynucleotide

If a helicase is used in the invention, it may be stalled at one or more spacers as discussed in International Application No. PCT/GB2014/050175 (published as WO 2014/135838). Any configuration of one or more helicases and one or more spacers disclosed in the International Application may be used in this invention.

Double Stranded Polynucleotide

If a target polynucleotide is double stranded, the method preferably further comprises providing the target polynucleotide with a hairpin loop at one end of the polynucleotide. The method may comprise linking the two strands of the target polynucleotide at one end with a hairpin loop. The pore and optionally the molecular brake preferably separates the two strands of the target polynucleotide and controls the movement of the target polynucleotide through the pore one strand at a time. Linking and interrogating both strands on a double stranded construct in this way increases the efficiency and accuracy of characterisation.

Suitable hairpin loops can be designed using methods known in the art. The hairpin loop may be any length. The hairpin loop is typically 110 or fewer nucleotides, such as 100 or fewer nucleotides, 90 or fewer nucleotides, 80 or fewer nucleotides, 70 or fewer nucleotides, 60 or fewer nucleotides, 50 or fewer nucleotides, 40 or fewer nucleotides, 30 or fewer nucleotides, 20 or fewer nucleotides or 10 or fewer nucleotides, in length. The hairpin loop is preferably from about 1 to 110, from 2 to 100, from 5 to 80 or from 6 to 50 nucleotides in length. Longer lengths of the hairpin loop, such as from 50 to 110 nucleotides, are preferred if the loop is involved in the differential selectability of the adaptor. Similarly, shorter lengths of the hairpin loop, such as from 1 to 5 nucleotides, are preferred if the loop is not involved in the selectable binding as discussed below.

The hairpin loop may be provided at either end of the polynucleotide, i.e. the 5' or the 3' end. The hairpin loop may be ligated to the polynucleotide using any method known in the art. The hairpin loop may be ligated using a ligase, such as T4 DNA ligase, *E. coli* DNA ligase, Taq DNA ligase, Tma DNA ligase and 9° N DNA ligase.

The two strands of the polynucleotide may be separated using any method known in the art. For instance, they may be separated by a molecular brake, such as a polynucleotide binding protein, or using conditions which favour dehybridsation (examples of conditions which favour dehybridisation include, but are not limited to, high temperature, high pH and the addition of agents that can disrupt hydrogen bonding or base pairing, such as formamide and urea).

The hairpin loop preferably comprises a selectable binding moiety. This allows the polynucleotide to be purified or isolated. A selectable binding moiety is a moiety that can be selected on the basis of its binding properties. Hence, a selectable binding moiety is preferably a moiety that specifically binds to a surface. A selectable binding moiety specifically binds to a surface if it binds to the surface to a much greater degree than any other moiety used in the invention. In preferred embodiments, the moiety binds to a surface to which no other moiety used in the invention binds.

Suitable selective binding moieties are known in the art. Preferred selective binding moieties include, but are not limited to, biotin, a polynucleotide sequence, antibodies, antibody fragments, such as Fab and ScSv, antigens, polynucleotide binding proteins, poly histidine tails and GST tags. The most preferred selective binding moieties are biotin and a selectable polynucleotide sequence. Biotin specifically binds to a surface coated with avidins. Selectable polynucleotide sequences specifically bind (i.e. hybridise) to a surface coated with homologus sequences. Alternatively, selectable polynucleotide sequences specifically bind to a surface coated with polynucleotide binding proteins.

The hairpin loop and/or the selectable binding moiety may comprise a region that can be cut, nicked, cleaved or hydrolysed. Such a region can be designed to allow the polynucleotide to be removed from the surface to which it is bound following purification or isolation. Suitable regions are known in the art. Suitable regions include, but are not limited to, an RNA region, a region comprising desthiobiotin and streptavidin, a disulphide bond and a photocleavable region.

Leader Sequence

The target polynucleotide may be provided with a leader sequence which preferentially threads into the pore or which is capable of selectively attaching to the preceding target polynucleotide. The leader sequence facilitates the method of the invention. The leader sequence may be designed to preferentially thread into the transmembrane pore and thereby facilitate the movement of polynucleotide through the pore. The leader sequence may be designed such that it selectively attaches to the preceding target polynucleotide and facilitates the formation of the concatenated polynucleotide. The leader sequence can also be used to link the polynucleotide to the one or more anchors as discussed above.

The leader sequence typically comprises a polymer. The polymer is preferably negatively charged. The polymer is preferably a polynucleotide, such as DNA or RNA, a modified polynucleotide (such as abasic DNA), PNA, LNA, polyethylene glycol (PEG) or a polypeptide. The leader preferably comprises a polynucleotide and more preferably comprises a single stranded polynucleotide. The leader sequence can comprise any of the polynucleotides discussed above. The single stranded leader sequence most preferably comprises a single strand of DNA, such as a poly dT section. The leader sequence preferably comprises the one or more spacers.

The leader sequence can be any length, but is typically 10 to 150 nucleotides in length, such as from 20 to 150 nucleotides in length. The length of the leader typically depends on the transmembrane pore used in the method.

The leader sequence in a subsequent target polynucleotide typically comprises the part which hybridizes to the part in the preceding target polynucleotide. The leader sequence preferably comprises one part of the click chemistry, such as a click reactive group.

Y Adaptors

A double stranded target polynucleotide may be provided with adaptors at one or both ends. A double stranded target polynucleotide may be provided with a Y adaptor at both ends.

A double stranded target polynucleotide may be provided with a Y adaptor at one end and a hairpin loop at the other end. A method of characterising a polynucleotide may comprise attaching a Y adaptor to one end of a double stranded target polynucleotide and attaching a hairpin loop at the other end. The Y adaptor and/or the hairpin adaptor are typically polynucleotide adaptors. They may be formed from any of the polynucleotides discussed above.

The Y adaptor typically comprises (a) a double stranded region and (b) a single stranded region or a region that is not complementary at the other end. The Y adaptor may be described as having an overhang if it comprises a single stranded region. The presence of a non-complementary region in the Y adaptor gives the adaptor its Y shape since the two strands typically do not hybridise to each other unlike the double stranded portion. In other words, the Y adaptor comprises two polynucleotide strands, e.g. DNA strands. A portion extending to the 3' end of the first strand is complementary to a portion extending to the 5' end of the other strand. The complementary portions hybridise to each other and form a duplex, or double stranded region of the Y adaptor. The remaining portions of the first and second strands are not complementary and do not hybridise to one another.

In one embodiment, the Y adaptor comprises one or more attachment sites that can be used to selectively attach a first (preceding) target polynucleotide to a second (subsequent) target polynucleotide as described herein.

In one embodiment, a first attachment site is present in the double stranded region of the Y adaptor. When the Y adaptor is ligated to the end of a target polynucleotide, the attachment site in the double stranded region is "hidden" until the target polynucleotide interacts with a pore. This "hidden" attachment site corresponds to the part of the first (preceding) target polynucleotide that can be selectively attached to a part of the second (subsequent) target polynucleotide.

In one embodiment, a second attachment site is present in the single stranded region of the Y adaptor. When the Y adaptor is ligated to the end of a second target polynucleotide, the attachment site in the single stranded region is available to bind to a first attachment site in a first target polynucleotide when the first target polynucleotide interacts with a pore to reveal the first attachment site. This "exposed" attachment site corresponds to the part of the second (subsequent) target polynucleotide that can be selectively attached to a part of the first (preceding) target polynucleotide.

A Y adaptor may comprise a first attachment site and a second attachment site as described above. In one embodiment, the first and second attachment sites present in a Y adaptor are not complementary to each other. A population of different Y adaptors, wherein complementary attachment sites are present in different Y adaptors, may then be used to perform a method as described herein. In an example of this embodiment, the first (hidden) attachment site and the second (exposed) attachment site in a first Y adaptor may both have the same sequence, which sequence is complementary to the sequence of a first (hidden) attachment site and a second (exposed) attachment site in a second Y adaptor. The first and second Y adaptors may then be used together, wherein a first (preceding) target polynucleotide comprising the first Y adaptor is concatenated to a second (subsequent) target polynucleotide that comprises the second Y adaptor. In another embodiment, the first and second attachment sites present in a Y adaptor are complementary to each other. In this embodiment, a single type of Y adaptor may be used.

The invention provides a Y adaptor comprising a first polynucleotide strand and a second polynucleotide strand, wherein: (i) a portion extending to the 3' end of the first polynucleotide strand is complementary to a portion extending to the 5' end of the second polynucleotide strand and the complementary portions form a duplex; (ii) a portion extending to the 5' end of the first polynucleotide strand and a portion extending to the 3' end of the second polynucleotide strand do not hybridise to one another; and (iii) the portion extending to the 5' end of the second polynucleotide strand comprises a sequence that is capable, when the duplex is unwound, of hybridising to a sequence comprised in the a portion extending to the 5' end of the first polynucleotide strand.

The sequence in the portion extending to the 5' end of the second polynucleotide strand and the sequence comprised in the a portion extending to the 5' end of the first polynucleotide strand that are capable of hybridising to each other preferably have a length of from 6 to 50 base pairs, such as from 7 to 40, 8 to 30, 9 to 20 or 10 to 15 base pairs.

The invention also provides a Y adaptor comprising a first polynucleotide strand and a second polynucleotide strand, wherein: (i) a portion extending to the 3' end of the first polynucleotide strand is complementary to a portion extending to the 5' end of the second polynucleotide strand and the complementary portions form a duplex; (ii) a portion extending to the 5' end of the first polynucleotide strand and a portion extending to the 3' end of the second polynucleotide strand do not hybridise to one another; and (iii) the portion extending to the 5' end of the second polynucleotide strand comprises a sequence that is identical to a sequence comprised in the a portion extending to the 5' end of the first polynucleotide strand.

The sequence in the portion extending to the 5' end of the second polynucleotide strand that is identical to the sequence comprised in the a portion extending to the 5' end of the first polynucleotide strand preferably has a length of from 6 to 50 base pairs, such as from 7 to 40, 8 to 30, 9 to 20 or 10 to 15 base pairs.

The duplex region in the Y adaptor may have a length of from about 6 to 200 base pairs, such as from 10 to 150, 20 to 175, 25 to 150, 50 to 125 or 75 to 100 base pairs. The duplex region may comprise a blocker sequence to prevent movement of a helicase along the duplex strand. In one embodiment, the blocker comprises iSp18. Suitable blocker sequences are described in the Examples.

In the Y adaptor, the portion extending to the 5' end of the first polynucleotide strand is preferably from 10 to 100 base pairs in length, such as from 10 to 75, 20 to 65 or 25 to 50 base pairs in length. The portion extending to the 5' end of the first polynucleotide strand comprises an exposed attachment site. The portion extending to the 5' end of the first polynucleotide strand preferably comprises a polymer leader sequence. The polymer is preferably negatively charged. The polymer is preferably a polynucleotide, such as DNA or RNA, a modified polynucleotide (such as abasic DNA), PNA, LNA, polyethylene glycol (PEG) or a polypeptide. The leader sequence preferably comprises one or more spacers, such as iSpC3. Examples of suitable leader sequences are described in the Examples.

The leader sequence can be any length, but is typically 10 to 150 nucleotides in length, such as from 20 to 150, 25 to 100 or 30 to 50 nucleotides in length. The length of the leader typically depends on the transmembrane pore used in the method. In one embodiment the combined length of the leader sequence and the exposed attachment site, which may comprise all or part of the leader sequence is from 25 to 40, such as 30 base pairs.

In one embodiment, the 5' end of the first polynucleotide strand of the adaptor comprises comprises a first part of the click chemistry, such as a click reactive group.

In one embodiment, the 3' end of the second polynucleotide strand of the adaptor comprises comprises a second part of the click chemistry, such as a click reactive group. The first part of the click chemistry is a part that reacts with the second part of the click chemistry. Typically, in this embodiment, the portion extending to the 5' end of the second polynucleotide strand comprises a sequence that is capable, when the duplex is unwound, of hybridising to a sequence comprised in the a portion extending to the 5' end of the first polynucleotide strand.

In another embodiment, the 3' end of the second polynucleotide strand of the adaptor comprises comprises a first part of the click chemistry, such as a click reactive group. In this embodiment the adaptor is designed for use together with a second Y adaptor which comprises a second part of the click chemistry, such as a click reactive group at the 5' end of its first polynucleotide strand and a second part of the click chemistry, such as a click reactive group at the 3' end of its second polynucleotide strand. Typically, in this embodiment, the portion extending to the 5' end of the second polynucleotide strand comprises a sequence that is identical to a sequence comprised in the a portion extending to the 5' end of the first polynucleotide strand.

In one embodiment, the 5' end of the first polynucleotide strand of the adaptor comprises a phosphatase. The phosphatase may facilitate ligation of the 5' end of the first polynucleotide strand to the 3' end of another polynucleotide strand (typically the 3' end of the second strand of a second adaptor after exposure of the hidden attachment site in the second adaptor).

The Y adaptor may comprise one or more anchors. Anchors are discussed in more detail above. In one embodiment, the Y adaptor preferably comprises an anchor attached to a third polynucleotide strand which comprises a 5' region that hybridises to the first polynucleotide strand. The part of the first polynucleotide strand to which the third polynucleotide strand binds is typically between the region of the first polynucleotide strand that hybridises to the second polynucleotide strand and the leader sequence. The anchor is preferably attached at or close to the 3' end of the third polynucleotide strand. A fourth polynucleotide strand may be hybridized to a region of the third polynucleotide strand that is not hybridised to the first polynucleotide strand. The anchor is preferably cholesterol.

One part of the non-complementary region in the second strand of each Y adaptor preferably forms a loop structure. This facilitates the method of invention as discussed above. In particular it facilitates the action of ligases that join double stranded polynucleotides. In this embodiment, the two sides of the loop typically hybridise to one another. The nucleotide base at the 3' end of the second polynucleotide strand is preferably at the end of the loop. The nucleotide base at the 3' end of the second polynucleotide strand is typically hybridised to another part of the second polynucleotide strand. The first (hidden) attachment site is preferably adjacent to, but not part of the loop structure. Hybridisation of the first (hidden) attachment site to the second (exposed) attachment site in a different Y adaptor elongates the loop.

The Y adaptors, which are at the ends of target polynucleotides, can then be joined, for example by ligation (using a ligase) or by click chemistry. This embodiment results in the two adaptors (and hence the preceding and subsequent target polynucleotides) being attached by a loop which may dehybridise and move through the pore.

The loop in the second polynucleotide strand may be any length. The loop in the second polynucleotide strand preferably comprises 10 to 50 nucleotides, such as from 15 to 40, or 20 to 25, for example 23 nucleotides.

The Y adaptor preferably comprises a leader sequence which preferentially threads into the pore. Leader sequences are discussed above. In one embodiment a second (exposed) attachment site is present in the same strand of the Y adaptor as a leader sequence. Typically, the leader sequence is at the 5' end of the Y adaptor and the second attachment site is present between the leader sequence and the double stranded region. The exposed attachment site may form part of the leader sequence.

The Y adaptor may further comprise one or more polynucleotide binding proteins. In one embodiment a polynucleotide binding protein is attached to the first polynucleotide strand of the Y adaptor. The polynucleotide binding protein is preferably located 3' of the leader sequence and 5' to the blocker sequence. The polynucleotide binding protein is preferably a helicase. More than one, such as two or more polynucleotide binding proteins, preferably two or more helicases, may be comprised in the adaptor. The two or more polynucleotide binding proteins are preferably different from one another, for example are two different helicases. Where two polynucleotide binding proteins are present, the two proteins preferably process the bound polynucleotide at different rates once the effect of the blocker sequence is removed. For example, a first polynucleotide binding protein, preferably a first helicase, may be attached to the first polynucleotide strand of the adaptor 3' to a second polynucleotide binding protein, preferably a second helicase. In this example, the first polynucleotide binding protein may separate the two strands of a double stranded target polynucleotide and the second polynucleotide binding protein may act to control movement of the target polynucleotide through a nanopore. In this embodiment, the first polynucleotide binding protein may be referred to as a "release protein" and the second polynucleotide binding protein as a "motor protein". The release protein preferably moves along the polynucleotide faster than the motor protein.

The Y adaptor preferably comprises a selectable binding moiety as discussed above. The Y adaptor and/or the selectable binding moiety may comprise a region that can be cut, nicked, cleaved or hydrolysed as discussed above.

The Y adaptor and/or the hairpin loop may be ligated to the polynucleotide using any method known in the art. One or both of the adaptors may be ligated using a ligase, such as T4 DNA ligase, *E. coli* DNA ligase, Taq DNA ligase, Tma DNA ligase and 9° N DNA ligase. Alternatively, the adaptors may be added to the polynucleotide using the methods of the invention discussed below.

In a preferred embodiment, the method comprises modifying the double stranded polynucleotide so that it comprises adaptors at its ends. For example, in one embodiment, the method comprises modifying the double stranded polynucleotide so that it comprises the Y adaptor at one end and the hairpin loop at the other end. In another embodiment, the method comprises modifying the double stranded polynucleotide so that it comprises a Y adaptor at each end. Any manner of modification can be used. The method preferably comprises modifying the double stranded polynucleotide in accordance with the invention. This is discussed in more detail below. The methods of modification and characterisation may be combined in any way.

Adding Hairpin Loops and Leader Sequences

The double stranded polynucleotide may be provided with Y adaptors and hairpin loops by contacting the polynucleotide with a MuA transposase and a population of double stranded MuA substrates, wherein a proportion of the substrates in the population are Y adaptors comprising the leader sequence and wherein a proportion of the substrates in the population are hairpin loops. The transposase fragments the double stranded polynucleotide and ligates MuA substrates to one or both ends of the fragments. This produces a plurality of modified double stranded polynucleotides comprising the leader sequence at one end and the hairpin loop at the other. The modified double stranded polynucleotides may then be investigated using the method of the invention.

These MuA based methods are disclosed in International Application No. PCT/GB2014/052505 published as (WO 2015/022544). They are also discussed in detail in International Application No PCT/GB2015/050991.

The double stranded polynucleotide may be provided with Y adaptors by contacting the polynucleotide with a MuA transposase and a population of double stranded MuA substrates, wherein the substrates are Y adaptors comprising a leader sequence and attachment sites. The transposase fragments the double stranded polynucleotide and ligates MuA substrates to one or both ends of the fragments. This produces a plurality of modified double stranded target polynucleotides comprising single stranded overhangs at both ends. The modified double stranded polynucleotides may then be investigated using the method of the invention.

Modified Polynucleotide Analytes

Before characterisation, the polynucleotide may be modified by contacting the polynucleotide with a polymerase and a population of free nucleotides under conditions in which the polymerase forms a modified polynucleotide using the polynucleotide as a template, wherein the polymerase replaces one or more of the nucleotide species in the polynucleotide with a different nucleotide species when forming the modified polynucleotide analyte. The modified polynucleotide may then be characterised in accordance with the invention. This type of modification is described in PCT Application No. PCT/GB2015/050483. Any of the polymerases discussed above may be used. The polymerase is preferably Klenow or 9° North.

Population of Y Adaptors

The invention also provides a population of two or more polynucleotide Y adaptors, wherein each adaptor comprises first and second parts (first and second attachment sites) which are capable of hybridising together and wherein each first part (first attachment site) is initially protected from hybridisation to the second part (second attachment site). The population may comprise any number of adaptors, such as the numbers discussed above for target polynucleotide.

Also provided is a population of polynucleotide adaptors comprising a first polynucleotide adaptor and a second polynucleotide adaptor, wherein the first polynucleotide adaptor and the second polynucleotide adaptor each comprise a first polynucleotide strand and a second polynucleotide strand, wherein: (a)(i) a portion extending to the 3' end of the first polynucleotide strand is complementary to a portion extending to the 5' end of the second polynucleotide strand and the complementary portions form a duplex; (ii) a portion extending to the 5' end of the first polynucleotide strand and a portion extending to the 3' end of the second polynucleotide strand do not hybridise to one another; and wherein (b) the portion extending to the 5' end of the second polynucleotide strand of the first polynucleotide adaptor comprises a sequence that is capable, when the duplex is unwound, of hybridising to a sequence comprised in the portion extending to the 5' end of the first polynucleotide strand of the second polynucleotide adaptor. These polynucleotide adaptors are referred to a "Y adaptors" because of their shape.

The Y adaptors in the population may have any of the features described in the section "Y adaptors" above. Any of the embodiments discussed above with reference to the methods of the invention equally apply to the population of the invention.

As discussed above, each Y adaptor typically comprises (a) a double stranded region and (b) a single stranded region or a region that is not complementary at the other end. The presence of the non-complementary region in the Y adaptor gives the adaptor its Y shape since the two part/strands typically do not hybridise to each other unlike the double stranded portion.

In other words, the Y adaptor comprises two polynucleotide strands, e.g. DNA strands. A portion extending to the 3' end of the first strand is complementary to a portion extending to the 5' end of the other strand. The complementary portions hybridise to each other and form a duplex, or double stranded region of the Y adaptor. The remaining portions of the first and second strands are not complementary and do not hybridise to one another.

In one embodiment, the Y adaptor comprises one or more attachment sites that can be used to selectively attach a first (preceding) target polynucleotide to a second (subsequent) target polynucleotide as described herein.

In one embodiment, a first attachment site is present in the double stranded region of the Y adaptor. When the Y adaptor is ligated to the end of a target polynucleotide, the attachment site in the double stranded region is "hidden" until the target polynucleotide interacts with a pore. This "hidden" attachment site corresponds to the part of the first (preceding) target polynucleotide that can be selectively attached to a part of the second (subsequent) target polynucleotide.

In one embodiment, a second attachment site is present in the single stranded region of the Y adaptor. When the Y adaptor is ligated to the end of a second target polynucleotide, the attachment site in the single stranded region is available to bind to a first attachment site in a first target polynucleotide when the first target polynucleotide interacts with a pore to reveal the first attachment site. This "exposed" attachment site corresponds to the part of the second (subsequent) target polynucleotide that can be selectively attached to a part of the first (preceding) target polynucleotide.

A Y adaptor may comprise a first attachment site and a second attachment site as described above. In one embodiment, the first and second attachment sites present in a Y adaptor are not complementary to each other. A population of different Y adaptors, wherein complementary attachment sites are present in different Y adaptors, may then be used to perform a method as described herein. In another embodiment, the first and second attachment sites present in a Y adaptor are complementary to each other. In this embodiment, a single type of Y adaptor may be used.

The Y adaptor may comprise one or more anchors. Anchors are discussed in more detail above. In one embodiment, the Y adaptor preferably comprises an anchor attached to the portion extending to the 3' end of the second polynucleotide strand.

The first part (first attachment site) is preferably initially protected by hybridisation to the opposite strand in the double stranded region of the Y adaptor.

One half of the non-complementary region in each Y adaptor preferably forms a loop structure. This facilitates the method of invention as discussed above. The first part (is preferably adjacent to, but not part of the loop structure. Hybridisation of the first part to the second part in a different Y adaptor elongates the loop. This embodiment results in the two adaptors (and hence the preceding and subsequent target polynucleotides) being attached by a loop which may dehybridise and move through the pore.

Each Y adaptor preferably further comprises a leader sequence comprising the second part. Suitable leader sequences are discussed above. The second part is preferably an overhang formed by a bridging polynucleotide hybridised to the free end of the leader sequence. The bridging polynucleotide may be any length and formed from any of the types of polynucleotide discussed above. In one embodiment the second (exposed) attachment site is present in the same strand of the Y adaptor as a leader sequence. Typically, the leader sequence is at the 5' end of the Y adaptor and the second attachment site is present between the leader sequence and the double stranded region.

In a preferred embodiment, only one of the adaptors in the population comprises a molecular brake. Attachment of this adaptor to the first target polynucleotide means that the molecular brake will control the movement of the concatenated polynucleotide, i.e. all of the target polynucleotides, through the pore.

The first part preferably comprises a click reactive group and the second part comprises the complementary click reactive group. The reactive groups may be any of those discussed above.

Kits

The present invention also provides a kit for characterising two or more double stranded target polynucleotides. In one embodiment, the kit comprises a population of Y adaptors of the invention. In a further embodiment, the kit comprises a Y adaptor of the invention. In another embodiment, the kit comprises a population of Y adaptors of the invention and a population of hairpin loops. Such loops are discussed above.

The kit may further comprise a microparticle for delivering the target polynucleotides to a transmembrane pore in a membrane. The kit may further comprise one or more anchors which are capable of coupling the polynucleotides to a membrane. The microparticle and the one or more anchors may be any of those discussed above with reference to the method of the invention. The microparticle is preferably part of the kit for extracting and/or purifying the polynucleotide.

Any of the embodiments discussed above with reference to the method of the invention equally apply to the kits. The kit may further comprise the components of a membrane, such as the components of an amphiphilic layer or a triblock copolymer membrane. The kit may further comprise a transmembrane protein pore.

The kit of the invention may additionally comprise one or more other reagents or instruments which enable any of the embodiments mentioned above to be carried out. The kit may comprise a magnet or an electromagnet. Such reagents or instruments include one or more of the following: suitable buffer(s) (aqueous solutions), means to obtain a sample from a subject (such as a vessel or an instrument comprising a needle), means to amplify and/or express polynucleotides, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding for which organism the method may be used.

The following Examples illustrate the invention.

EXAMPLES

Example 1

This example describes a method of characterising a concatenated polynucleotide where the method of attachment used to join the polynucleotides together is by ligation.

Materials and Methods

Ligation Prep

A leader strand (ID 1 below), a bottom strand (ID NO: 2 below), containing a 3' hairpin, and a blocker strand (ID No: 3 below) were annealed at 5 μM, 6 μM and 6 μM respectively in 50 mM HEPES pH 8, 100 mM potassium acetate from 95° C. to 22° C. at 2° C. per minute. The hybridised DNA was known as adapter 1.

An aliquot of T4 Dda-(E94C/F98W/C109A/C136A/A360C) (SEQ ID NO: 24 with mutations E94C/F98W/C109A/C136A/A360C and then (ΔM1)G1G2 (where (ΔM1)G1G2=deletion of M1 and then addition G1 and G2) was thawed on ice before 50 ul was buffer exchanged into 50 mM HEPES pH 8, 100 mM potassium acetate, 2 mM EDTA through a 0.5 ml Zeba column, according to the manufacturer's instructions. The recovered protein was quantified using the A280 nm value and adjusted to 0.25 mg $ml^{-1}$ using the same buffer. 27 ul of buffer exchanged protein was mixed with 3 ul of adapter 1 in a DNA low bind eppendorf and left to incubate for 10 mins at 35° C. 0.37 ul of 8.1 mM TMAD was then added and the sample was left to incubate for 60 mins at 35° C. 30 ul of 50 mM HEPES pH 8, 1 M NaCl, 2 mM MgCl2, 2 mM rATP was then added and left for a further 20 mins at room temperature.

222 ul of Agencourt AMPure beads (Beckman Coulter) were then added and the sample incubated for 5 mins at room temperature on a rotator. The beads were pelleted on a magnetic rack and the supernatant removed. While still on the magnetic rack the beads were washed with 500 ul of 50 mM Tris pH 7.5, 2.5 M NaCl, 20% PEG 8,000, turning through 360° to bathe the pellet on the rack. The wash buffer was removed and the pellet pulsed briefly in a centrifuge before returning to the magnetic rack to remove the last remnants of solution. The pellet was then resuspended in 30 ul of 50 mM Tris pH 7.5, 20 mM NaCl for 5 mins at room temperature before being placed on a magnetic rack to recover the purified adapter which was known as preloaded Y-adapter 1.

500 ng of end-repaired and dA-tailed *E. coli* genomic DNA was ligated for 10 mins at room temperature in 50 ul with 5 ul of 200 nM preloaded Y-adapter 1 from above and 1 ul of 1 μM HP-adapter (ID NO: 4), in 1× Blunt/TA master mix (NEB). After incubation 0.5 ul of 5 μM hairpin tether (ID NO: 6) was added and the sample left for a further 10 mins at room temperature.

25 ul of MyOne C1 Streptavidin beads (Invitrogen) were bound to a magnetic rack and the supernatant was removed. The pellet was then washed 3× by resuspension in 200 ul of 10 mM Tris pH 7.5, 2 M NaCl, 0.1 mM EDTA. Finally the beads were resuspended in 50 ul of 10 mM Tris pH 7.5, 2 M NaCl, 0.1 mM EDTA. The beads were then added to the ligation mix and incubated on a rotator for 10 mins at room temperature. The bead bound library was then added to a magnetic rack and the supernatant was removed. The pellet was then washed 3× by resuspension in 200 ul of 10 mM Tris pH 7.5, 2 M NaCl, 0.1 mM EDTA. Finally the beads were resuspended in 12.5 ul of 40 mM CAPS pH 10, 40 mM KCl, 5 mM Biotin, 0.1 mM EDTA and 400 nM of tether (ID NO: 5). The sample was incubated for 10 mins at 37° C. before the beads were pelleted and the library containing the supernatant was removed.

Electrical measurements were acquired from single MspA nanopores inserted in block co-polymer in buffer (25 mM K Phosphate buffer, 150 mM Potassium Ferrocyanide (II), 150 mM Potassium Ferricyanide (III), pH 8.0). After achieving a single pore inserted in the block co-polymer, then buffer (2 mL, 25 mM K Phosphate buffer, 150 mM Potassium Ferrocyanide (II), 150 mM Potassium Ferricyanide (III), pH 8.0) was flowed through the system to remove any excess MspA nanopores. 500 ul of 25 mM potassium phosphate buffer pH 8, 500 mM KCl, 2 mM MgCl2 and 2 mM rATP, with 10 mins between each wash. 12 ul of the recovered bead purified library was added to 150 ul of 50 mM potassium phosphate buffer pH 8, 1 M KCl, 8 ul of 75 mM MgCl2, 75 mM rATP, 124 ul of nuclease free water and 6 ul of T3 DNA ligase (NEB). 150 ul of this sequencing mix was then added to the nanopore system. The experiment was run at −140 mV and helicase-controlled DNA movement monitored.

```
ID NO: 1
/5Phos/GCGGTTGTT/iSpC3//iSpC3//iSpC3//iSpC3//
iSpC3//iSpC3//iSpC3//iSpC3//iSpC3//iSpC3//iSpC3//
iSpC3//iSpC3//iSpC3//iSpC3//iSpC3//iSpC3//iSpC3//
iSpC3//iSpC3//iSpC3/(SEQ ID NO: 28)/iSp18//iSp18//
iSp18//iSp18/(SEQ ID NO: 29)

ID NO: 2
/5Phos/(SEQ ID NO: 30)/iSp18//iSp18//iSp18/(SEQ ID
NO: 31)/iSp18//iSp18//iSp18/(SEQ ID NO: 32)

ID NO: 3
/5BNA-G//iBNA-G//iBNA-T//iBNA-T//iBNA-A/(SEQ ID NO:
33)

ID NO: 4
/5Phos/(SEQ ID NO: 34)/iSp18//iSp18//iSp18/(SEQ ID
NO: 35)/iSp18//iSp18//iSp18/(SEQ ID NO: 36)

ID NO: 5
/5CholTEG/(SEQ ID NO: 37)

ID NO: 6
/5desthiobiotinTEG/TT/iSp18//iSp18//iSp18//iSp18//
iSp18//iSp18/(SEQ ID NO: 38)/iSp18//iSp18//iSp18//
iSp18//iSp18//iSp18/TT/3CholTEG
```

Results

The helicase T4 Dda-(E94C/F98W/C109A/C136A/A360C) was used to control the movement of the concatenated polynucleotide through the MspA nanopore. FIGS. 2-6 each show a current trace (top trace on each slide) of a concatenated polynucleotide (a first polynucleotide attached to one subsequent polynucleotide) as it translocated through the nanopore. The lower trace of FIGS. 2-6 show zoomed in regions 1-5 of the upper trace. The lower traces show translocation of spacer groups (found in the leader and hairpin regions of the first and subsequent polynucleotide and marked with a *) through the nanopore. The spacer groups allowed more current to flow through the nanopore as they translocated through it. The example trace shows that the first polynucleotide was successfully ligated to the subsequent polynucleotide.

Example 2

Figure 7:
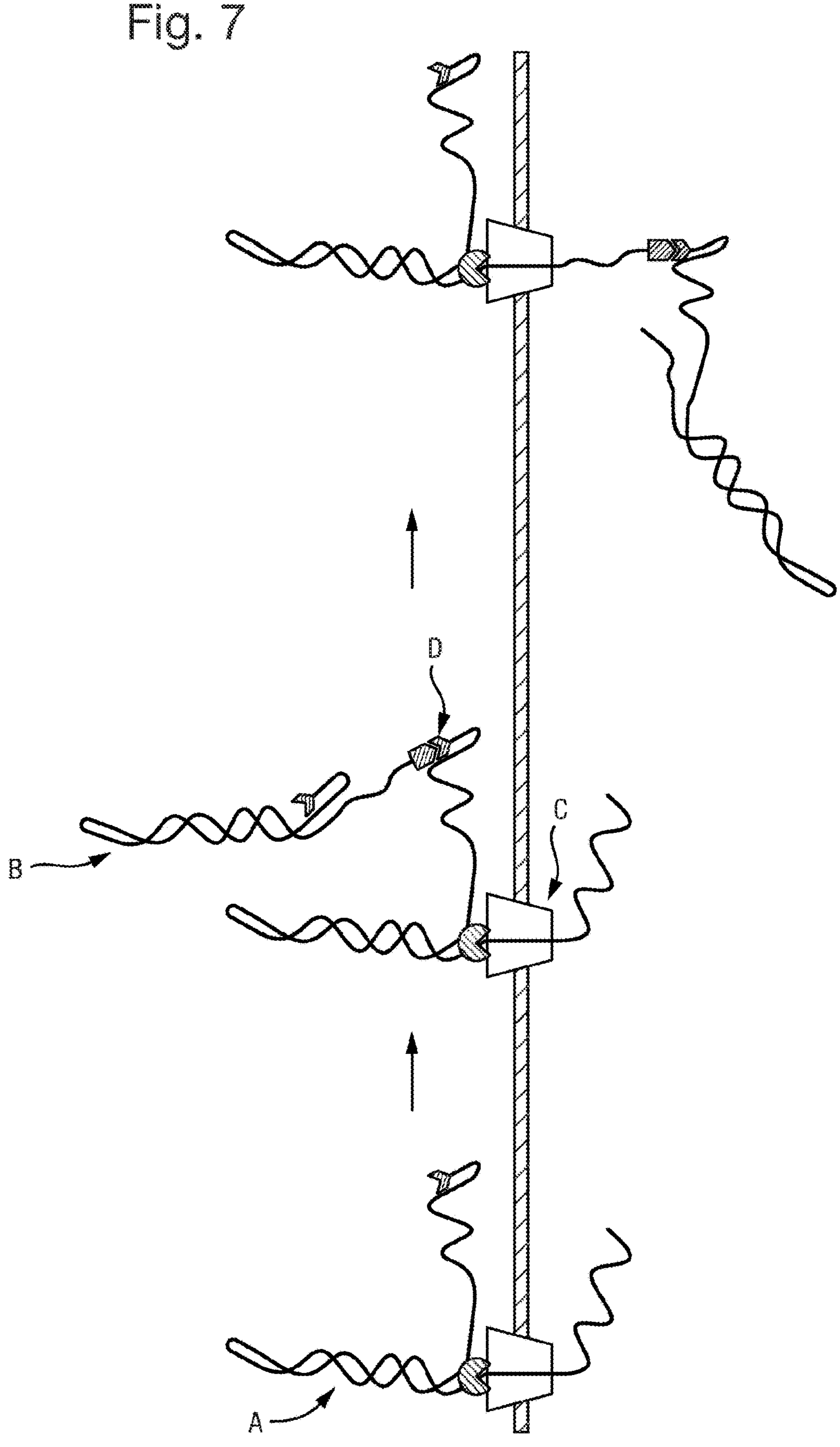
FIG. 7 shows the attachment of a subsequent target polynucleotide (labelled B) to the first target polynucleotide (labelled A) using click chemistry (see click chemistry linkage labelled D) to produce a concatenated polynucleotide. The attachment point in the first target polynucleotide was revealed for attachment as the first polynucleotide moved through the pore (labelled C).

This example describes a method of characterising a concatenated polynucleotide where the method of attachment used to join the polynucleotides together is by click chemistry (see FIG. 7 for a cartoon representation of attachment using click chemistry).

Materials and Methods

Click Ligation Prep:

A leader strand (ID NO: 7) and a blocker strand (ID NO: 8), containing a tether hybridisation site, were annealed at 5.5 μM and 6 μM respectively in 50 mM HEPES pH 8, 100 mM potassium acetate from 95° C. to 22° C. at 2° C. per minute. 10 μM of a bottom strand (ID NO: 9), containing a 3' hairpin, was heated to 95° C. for 1 min before being snap cooled on ice in 50 mM HEPES pH 8, 100 mM potassium acetate. The two samples were equilibrated to 50° C. before being mixed 1:1 and left at 40° C. for 1 min before snap cooling on ice. The hybridised DNA was known as adapter 2.

An aliquot of T4 Dda-(E94C/F98W/C109A/C136A/A360C) (SEQ ID NO: 24 with mutations E94C/F98W/C109A/C136A/A360C and then (ΔM1)G1G2 (where (ΔM1)G1G2=deletion of M1 and then addition G1 and G2) was thawed on ice before 50 ul was buffer exchanged into 50 mM HEPES pH 8, 100 mM potassium acetate, 2 mM EDTA through a 0.5 ml Zeba column, according to the manufacturer's instructions. The recovered protein was quantified using the A280 nm value and adjusted to 0.25 mg $ml^{-1}$ using the same buffer.

27 ul of buffer exchanged protein was mixed with 3 ul of adapter 2 in a DNA low bind eppendorf and left to incubate for 10 mins at 35° C. 0.37 ul of 8.1 mM TMAD was then added and the sample was left to incubate for 60 mins at 35° C. 30 ul of 50 mM HEPES pH 8, 1 M NaCl, 2 mM MgCl2, 2 mM rATP was then added and left for a further 20 mins at room temperature.

222 ul of Agencourt AMPure beads (Beckman Coulter) were added and the sample incubated for 5 mins at room temperature on a rotator. The beads were pelleted on a magnetic rack and the supernatant removed. While still on the magnetic rack the beads were washed with 500 ul of 50 mM Tris pH 7.5, 2.5 M NaCl, 20% PEG 8,000, turning through 3600 to bathe the pellet on the rack. The wash buffer was removed and the pellet pulsed briefly in a centrifuge before returning to the magnetic rack to remove the last remnants of solution. The pellet was resuspended in 30 ul of 50 mM Tris pH 7.5, 20 mM NaCl for 5 mins at room temperature before being placed on a magnetic rack to recover the purified adapter which was known as preloaded Y-adapter 2.

500 ng of end-repaired and dA-tailed *E. coli* genomic DNA was ligated for 10 mins at room temperature in 50 ul with 5 ul of 200 nM preloaded Y-adapter 2 from above and 1 ul of 1 uM HP-adapter (ID NO: 4), in 1× Blunt/TA master mix (NEB). After incubation 0.5 ul of 5 μM hairpin tether (ID NO: 6) was added and the sample left for a further 10 mins at room temperature.

25 ul of MyOne C1 Streptavidin beads (Invitrogen) were bound to a magnetic rack and supernatant was removed. The pellet was then washed 3× by resuspension in 200 ul of 10 mM Tris pH 7.5, 2 M NaCl, 0.1 mM EDTA. Finally the beads were resuspended in 50 ul of 10 mM Tris pH 7.5, 2 M NaCl, 0.1 mM EDTA. The beads were then added to the ligation mix and incubated on a rotator for 10 mins at room temperature. The bead bound library was then added to a magnetic rack and supernatant was removed. The pellet was then washed 3× by resuspension in 200 ul of 10 mM Tris pH 7.5, 2 M NaCl, 0.1 mM EDTA. Finally the beads were resuspended in 12.5 ul of 40 mM CAPS pH 10, 40 mM KCl, 5 mM Biotin, 0.1 mM EDTA and 400 nM of tether (ID NO: 5). The sample was incubated for 10 mins at 37° C. before the beads pelleted and the library containing supernatant was removed.

Electrical measurements were acquired from single MspA nanopores inserted in block co-polymer in buffer (25 mM K Phosphate buffer, 150 mM Potassium Ferrocyanide (II), 150 mM Potassium Ferricyanide (III), pH 8.0). After achieving a single pore inserted in the block co-polymer, then buffer (2 mL, 25 mM K Phosphate buffer, 150 mM Potassium Ferrocyanide (II), 150 mM Potassium Ferricyanide (III), pH 8.0) was flowed through the system to remove any excess MspA nanopores. 500 ul of 25 mM potassium phosphate buffer pH 8, 500 mM KCl, 2 mM MgCl2 and 2 mM rATP, with 10 mins between each wash. 12 ul of the recovered bead purified library was added to 150 ul of 50 mM potassium phosphate buffer pH 8, 1 M KCl, 8 ul of 75 mM MgCl2, 75 mM rATP and 130 ul of nuclease free water. 150 ul of this sequencing mix was then added to the nanopore system. The experiment was run at −140 mV and helicase-controlled DNA movement monitored.

```
                                            SEQ ID NO: 7
/Azide/(SEQ ID NO: 39)/iSpC3//iSpC3//iSpC3//

iSpC3//iSpC3//iSpC3//iSpC3//iSpC3//iSpC3//

iSpC3//iSpC3//iSpC3//iSpC3//iSpC3//iSpC3//

iSpC3//iSpC3//iSpC3//iSpC3//iSpC3//iSpC3/

(SEQ ID NO: 28)/iSp18//iSp18//iSp18//iSp18/

(SEQ ID NO: 29)

                                            SEQ ID NO: 8
SEQ ID NO: 40

                                            SEQ ID NO: 9
/5Phos/(SEQ ID NO: 41)/iSp18//iSp18//iSp18//

iSp18/(SEQ ID NO: 32)/DBCO/
```

Results

Figure 8:
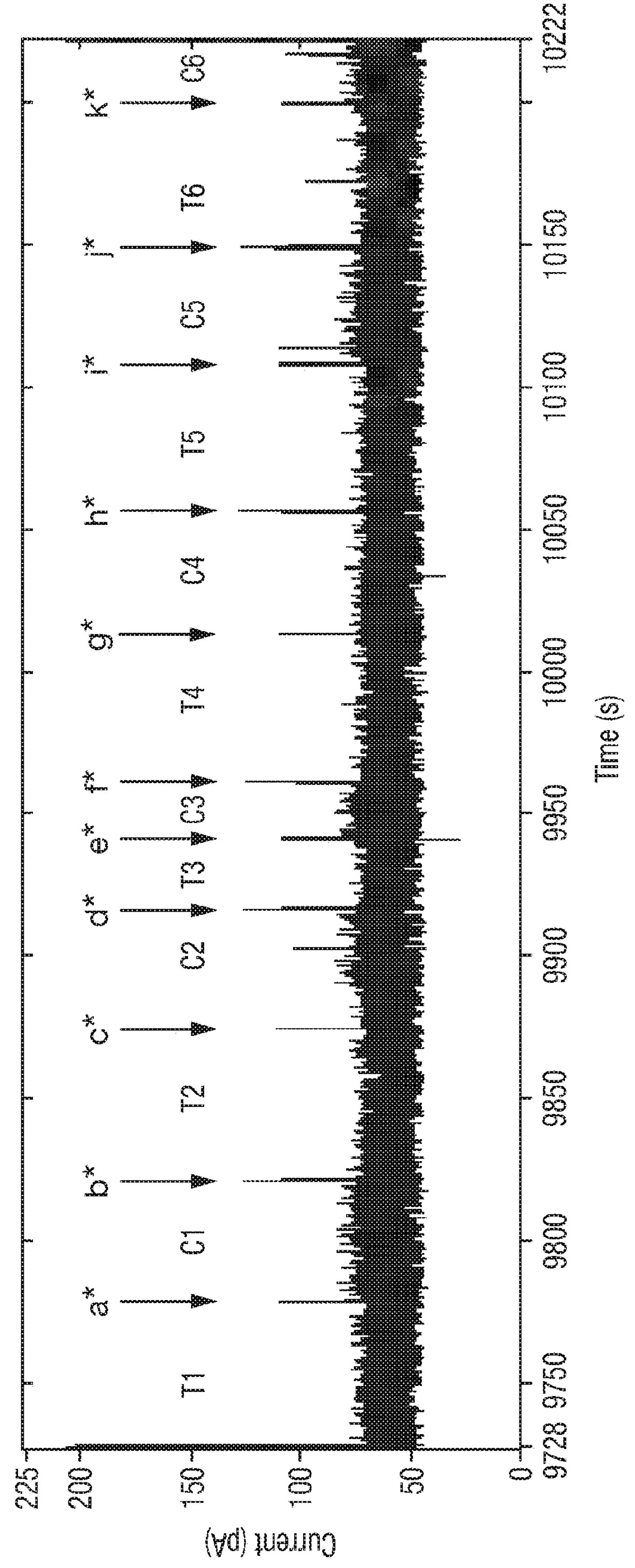
FIG. 8 shows an example current trace (y-axis label=Current (pA), x-axis label=Time (s) for both traces) of when a helicase T4 Dda-(E94C/F98W/C109A/C136A/A360C) controlled the translocation of the concatenated polynucleotide through an MspA nanopore. The first polynucleotide had 5 subsequent target polynucleotides attached to it using click chemistry. The regions of the current trace which correspond to either the template or complement region of the first polynucleotide (T1 and C1) and each subsequent polynucleotide (T2-6, C2-6) as they translocated through the nanopore are identified. Spacers in the leader and the hairpins of the polynucleotides allow more current to flow and produce a spike in current as they translocated through the nanopore. The spacers are highlighted with *(a-k) and mark transitions between the template and complement regions of the first and subsequent polynucleotides which were attached to form the target concatenated polynucleotide.
Figure 8:
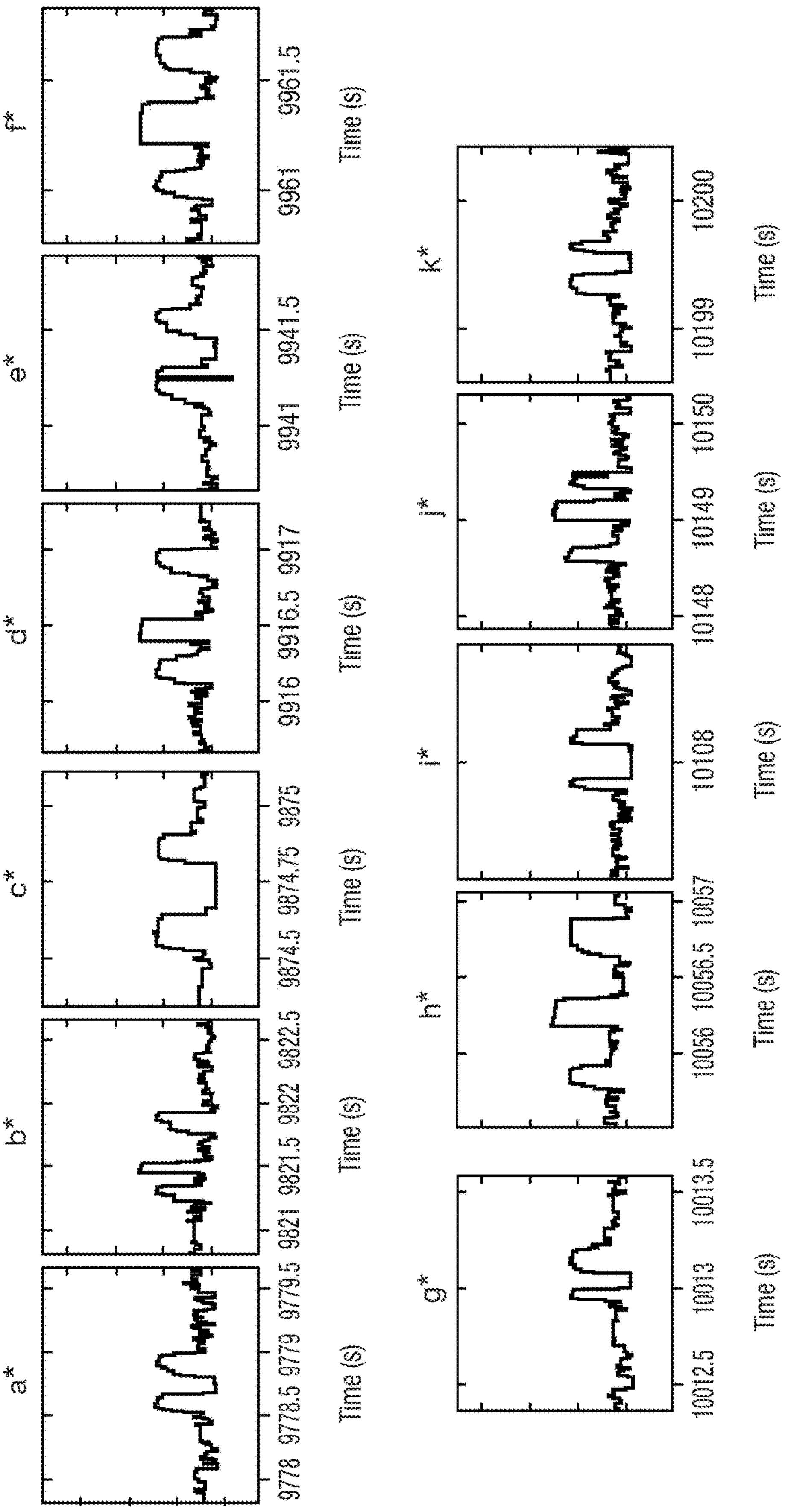
Figure 9:
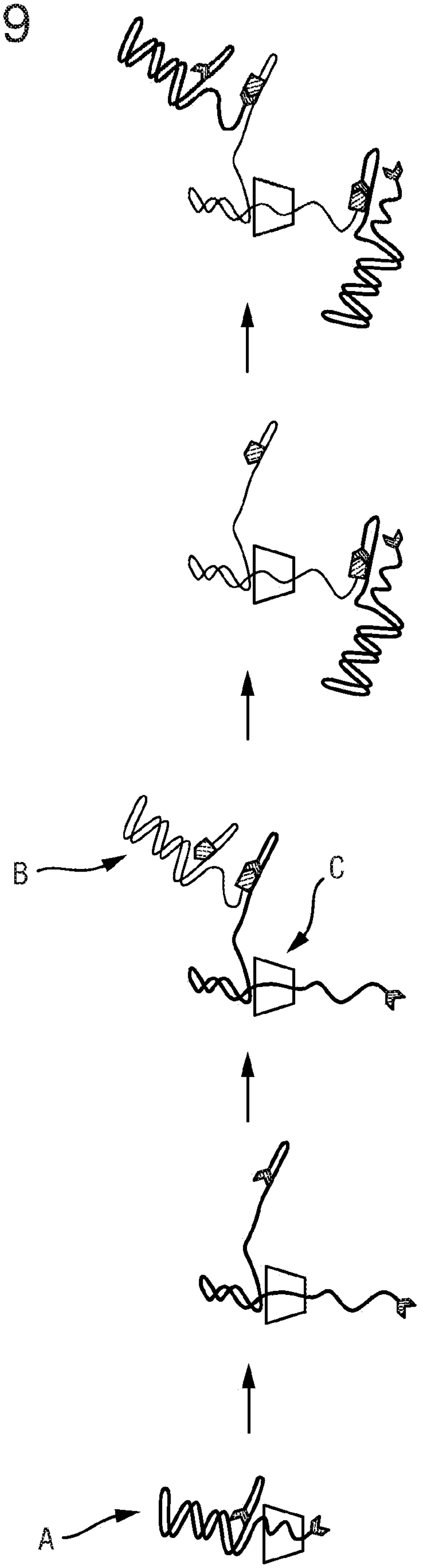
FIG. 9 shows the attachment of a subsequent target polynucleotide (labelled B) to the first target polynucleotide (labelled A) to produce a concatenated polynucleotide. The attachment point in the first target polynucleotide was revealed for attachment as the first polynucleotide moved through the pore (labelled C). In this example the first polynucleotide has one type of click chemistry reactive group (for example azide reactive groups) at either end and the subsequent polynucleotide has a different type of click chemistry reactive group (for example DBCO reactive groups) at either end. The enzyme used to control the movement of the DNA through the nanopore is not shown on this figure.

The helicase T4 Dda-(E94C/F98W/C109A/C136A/A360C) was used to control the movement of the concatenated polynucleotide through the MspA nanopore. FIG. 8 shows a current trace (top trace) of a concatenated polynucleotide (a first polynucleotide attached to five subsequent polynucleotides) as it translocated through the nanopore. The lower traces of FIG. 8 show zoomed in regions a*-k* of the upper trace. The lower traces show translocation of spacer groups (found in the leader and hairpin regions of the first and subsequent polynucleotides and marked with an a*-k*) through the nanopore. The spacer groups allowed more current to flow through the nanopore as they translocated through it. The example trace shows that the first polynucleotide was successfully attached to five subsequent polynucleotides using click chemistry.

Example 3

This example describes a method of characterising a concatenated polynucleotide where the method of attachment used to join the polynucleotides together is by click chemistry. In this example one group of adapters has a pre-bound enzyme which was used to produce a seed library and the second group has no enzyme bound which was used to produce a sequencing library.

Seed Library Prep:

A seed library Y-adapter was produced using a leader strand (ID NO: 10), a bottom strand (ID NO: 9), containing a 3' hairpin, and a blocker strand (ID NO: 8), containing a tether hybridisation site, which were annealed at 5.5 μM, 6 μM and 5 μM respectively in 50 mM HEPES pH 8, 100 mM potassium acetate from 95° C. to 22° C. at 2° C. per minute. The hybridised DNA was known as adapter 2.

An aliquot of T4 Dda-(E94C/F98W/C109A/C136A/A360C) (SEQ ID NO: 24 with mutations E94C/F98W/C109A/C136A/A360C and then (ΔM1)G1G2 (where (ΔM1) G1G2=deletion of M1 and then addition G1 and G2) was thawed on ice before 50 ul was buffer exchanged into 50 mM HEPES pH 8, 100 mM potassium acetate, 2 mM EDTA through a 0.5 ml Zeba column, according to the manufacturer's instructions. The recovered protein was quantified using the A280 nm value and adjusted to 0.25 mg $ml^{-1}$ using the same buffer.

27 ul of buffer exchanged protein was mixed with 3 ul of adapter 2 in a DNA low bind eppendorf and left to incubate for 10 mins at 35° C. 0.37 ul of 8.1 mM TMAD was then added and the sample was left to incubate for 60 mins at 35° C. 30 ul of 50 mM HEPES pH 8, 1 M NaCl, 2 mM MgCl2, 2 mM rATP was then added and left for a further 20 mins at room temperature.

222 ul of Agencourt AMPure beads (Beckman Coulter) were added and the sample incubated for 5 mins at room temperature on a rotator. The beads were pelleted on a magnetic rack and the supernatant removed. While still on the magnetic rack the beads were washed with 500 ul of 50 mM Tris pH 7.5, 2.5 M NaCl, 20% PEG 8,000, turning through 3600 to bathe the pellet on the rack. The wash buffer was removed and the pellet pulsed briefly in a centrifuge before returning to the magnetic rack to remove the last remnants of solution. The pellet was resuspended in 30 ul of 50 mM Tris pH 7.5, 20 mM NaCl for 5 mins at room temperature before being placed on a magnetic rack to recover the purified adapter which was known as preloaded Seed Y-adapter 2.

A sequencing library Y-adapter was produced by hybridising a leader strand (ID NO: 7) and a blocker strand (ID NO: 11), containing a tether hybridisation site and a polyA 5' extension, at 250 nM and 300 nM respectively in 50 mM HEPES pH 8, 100 mM potassium acetate from 95° C. to 22° C. at 2° C. per minute. 400 nM of a bottom strand (ID NO: 9), containing a 3' hairpin, was heated to 95° C. for 1 min before being snap cooled on ice in 50 mM HEPES pH 8, 100 mM potassium acetate. The two samples were equilibrated to 50° C. before being mixed 1:1 and left at 40° C. for 1 min before snap cooling on ice. This sample was known as enzyme free sequencing library Y-adapter 3.

A seed library was set up by ligating 500 ng of end-repaired and dA-tailed *E. coli* genomic DNA for 10 mins at room temperature in 50 ul with 5 ul of 200 nM preloaded seed Y-adapter 2 from above and 1 ul of 1 μM HP-adapter (ID NO: 4), in 1× Blunt/TA master mix (NEB). After incubation 0.5 ul of 5 μM hairpin tether (ID NO: 6) was added and the sample left for a further 10 mins at room temperature.

25 ul of MyOne C1 Streptavidin beads (Invitrogen) were bound to a magnetic rack and supernatant was removed. The pellet was then washed 3× by resuspension in 200 ul of 10 mM Tris pH 7.5, 2 M NaCl, 0.1 mM EDTA. Finally the beads were resuspended in 50 ul of 10 mM Tris pH 7.5, 2 M NaCl, 0.1 mM EDTA. The beads were then added to the ligation mix and incubated on a rotator for 10 mins at room temperature. The bead bound library was then added to a magnetic rack and supernatant was removed. The pellet was then washed 3× by resuspension in 200 ul of 10 mM Tris pH 7.5, 2 M NaCl, 0.1 mM EDTA. Finally the beads were resuspended in 12.5 ul of 40 mM CAPS pH 10, 40 mM KCl, 5 mM Biotin, 0.1 mM EDTA and 400 nM of tether (ID NO: 5). The sample was incubated for 10 mins at 37° C. before the beads were pelleted and the library containing supernatant was removed.

A sequencing library was set up by ligating 500 ng of end-repaired and dA-tailed *E. coli* genomic DNA for 10 mins at room temperature in 50 ul with 5 ul of 200 nM enzyme free sequencing library Y-adapter 3 from above and 1 ul of 1 μM HP-adapter (ID NO: 4), in 1× Blunt/TA master mix (NEB). After incubation 0.5 ul of 5 μM hairpin tether (ID NO: 6) was added and the sample left for a further 10 mins at room temperature.

25 ul of MyOne C1 Streptavidin beads (Invitrogen) were bound to a magnetic rack and supernatant was removed. The pellet was then washed 3× by resuspension in 200 ul of 10 mM Tris pH 7.5, 2 M NaCl, 0.1 mM EDTA. Finally the beads were resuspended in 50 ul of 10 mM Tris pH 7.5, 2 M NaCl, 0.1 mM EDTA. The beads were then added to the ligation mix and incubated on a rotator for 10 mins at room temperature. The bead bound library was then added to a magnetic rack and supernatant was removed. The pellet was then washed 3× by resuspension in 200 ul of 10 mM Tris pH 7.5, 2 M NaCl, 0.1 mM EDTA. Finally the beads were resuspended in 12.5 ul of 40 mM CAPS pH 10, 40 mM KCl, 5 mM Biotin, 0.1 mM EDTA and 400 nM of tether (ID NO: 5). The sample was incubated for 10 mins at 37° C. before the beads were pelleted and the library containing supernatant was removed.

Electrical measurements were acquired from single MspA nanopores inserted in block co-polymer in buffer (25 mM K Phosphate buffer, 150 mM Potassium Ferrocyanide (II), 150 mM Potassium Ferricyanide (III), pH 8.0). After achieving a single pore inserted in the block co-polymer, then buffer (2 mL, 25 mM K Phosphate buffer, 150 mM Potassium Ferrocyanide (II), 150 mM Potassium Ferricyanide (III), pH 8.0) was flowed through the system to remove any excess MspA nanopores. 500 ul of 25 mM potassium phosphate buffer pH 8, 500 mM KCl, 2 mM MgCl2 and 2 mM rATP, with 10 mins between each wash. 6 ul of the recovered bead purified seed library was added to 150 ul of 50 mM potassium phosphate buffer pH 8, 1 M KCl, 8 ul of 75 mM MgCl2, 75 mM rATP and 130 ul of nuclease free water. Following thorough mixing by inversion, 6 ul of the sequencing library was added and the sample again mixed thoroughly by inversion. 150 ul of this sequencing mix was then added to the nanopore system. The experiment was run at −140 mV and helicase-controlled DNA movement monitored for 6 hours.

```
ID NO: 10
/5SpC3//iSpC3//iSpC3//iSpC3//iSpC3//iSpC3//iSpC3//
iSpC3//iSpC3//iSpC3//iSpC3//iSpC3//iSpC3//iSpC3//
iSpC3//iSpC3//iSpC3//iSpC3//iSpC3//iSpC3//iSpC3//
iSpC3//iSpC3//iSpC3//iSpC3//iSpC3//iSpC3//iSpC3//
iSpC3//iSpC3/(SEQ ID NO: 28)/iSp18//iSp18//
iSp18//iSp18/(SEQ ID NO: 29)
ID NO 11
                                        (SEQ ID NO: 42)
```

Results

The helicase T4 Dda-(E94C/F98W/C109A/C136A/A360C) was used to control the movement of the concatenated polynucleotide through the MspA nanopore. Similar results were obtained as were observed for example 2.

Example 4

This example describes a method of characterising and concatenating only template strands of target polynucleotides, where the method of attachment used to join the polynucleotides together is by click chemistry.

Figure 10:
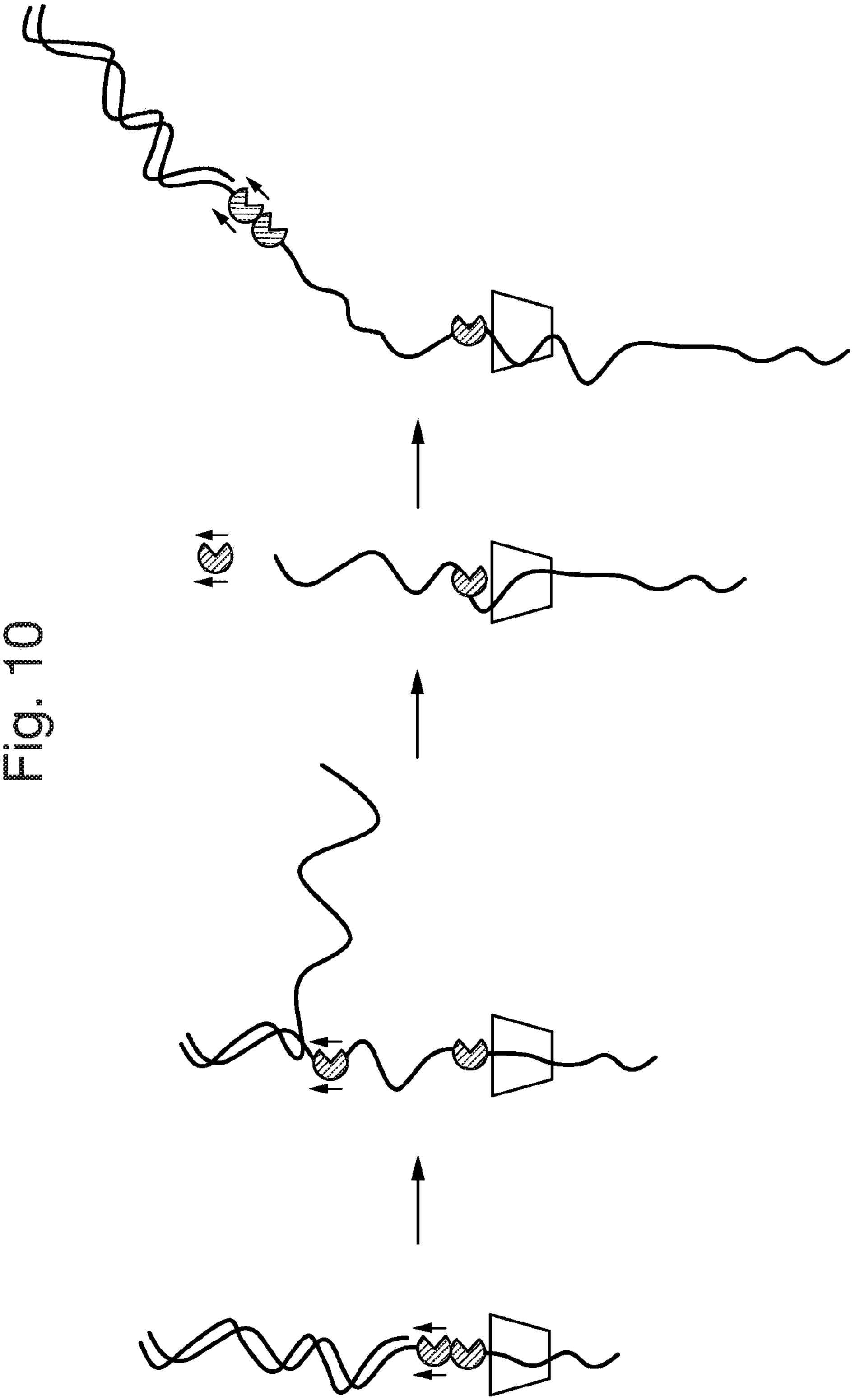
FIG. 10 shows how only template strands of target polynucleotides can be characterised and concatenated, where the method of attachment used to join the polynucleotides together is click chemistry. The concatenation adapter complex contains a motor protein and a release protein. This adapter ligated to both ends of a target polynucleotide. Both proteins are stalled on the ligated adapter complex until the adaptor ligated to a target polynucleotide is captured by the pore. Once a first polynucleotide has been captured, the blocking chemistry used to stall the proteins is overcome by both proteins. The motor protein then controls the interaction of the first polynucleotide with the pore, as described previously, and the release protein, which can translocate more quickly than the motor protein, separates the strands to expose a sequence (3' hybridisation site) in the 3' end of the adaptor linked to the end of the target polynucleotide that is complementary to a 5' nucleic acid sequence (5' hybridisation site) of the leader strand of an adapter complex that is ligated to a second target polynucleotide. With the 3' hybridisation site revealed, the 5' hybridisation site in the second target polynucleotide can then hybridise to the revealed 3' hybridisation site and covalent coupling of the 3' end of the first polynucleotide to the 5' of a the second polynucleotide can occur. This process then repeats for further concatenation of target polynucleotides.

A concatenation adapter complex that contains a motor protein and a release protein is prepared. This adapter is then ligated to both ends of a target polynucleotide. Both proteins are stalled on the ligated adapter complex until the adaptor ligated to a target polynucleotide is captured by the pore. Once a first polynucleotide has been captured, the blocking chemistry used to stall the proteins is overcome by both proteins. The motor protein then controls the interaction of the first polynucleotide with the pore, as described previously, and the release protein, which can translocate more quickly than the motor protein, separates the strands to expose a sequence (3' hybridisation site) in the 3' end of the adaptor linked to the end of the target polynucleotide that is complementary to a 5' nucleic acid sequence (5' hybridisation site) of the leader strand of an adapter complex that is ligated to a second target polynucleotide. With the 3' hybridisation site revealed, the 5' hybridisation site in the second target polynucleotide can then hybridise to the revealed 3' hybridisation site and covalent coupling of the 3' end of the first polynucleotide to the 5' of a the second polynucleotide can occur (FIG. 10). This process then repeats for further concatenation of target polynucleotides.

The invention claimed is:

1. A population of polynucleotide adaptors comprising a first polynucleotide adaptor and a second polynucleotide adaptor, wherein the first polynucleotide adaptor and the second polynucleotide adaptor each comprise a first polynucleotide strand and a second polynucleotide strand, each strand having a 5' end and a 3' end, wherein:

(a) a portion extending to the 3' end of the first polynucleotide strand is complementary to a portion extending to the 5' end of the second polynucleotide strand, and the complementary portions form a duplex;

(b) a single stranded portion extending to the 5' end of the first polynucleotide strand and a single stranded portion extending to the 3' end of the second polynucleotide strand are not complementary and do not hybridise to one another;

(c) the complementary portion extending to the 5' end of the second polynucleotide strand of the first polynucleotide adaptor comprises a sequence that is capable, when the duplex is unwound, of hybridising to a sequence comprised in the single stranded portion extending to the 5' end of the first polynucleotide strand of the second polynucleotide adaptor; and (d) the 5' end of the first polynucleotide strand comprises a click reactive group and the 3' end of the second polynucleotide strand comprises a complementary click reactive group.

2. The population according to claim 1, wherein a sequence comprised in the portion extending to the 5' end of the second polynucleotide strand of the first polynucleotide adaptor and a sequence comprised in the single stranded portion extending to the 5' end of the first polynucleotide strand of the second polynucleotide adaptor have a length of from 6 to 50 nucleotides.

3. The population according to claim 1, wherein one portion of a non-complementary region in the second polynucleotide strand of each polynucleotide adaptor forms a loop.

4. The population according to claim 1, wherein only one of the polynucleotide adaptors in the population comprises a molecular brake.

5. The population according to claim 4, wherein the molecular brake is or is derived from a polymerase, helicase, or exonuclease.

6. The population according to claim 1, wherein the duplex has a length of 6 to 200 base pairs.

7. The population according to claim 1, wherein the duplex comprises a blocker.

8. The population according to claim 7, wherein the blocker comprises iSp18.

9. The population according to claim 1, wherein the single stranded portion extending to the 5' end of the first polynucleotide strand comprises a single stranded leader sequence.

10. The population according to claim 9, wherein the leader sequence is 10 to 150 nucleotides in length.

11. The population according to claim 1, wherein each polynucleotide adapter comprises one or more polynucleotide binding proteins.

12. The population according to claim 11, wherein the one or more polynucleotide binding proteins is attached to the first polynucleotide strand of each polynucleotide adapter.

13. The population according to claim 1, wherein each polynucleotide adaptor comprises one or more anchors.

14. The population according to claim 13, wherein the one or more anchors is cholesterol.

15. A population of polynucleotide adaptors comprising a first polynucleotide adaptor and a second polynucleotide adaptor, wherein the first polynucleotide adaptor and the second polynucleotide adaptor each comprise a first polynucleotide strand and a second polynucleotide strand, each strand having a 5' end and a 3' end, wherein:

(a) a portion extending to the 3' end of the first polynucleotide strand is complementary to a portion extending to the 5' end of the second polynucleotide strand, and the complementary portions form a duplex;

(b) a single stranded portion extending to the 5' end of the first polynucleotide strand and a single stranded portion extending to the 3' end of the second polynucleotide strand are not complementary and do not hybridise to one another;

(c) the complementary portion extending to the 5' end of the second polynucleotide strand of the first polynucleotide adaptor comprises a sequence that is capable, when the duplex is unwound, of hybridising to a sequence comprised in the single stranded portion extending to the 5' end of the first polynucleotide strand of the second polynucleotide adaptor; and (d) the 5' end of the first polynucleotide strand comprises a phosphatase.

16. A kit for characterising two or more double stranded target polynucleotides, comprising the population of polynucleotide adaptors according to claim 1 and one or more of the following: a population of hairpin loops; a microparticle; one or more anchors capable of coupling a polynucleotide to a membrane; membrane components; and a magnet or electromagnet.

17. The kit according to claim 16, wherein the membrane components comprise components of an amphiphilic layer or a triblock copolymer membrane.

18. The kit according to claim 16, wherein the kit further comprises a transmembrane protein pore.

* * * * *

SEQUENCE LISTING

```
<160> NUMBER OF SEQ ID NOS: 43

<210> SEQ ID NO 1
<211> LENGTH: 558
<212> TYPE: DNA
<213> ORGANISM: Artificial Sequence
<220> FEATURE:
<223> OTHER INFORMATION: MS-B1 mutant MspA monomer

<400> SEQUENCE: 1

atgggtctgg ataatgaact gagcctggtg gacggtcaag atcgtaccct gacggtgcaa      60

caatgggata cctttctgaa tggcgttttt ccgctggatc gtaatcgcct gacccgtgaa     120

tggtttcatt ccggtcgcgc aaaatatatc gtcgcaggcc cgggtgctga cgaattcgaa     180

ggcacgctgg aactgggtta tcagattggc tttccgtggt cactgggcgt tggtatcaac     240

ttctcgtaca ccacgccgaa tattctgatc aacaatggta acattaccgc accgccgttt     300

ggcctgaaca gcgtgattac gccgaacctg tttccgggtg ttagcatctc tgcccgtctg     360

ggcaatggtc cgggcattca agaagtggca acctttagtg tgcgcgtttc cggcgctaaa     420

ggcggtgtcg cggtgtctaa cgcccacggt accgttacgg gcgcggccgg cggtgtcctg     480

ctgcgtccgt tcgcgcgcct gattgcctct accggcgaca gcgttacgac ctatggcgaa     540

ccgtggaata tgaactaa                                                  558


<210> SEQ ID NO 2
<211> LENGTH: 184
<212> TYPE: PRT
<213> ORGANISM: Artificial Sequence
<220> FEATURE:
<223> OTHER INFORMATION: Mature form of the MS-B1 mutant of the MspA
      monomer

<400> SEQUENCE: 2

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80
```

-continued

```
Ser Tyr Thr Thr Pro Asn Ile Leu Ile Asn Asn Gly Asn Ile Thr Ala
                85                  90                  95

Pro Pro Phe Gly Leu Asn Ser Val Ile Thr Pro Asn Leu Phe Pro Gly
            100                 105                 110

Val Ser Ile Ser Ala Arg Leu Gly Asn Gly Pro Gly Ile Gln Glu Val
        115                 120                 125

Ala Thr Phe Ser Val Arg Val Ser Gly Ala Lys Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180


<210> SEQ ID NO 3
<211> LENGTH: 885
<212> TYPE: DNA
<213> ORGANISM: Artificial Sequence
<220> FEATURE:
<223> OTHER INFORMATION: Monomer of  alpha-hemolysin-E111N/K147N

<400> SEQUENCE: 3

atggcagatt ctgatattaa tattaaaacc ggtactacag atattggaag caatactaca      60

gtaaaaacag gtgatttagt cacttatgat aaagaaaatg gcatgcacaa aaaagtattt     120

tatagtttta tcgatgataa aaatcacaat aaaaaactgc tagttattag aacaaaaggt     180

accattgctg gtcaatatag agtttatagc gaagaaggtg ctaacaaaag tggtttagcc     240

tggccttcag cctttaaggt acagttgcaa ctacctgata atgaagtagc tcaaatatct     300

gattactatc caagaaattc gattgataca aaaaactata tgagtacttt aacttatgga     360

ttcaacggta atgttactgg tgatgataca ggaaaaattg gcggccttat tggtgcaaat     420

gtttcgattg gtcatacact gaactatgtt caacctgatt tcaaaacaat tttagagagc     480

ccaactgata aaaaagtagg ctggaaagtg atatttaaca atatggtgaa tcaaaattgg     540

ggaccatacg atcgagattc ttggaacccg gtatatggca atcaactttt catgaaaact     600

agaaatggtt ctatgaaagc agcagataac ttccttgatc ctaacaaagc aagttctcta     660

ttatcttcag ggttttcacc agacttcgct acagttatta ctatggatag aaaagcatcc     720

aaacaacaaa caaatataga tgtaatatac gaacgagttc gtgatgatta ccaattgcat     780

tggacttcaa caaattggaa aggtaccaat actaaagata aatggacaga tcgttcttca     840

gaaagatata aaatcgattg ggaaaaagaa gaaatgacaa attaa                     885


<210> SEQ ID NO 4
<211> LENGTH: 293
<212> TYPE: PRT
<213> ORGANISM: Artificial Sequence
<220> FEATURE:
<223> OTHER INFORMATION: Monomer of  alpha-HL-NN

<400> SEQUENCE: 4

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45
```

Asn Lys Lys Leu Leu Val Ile Arg Thr Lys Gly Thr Ile Ala Gly Gln
50 55 60

Tyr Arg Val Tyr Ser Glu Glu Gly Ala Asn Lys Ser Gly Leu Ala Trp
65 70 75 80

Pro Ser Ala Phe Lys Val Gln Leu Gln Leu Pro Asp Asn Glu Val Ala
85 90 95

Gln Ile Ser Asp Tyr Tyr Pro Arg Asn Ser Ile Asp Thr Lys Asn Tyr
100 105 110

Met Ser Thr Leu Thr Tyr Gly Phe Asn Gly Asn Val Thr Gly Asp Asp
115 120 125

Thr Gly Lys Ile Gly Gly Leu Ile Gly Ala Asn Val Ser Ile Gly His
130 135 140

Thr Leu Asn Tyr Val Gln Pro Asp Phe Lys Thr Ile Leu Glu Ser Pro
145 150 155 160

Thr Asp Lys Lys Val Gly Trp Lys Val Ile Phe Asn Asn Met Val Asn
165 170 175

Gln Asn Trp Gly Pro Tyr Asp Arg Asp Ser Trp Asn Pro Val Tyr Gly
180 185 190

Asn Gln Leu Phe Met Lys Thr Arg Asn Gly Ser Met Lys Ala Ala Asp
195 200 205

Asn Phe Leu Asp Pro Asn Lys Ala Ser Ser Leu Leu Ser Ser Gly Phe
210 215 220

Ser Pro Asp Phe Ala Thr Val Ile Thr Met Asp Arg Lys Ala Ser Lys
225 230 235 240

Gln Gln Thr Asn Ile Asp Val Ile Tyr Glu Arg Val Arg Asp Asp Tyr
245 250 255

Gln Leu His Trp Thr Ser Thr Asn Trp Lys Gly Thr Asn Thr Lys Asp
260 265 270

Lys Trp Thr Asp Arg Ser Ser Glu Arg Tyr Lys Ile Asp Trp Glu Lys
275 280 285

Glu Glu Met Thr Asn
290

<210> SEQ ID NO 5
<211> LENGTH: 184
<212> TYPE: PRT
<213> ORGANISM: Artificial Sequence
<220> FEATURE:
<223> OTHER INFORMATION: MspB

<400> SEQUENCE: 5

Gly Leu Asp Asn Glu Leu Ser Leu Val Asp Gly Gln Asp Arg Thr Leu
1 5 10 15

Thr Val Gln Gln Trp Asp Thr Phe Leu Asn Gly Val Phe Pro Leu Asp
20 25 30

Arg Asn Arg Leu Thr Arg Glu Trp Phe His Ser Gly Arg Ala Lys Tyr
35 40 45

Ile Val Ala Gly Pro Gly Ala Asp Glu Phe Glu Gly Thr Leu Glu Leu
50 55 60

Gly Tyr Gln Ile Gly Phe Pro Trp Ser Leu Gly Val Gly Ile Asn Phe
65 70 75 80

Ser Tyr Thr Thr Pro Asn Ile Leu Ile Asp Asp Gly Asp Ile Thr Ala
85 90 95

Pro Pro Phe Gly Leu Asn Ser Val Ile Thr Pro Asn Leu Phe Pro Gly
100 105 110

-continued

```
Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180


<210> SEQ ID NO 6
<211> LENGTH: 184
<212> TYPE: PRT
<213> ORGANISM: Artificial Sequence
<220> FEATURE:
<223> OTHER INFORMATION: MspC

<400> SEQUENCE: 6

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
            20                  25                  30

Arg Asn Arg Leu Thr Arg Glu Trp Phe His Ser Gly Arg Ala Lys Tyr
        35                  40                  45

Ile Val Ala Gly Pro Gly Ala Asp Glu Phe Glu Gly Thr Leu Glu Leu
    50                  55                  60

Gly Tyr Gln Ile Gly Phe Pro Trp Ser Leu Gly Val Gly Ile Asn Phe
65                  70                  75                  80

Ser Tyr Thr Thr Pro Asn Ile Leu Ile Asp Asp Gly Asp Ile Thr Gly
                85                  90                  95

Pro Pro Phe Gly Leu Glu Ser Val Ile Thr Pro Asn Leu Phe Pro Gly
            100                 105                 110

Val Ser Ile Ser Ala Asp Leu Gly Asn Gly Pro Gly Ile Gln Glu Val
        115                 120                 125

Ala Thr Phe Ser Val Asp Val Ser Gly Pro Ala Gly Gly Val Ala Val
    130                 135                 140

Ser Asn Ala His Gly Thr Val Thr Gly Ala Ala Gly Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180


<210> SEQ ID NO 7
<211> LENGTH: 183
<212> TYPE: PRT
<213> ORGANISM: Artificial Sequence
<220> FEATURE:
<223> OTHER INFORMATION: MspD

<400> SEQUENCE: 7

Val Asp Asn Gln Leu Ser Val Val Asp Gly Gln Gly Arg Thr Leu Thr
1               5                   10                  15

Val Gln Gln Ala Glu Thr Phe Leu Asn Gly Val Phe Pro Leu Asp Arg
            20                  25                  30

Asn Arg Leu Thr Arg Glu Trp Phe His Ser Gly Arg Ala Thr Tyr His
```

-continued

```
        35                  40                  45

Val Ala Gly Pro Gly Ala Asp Glu Phe Glu Gly Thr Leu Glu Leu Gly
    50                  55                  60

Tyr Gln Val Gly Phe Pro Trp Ser Leu Gly Val Gly Ile Asn Phe Ser
65                  70                  75                  80

Tyr Thr Thr Pro Asn Ile Leu Ile Asp Gly Gly Asp Ile Thr Gln Pro
                85                  90                  95

Pro Phe Gly Leu Asp Thr Ile Ile Thr Pro Asn Leu Phe Pro Gly Val
            100                 105                 110

Ser Ile Ser Ala Asp Leu Gly Asn Gly Pro Gly Ile Gln Glu Val Ala
        115                 120                 125

Thr Phe Ser Val Asp Val Lys Gly Ala Lys Gly Ala Val Ala Val Ser
    130                 135                 140

Asn Ala His Gly Thr Val Thr Gly Ala Ala Gly Gly Val Leu Leu Arg
145                 150                 155                 160

Pro Phe Ala Arg Leu Ile Ala Ser Thr Gly Asp Ser Val Thr Thr Tyr
                165                 170                 175

Gly Glu Pro Trp Asn Met Asn
            180


<210> SEQ ID NO 8
<211> LENGTH: 1830
<212> TYPE: DNA
<213> ORGANISM: Artificial Sequence
<220> FEATURE:
<223> OTHER INFORMATION: Phi29 DNA polymerase

<400> SEQUENCE: 8

atgaaacaca tgccgcgtaa aatgtatagc tgcgcgtttg aaaccacgac caaagtggaa      60

gattgtcgcg tttgggccta tggctacatg aacatcgaag atcattctga atacaaaatc     120

ggtaacagtc tggatgaatt tatggcatgg gtgctgaaag ttcaggcgga tctgtacttc     180

cacaacctga aatttgatgg cgcattcatt atcaactggc tggaacgtaa tggctttaaa     240

tggagcgcgg atggtctgcc gaacacgtat aataccatta tctctcgtat gggccagtgg     300

tatatgattg atatctgcct gggctacaaa ggtaaacgca aaattcatac cgtgatctat     360

gatagcctga aaaaactgcc gtttccggtg aagaaaattg cgaaagattt caaactgacg     420

gttctgaaag gcgatattga ttatcacaaa gaacgtccgg ttggttacaa aatcaccccg     480

gaagaatacg catacatcaa aaacgatatc cagatcatcg cagaagcgct gctgattcag     540

tttaaacagg gcctggatcg catgaccgcg ggcagtgata gcctgaaagg tttcaaagat     600

atcatcacga ccaaaaaatt caaaaaagtg ttcccgacgc tgagcctggg tctggataaa     660

gaagttcgtt atgcctaccg cggcggtttt acctggctga acgatcgttt caaagaaaaa     720

gaaattggcg agggtatggt gtttgatgtt aatagtctgt atccggcaca gatgtacagc     780

cgcctgctgc cgtatggcga accgatcgtg ttcgagggta aatatgtttg ggatgaagat     840

tacccgctgc atattcagca catccgttgt gaatttgaac tgaaagaagg ctatattccg     900

accattcaga tcaaacgtag tcgcttctat aagggtaacg aatacctgaa aagctctggc     960

ggtgaaatcg cggatctgtg gctgagtaac gtggatctgg aactgatgaa agaacactac    1020

gatctgtaca acgttgaata catcagcggc ctgaaattta aagccacgac cggtctgttc    1080

aaagatttca tcgataaatg gacctacatc aaaacgacct ctgaaggcgc gattaaacag    1140

ctggccaaac tgatgctgaa cagcctgtat ggcaaattcg cctctaatcc ggatgtgacc    1200
```

-continued

```
ggtaaagttc cgtacctgaa agaaaatggc gcactgggtt ttcgcctggg cgaagaagaa   1260

acgaaagatc cggtgtatac cccgatgggt gttttcatta cggcctgggc acgttacacg   1320

accatcaccg cggcccaggc atgctatgat cgcattatct actgtgatac cgattctatt   1380

catctgacgg gcaccgaaat cccggatgtg attaaagata tcgttgatcc gaaaaaactg   1440

ggttattggg cccacgaaag tacgtttaaa cgtgcaaaat acctgcgcca gaaaacctac   1500

atccaggata tctacatgaa agaagtggat ggcaaactgg ttgaaggttc tccggatgat   1560

tacaccgata tcaaattcag tgtgaaatgc gccggcatga cggataaaat caaaaaagaa   1620

gtgaccttcg aaaacttcaa agttggtttc agccgcaaaa tgaaaccgaa accggtgcag   1680

gttccgggcg gtgtggttct ggtggatgat acgtttacca ttaaatctgg cggtagtgcg   1740

tggagccatc cgcagttcga aaaaggcggt ggctctggtg gcggttctgg cggtagtgcc   1800

tggagccacc cgcagtttga aaaataataa                                    1830
```

```
<210> SEQ ID NO 9
<211> LENGTH: 608
<212> TYPE: PRT
<213> ORGANISM: Artificial Sequence
<220> FEATURE:
<223> OTHER INFORMATION: Phi29 DNA polymerase

<400> SEQUENCE: 9

Met Lys His Met Pro Arg Lys Met Tyr Ser Cys Ala Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
    210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255
```

-continued

```
Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Ser
                565                 570                 575

Gly Gly Ser Ala Trp Ser His Pro Gln Phe Glu Lys Gly Gly Gly Ser
            580                 585                 590

Gly Gly Gly Ser Gly Gly Ser Ala Trp Ser His Pro Gln Phe Glu Lys
        595                 600                 605
```

<210> SEQ ID NO 10
<211> LENGTH: 1390
<212> TYPE: DNA
<213> ORGANISM: Artificial Sequence
<220> FEATURE:
<223> OTHER INFORMATION: Codon optimised polynucleotide sequence derived from the sbcB gene from E. coli

<400> SEQUENCE: 10

```
atgatgaacg atggcaaaca gcagagcacc ttcctgtttc atgattatga aaccttcggt      60
```

acccatccgg ccctggatcg tccggcgcag tttgcggcca ttcgcaccga tagcgaattc 120
aatgtgattg gcgaaccgga agtgttttat tgcaaaccgg ccgatgatta tctgccgcag 180
ccgggtgcgg tgctgattac cggtattacc ccgcaggaag cgcgcgcgaa aggtgaaaac 240
gaagcggcgt ttgccgcgcg cattcatagc ctgtttaccg tgccgaaaac ctgcattctg 300
ggctataaca atgtgcgctt cgatgatgaa gttacccgta atatctttta tcgtaacttt 360
tatgatccgt atgcgtggag ctggcagcat gataacagcc gttgggatct gctggatgtg 420
atgcgcgcgt gctatgcgct gcgcccggaa ggcattaatt ggccggaaaa cgatgatggc 480
ctgccgagct ttcgtctgga acatctgacc aaagccaacg gcattgaaca tagcaatgcc 540
catgatgcga tggccgatgt ttatgcgacc attgcgatgg cgaaactggt taaaacccgt 600
cagccgcgcc tgtttgatta tctgtttacc caccgtaaca aacacaaact gatggcgctg 660
attgatgttc cgcagatgaa accgctggtg catgtgagcg gcatgtttgg cgcctggcgc 720
ggcaacacca gctgggtggc ccgctggcc tggcacccgg aaaatcgtaa cgccgtgatt 780
atggttgatc tggccggtga tattagcccg ctgctggaac tggatagcga taccctgcgt 840
gaacgcctgt ataccgccaa aaccgatctg ggcgataatg ccgccgtgcc ggtgaaactg 900
gttcacatta acaaatgccc ggtgctggcc caggcgaaca ccctgcgccc ggaagatgcg 960
gatcgtctgg gtattaatcg ccagcattgt ctggataatc tgaaaatcct gcgtgaaaac 1020
ccgcaggtgc gtgaaaaagt ggtggcgatc ttcgcggaag cggaaccgtt caccccgagc 1080
gataacgtgg atgcgcagct gtataacggc ttctttagcg atgccgatcg cgcggcgatg 1140
aaaatcgttc tggaaaccga accgcgcaat ctgccggcgc tggatattac ctttgttgat 1200
aaacgtattg aaaaactgct gtttaattat cgtgcgcgca attttccggg taccctggat 1260
tatgccgaac agcagcgttg gctggaacat cgtcgtcagg ttttcacccc ggaatttctg 1320
cagggttatg cggatgaact gcagatgctg gttcagcagt atgccgatga taaagaaaaa 1380
gtggcgctgc 1390

<210> SEQ ID NO 11
<211> LENGTH: 485
<212> TYPE: PRT
<213> ORGANISM: Artificial Sequence
<220> FEATURE:
<223> OTHER INFORMATION: Exonuclease I enzyme (EcoExoI) from E. coli

<400> SEQUENCE: 11

Met Met Asn Asp Gly Lys Gln Gln Ser Thr Phe Leu Phe His Asp Tyr
1 5 10 15

Glu Thr Phe Gly Thr His Pro Ala Leu Asp Arg Pro Ala Gln Phe Ala
20 25 30

Ala Ile Arg Thr Asp Ser Glu Phe Asn Val Ile Gly Glu Pro Glu Val
35 40 45

Phe Tyr Cys Lys Pro Ala Asp Asp Tyr Leu Pro Gln Pro Gly Ala Val
50 55 60

Leu Ile Thr Gly Ile Thr Pro Gln Glu Ala Arg Ala Lys Gly Glu Asn
65 70 75 80

Glu Ala Ala Phe Ala Ala Arg Ile His Ser Leu Phe Thr Val Pro Lys
85 90 95

Thr Cys Ile Leu Gly Tyr Asn Asn Val Arg Phe Asp Asp Glu Val Thr
100 105 110

Arg Asn Ile Phe Tyr Arg Asn Phe Tyr Asp Pro Tyr Ala Trp Ser Trp

-continued

```
        115                 120                 125

Gln His Asp Asn Ser Arg Trp Asp Leu Leu Asp Val Met Arg Ala Cys
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
    290                 295                 300

Lys Cys Pro Val Leu Ala Gln Ala Asn Thr Leu Arg Pro Glu Asp Ala
305                 310                 315                 320

Asp Arg Leu Gly Ile Asn Arg Gln His Cys Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
        435                 440                 445

Met Leu Val Gln Gln Tyr Ala Asp Asp Lys Glu Lys Val Ala Leu Leu
    450                 455                 460

Lys Ala Leu Trp Gln Tyr Ala Glu Glu Ile Val Ser Gly Ser Gly His
465                 470                 475                 480

His His His His His
                485
```

<210> SEQ ID NO 12
<211> LENGTH: 804
<212> TYPE: DNA
<213> ORGANISM: Artificial Sequence
<220> FEATURE:
<223> OTHER INFORMATION: Codon optimised polynucleotide sequence derived
      from the xthA gene from E. coli -continued

<400> SEQUENCE: 12

```
atgaaatttg tctcttttaa tatcaacggc ctgcgcgcca gacctcacca gcttgaagcc      60

atcgtcgaaa agcaccaacc ggatgtgatt ggcctgcagg agacaaaagt tcatgacgat     120

atgtttccgc tcgaagaggt ggcgaagctc ggctacaacg tgttttatca cgggcagaaa     180

ggccattatg gcgtggcgct gctgaccaaa gagacgccga ttgccgtgcg tcgcggcttt     240

cccggtgacg acgaagaggc gcagcggcgg attattatgg cggaaatccc ctcactgctg     300

ggtaatgtca ccgtgatcaa cggttacttc ccgcagggtg aaagccgcga ccatccgata     360

aaattcccgg caaaagcgca gttttatcag aatctgcaaa actacctgga aaccgaactc     420

aaacgtgata atccggtact gattatgggc gatatgaata tcagccctac agatctggat     480

atcggcattg gcgaagaaaa ccgtaagcgc tggctgcgta ccggtaaatg ctctttcctg     540

ccggaagagc gcgaatggat ggacaggctg atgagctggg ggttggtcga taccttccgc     600

catgcgaatc cgcaaacagc agatcgtttc tcatggtttg attaccgctc aaaaggtttt     660

gacgataacc gtggtctgcg catcgacctg ctgctcgcca gccaaccgct ggcagaatgt     720

tgcgtagaaa ccggcatcga ctatgaaatc cgcagcatgg aaaaaccgtc cgatcacgcc     780

cccgtctggg cgaccttccg ccgc                                            804
```

<210> SEQ ID NO 13
<211> LENGTH: 268
<212> TYPE: PRT
<213> ORGANISM: Artificial Sequence
<220> FEATURE:
<223> OTHER INFORMATION: Exonuclease III enzyme from E. coli

<400> SEQUENCE: 13

```
Met Lys Phe Val Ser Phe Asn Ile Asn Gly Leu Arg Ala Arg Pro His
1               5                   10                  15

Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45

Lys Leu Gly Tyr Asn Val Phe Tyr His Gly Gln Lys Gly His Tyr Gly
    50                  55                  60

Val Ala Leu Leu Thr Lys Glu Thr Pro Ile Ala Val Arg Arg Gly Phe
65                  70                  75                  80

Pro Gly Asp Asp Glu Glu Ala Gln Arg Arg Ile Ile Met Ala Glu Ile
                85                  90                  95

Pro Ser Leu Leu Gly Asn Val Thr Val Ile Asn Gly Tyr Phe Pro Gln
            100                 105                 110

Gly Glu Ser Arg Asp His Pro Ile Lys Phe Pro Ala Lys Ala Gln Phe
        115                 120                 125

Tyr Gln Asn Leu Gln Asn Tyr Leu Glu Thr Glu Leu Lys Arg Asp Asn
    130                 135                 140

Pro Val Leu Ile Met Gly Asp Met Asn Ile Ser Pro Thr Asp Leu Asp
145                 150                 155                 160

Ile Gly Ile Gly Glu Glu Asn Arg Lys Arg Trp Leu Arg Thr Gly Lys
                165                 170                 175

Cys Ser Phe Leu Pro Glu Glu Arg Glu Trp Met Asp Arg Leu Met Ser
            180                 185                 190

Trp Gly Leu Val Asp Thr Phe Arg His Ala Asn Pro Gln Thr Ala Asp
        195                 200                 205
```

-continued

```
Arg Phe Ser Trp Phe Asp Tyr Arg Ser Lys Gly Phe Asp Asp Asn Arg
    210                 215                 220

Gly Leu Arg Ile Asp Leu Leu Leu Ala Ser Gln Pro Leu Ala Glu Cys
225                 230                 235                 240

Cys Val Glu Thr Gly Ile Asp Tyr Glu Ile Arg Ser Met Glu Lys Pro
                245                 250                 255

Ser Asp His Ala Pro Val Trp Ala Thr Phe Arg Arg
            260                 265
```

<210> SEQ ID NO 14
<211> LENGTH: 1275
<212> TYPE: DNA
<213> ORGANISM: Artificial Sequence
<220> FEATURE:
<223> OTHER INFORMATION: Codon optimised polynucleotide sequence derived from the recJ gene from T. thermophilus

<400> SEQUENCE: 14

```
atgtttcgtc gtaaagaaga tctggatccg ccgctggcac tgctgccgct gaaaggcctg     60

cgcgaagccg ccgcactgct ggaagaagcg ctgcgtcaag gtaaacgcat tcgtgttcac    120

ggcgactatg atgcggatgg cctgaccggc accgcgatcc tggttcgtgg tctggccgcc    180

ctgggtgcgg atgttcatcc gtttatcccg caccgcctgg aagaaggcta tggtgtcctg    240

atggaacgcg tcccggaaca tctggaagcc tcggacctgt ttctgaccgt tgactgcggc    300

attaccaacc atgcggaact gcgcgaactg ctggaaaatg gcgtggaagt cattgttacc    360

gatcatcata cgccgggcaa aacgccgccg ccgggtctgg tcgtgcatcc ggcgctgacg    420

ccggatctga aagaaaaacc gaccggcgca ggcgtggcgt ttctgctgct gtgggcactg    480

catgaacgcc tgggcctgcc gccgccgctg gaatacgcgg acctggcagc cgttggcacc    540

attgccgacg ttgccccgct gtggggttgg aatcgtgcac tggtgaaaga aggtctggca    600

cgcatcccgg cttcatcttg ggtgggcctg cgtctgctgg ctgaagccgt gggctatacc    660

ggcaaagcgg tcgaagtcgc tttccgcatc gcgccgcgca tcaatgcggc ttcccgcctg    720

ggcgaagcgg aaaaagccct gcgcctgctg ctgacggatg atgcggcaga agctcaggcg    780

ctggtcggcg aactgcaccg tctgaacgcc cgtcgtcaga ccctggaaga agcgatgctg    840

cgcaaactgc tgccgcaggc cgacccggaa gcgaaagcca tcgttctgct ggacccggaa    900

ggccatccgg gtgttatggg tattgtggcc tctcgcatcc tggaagcgac cctgcgcccg    960

gtctttctgg tggcccaggg caaaggcacc gtgcgttcgc tggctccgat ttccgccgtc   1020

gaagcactgc gcagcgcgga agatctgctg ctgcgttatg gtggtcataa agaagcggcg   1080

ggtttcgcaa tggatgaagc gctgtttccg gcgttcaaag cacgcgttga agcgtatgcc   1140

gcacgtttcc cggatccggt tcgtgaagtg gcactgctgg atctgctgcc ggaaccgggc   1200

ctgctgccgc aggtgttccg tgaactggca ctgctggaac cgtatggtga aggtaacccg   1260

gaaccgctgt tcctg                                                    1275
```

<210> SEQ ID NO 15
<211> LENGTH: 425
<212> TYPE: PRT
<213> ORGANISM: Artificial Sequence
<220> FEATURE:
<223> OTHER INFORMATION: RecJ enzyme from T. thermophilus (TthRecJ-cd)

<400> SEQUENCE: 15

```
Met Phe Arg Arg Lys Glu Asp Leu Asp Pro Pro Leu Ala Leu Leu Pro
```

-continued

```
1               5                   10                  15

Leu Lys Gly Leu Arg Glu Ala Ala Ala Leu Leu Glu Glu Ala Leu Arg
            20                  25                  30

Gln Gly Lys Arg Ile Arg Val His Gly Asp Tyr Asp Ala Asp Gly Leu
        35                  40                  45

Thr Gly Thr Ala Ile Leu Val Arg Gly Leu Ala Ala Leu Gly Ala Asp
    50                  55                  60

Val His Pro Phe Ile Pro His Arg Leu Glu Glu Gly Tyr Gly Val Leu
65                  70                  75                  80

Met Glu Arg Val Pro Glu His Leu Glu Ala Ser Asp Leu Phe Leu Thr
                85                  90                  95

Val Asp Cys Gly Ile Thr Asn His Ala Glu Leu Arg Glu Leu Leu Glu
            100                 105                 110

Asn Gly Val Glu Val Ile Val Thr Asp His His Thr Pro Gly Lys Thr
        115                 120                 125

Pro Pro Pro Gly Leu Val Val His Pro Ala Leu Thr Pro Asp Leu Lys
    130                 135                 140

Glu Lys Pro Thr Gly Ala Gly Val Ala Phe Leu Leu Leu Trp Ala Leu
145                 150                 155                 160

His Glu Arg Leu Gly Leu Pro Pro Pro Leu Glu Tyr Ala Asp Leu Ala
                165                 170                 175

Ala Val Gly Thr Ile Ala Asp Val Ala Pro Leu Trp Gly Trp Asn Arg
            180                 185                 190

Ala Leu Val Lys Glu Gly Leu Ala Arg Ile Pro Ala Ser Ser Trp Val
        195                 200                 205

Gly Leu Arg Leu Leu Ala Glu Ala Val Gly Tyr Thr Gly Lys Ala Val
    210                 215                 220

Glu Val Ala Phe Arg Ile Ala Pro Arg Ile Asn Ala Ala Ser Arg Leu
225                 230                 235                 240

Gly Glu Ala Glu Lys Ala Leu Arg Leu Leu Leu Thr Asp Asp Ala Ala
                245                 250                 255

Glu Ala Gln Ala Leu Val Gly Glu Leu His Arg Leu Asn Ala Arg Arg
            260                 265                 270

Gln Thr Leu Glu Glu Ala Met Leu Arg Lys Leu Leu Pro Gln Ala Asp
        275                 280                 285

Pro Glu Ala Lys Ala Ile Val Leu Leu Asp Pro Glu Gly His Pro Gly
    290                 295                 300

Val Met Gly Ile Val Ala Ser Arg Ile Leu Glu Ala Thr Leu Arg Pro
305                 310                 315                 320

Val Phe Leu Val Ala Gln Gly Lys Gly Thr Val Arg Ser Leu Ala Pro
                325                 330                 335

Ile Ser Ala Val Glu Ala Leu Arg Ser Ala Glu Asp Leu Leu Leu Arg
            340                 345                 350

Tyr Gly Gly His Lys Glu Ala Ala Gly Phe Ala Met Asp Glu Ala Leu
        355                 360                 365

Phe Pro Ala Phe Lys Ala Arg Val Glu Ala Tyr Ala Ala Arg Phe Pro
    370                 375                 380

Asp Pro Val Arg Glu Val Ala Leu Leu Asp Leu Leu Pro Glu Pro Gly
385                 390                 395                 400

Leu Leu Pro Gln Val Phe Arg Glu Leu Ala Leu Leu Glu Pro Tyr Gly
                405                 410                 415

Glu Gly Asn Pro Glu Pro Leu Phe Leu
            420                 425
```

<210> SEQ ID NO 16
<211> LENGTH: 738
<212> TYPE: DNA
<213> ORGANISM: Artificial Sequence
<220> FEATURE:
<223> OTHER INFORMATION: Codon optimised polynucleotide sequence derived from the bacteriophage lambda exo (redX) gene

<400> SEQUENCE: 16
tccggaagcg gctctggtag tggttctggc atgacaccgg acattatcct gcagcgtacc 60
gggatcgatg tgagagctgt cgaacagggg gatgatgcgt ggcacaaatt acggctcggc 120
gtcatcaccg cttcagaagt tcacaacgtg atagcaaaac cccgctccgg aaagaagtgg 180
cctgacatga aaatgtccta cttccacacc ctgcttgctg aggtttgcac cggtgtggct 240
ccggaagtta acgctaaagc actggcctgg ggaaaacagt acgagaacga cgccagaacc 300
ctgtttgaat tcacttccgg cgtgaatgtt actgaatccc cgatcatcta tcgcgacgaa 360
agtatgcgta ccgcctgctc tcccgatggt ttatgcagtg acggcaacgg ccttgaactg 420
aaatgcccgt ttacctcccg ggatttcatg aagttccggc tcggtggttt cgaggccata 480
aagtcagctt acatggccca ggtgcagtac agcatgtggg tgacgcgaaa aaatgcctgg 540
tactttgcca actatgaccc gcgtatgaag cgtgaaggcc tgcattatgt cgtgattgag 600
cgggatgaaa agtacatggc gagttttgac gagatcgtgc cggagttcat cgaaaaaatg 660
gacgaggcac tggctgaaat tggttttgta tttggggagc aatggcgatc tggctctggt 720
tccggcagcg gttccgga 738

<210> SEQ ID NO 17
<211> LENGTH: 226
<212> TYPE: PRT
<213> ORGANISM: Artificial Sequence
<220> FEATURE:
<223> OTHER INFORMATION: Bacteriophage lambda exonuclease

<400> SEQUENCE: 17

Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
            20                  25                  30

Thr Ala Ser Glu Val His Asn Val Ile Ala Lys Pro Arg Ser Gly Lys
        35                  40                  45

Lys Trp Pro Asp Met Lys Met Ser Tyr Phe His Thr Leu Leu Ala Glu
    50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
        115                 120                 125

Glu Leu Lys Cys Pro Phe Thr Ser Arg Asp Phe Met Lys Phe Arg Leu
    130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp

-continued

```
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
    210                 215                 220

Trp Arg
225


<210> SEQ ID NO 18
<211> LENGTH: 760
<212> TYPE: PRT
<213> ORGANISM: Artificial Sequence
<220> FEATURE:
<223> OTHER INFORMATION: Hel308 Mbu

<400> SEQUENCE: 18

Met Met Ile Arg Glu Leu Asp Ile Pro Arg Asp Ile Ile Gly Phe Tyr
1               5                   10                  15

Glu Asp Ser Gly Ile Lys Glu Leu Tyr Pro Pro Gln Ala Glu Ala Ile
            20                  25                  30

Glu Met Gly Leu Leu Glu Lys Lys Asn Leu Leu Ala Ala Ile Pro Thr
        35                  40                  45

Ala Ser Gly Lys Thr Leu Leu Ala Glu Leu Ala Met Ile Lys Ala Ile
    50                  55                  60

Arg Glu Gly Gly Lys Ala Leu Tyr Ile Val Pro Leu Arg Ala Leu Ala
65                  70                  75                  80

Ser Glu Lys Phe Glu Arg Phe Lys Glu Leu Ala Pro Phe Gly Ile Lys
                85                  90                  95

Val Gly Ile Ser Thr Gly Asp Leu Asp Ser Arg Ala Asp Trp Leu Gly
            100                 105                 110

Val Asn Asp Ile Ile Val Ala Thr Ser Glu Lys Thr Asp Ser Leu Leu
        115                 120                 125

Arg Asn Gly Thr Ser Trp Met Asp Glu Ile Thr Thr Val Val Val Asp
    130                 135                 140

Glu Ile His Leu Leu Asp Ser Lys Asn Arg Gly Pro Thr Leu Glu Val
145                 150                 155                 160

Thr Ile Thr Lys Leu Met Arg Leu Asn Pro Asp Val Gln Val Val Ala
                165                 170                 175

Leu Ser Ala Thr Val Gly Asn Ala Arg Glu Met Ala Asp Trp Leu Gly
            180                 185                 190

Ala Ala Leu Val Leu Ser Glu Trp Arg Pro Thr Asp Leu His Glu Gly
        195                 200                 205

Val Leu Phe Gly Asp Ala Ile Asn Phe Pro Gly Ser Gln Lys Lys Ile
    210                 215                 220

Asp Arg Leu Glu Lys Asp Asp Ala Val Asn Leu Val Leu Asp Thr Ile
225                 230                 235                 240

Lys Ala Glu Gly Gln Cys Leu Val Phe Glu Ser Ser Arg Arg Asn Cys
                245                 250                 255

Ala Gly Phe Ala Lys Thr Ala Ser Ser Lys Val Ala Lys Ile Leu Asp
            260                 265                 270

Asn Asp Ile Met Ile Lys Leu Ala Gly Ile Ala Glu Glu Val Glu Ser
        275                 280                 285

Thr Gly Glu Thr Asp Thr Ala Ile Val Leu Ala Asn Cys Ile Arg Lys
```

-continued

```
    290                 295                 300

Gly Val Ala Phe His His Ala Gly Leu Asn Ser Asn His Arg Lys Leu
305                 310                 315                 320

Val Glu Asn Gly Phe Arg Gln Asn Leu Ile Lys Val Ile Ser Ser Thr
                325                 330                 335

Pro Thr Leu Ala Ala Gly Leu Asn Leu Pro Ala Arg Arg Val Ile Ile
            340                 345                 350

Arg Ser Tyr Arg Arg Phe Asp Ser Asn Phe Gly Met Gln Pro Ile Pro
        355                 360                 365

Val Leu Glu Tyr Lys Gln Met Ala Gly Arg Ala Gly Arg Pro His Leu
    370                 375                 380

Asp Pro Tyr Gly Glu Ser Val Leu Leu Ala Lys Thr Tyr Asp Glu Phe
385                 390                 395                 400

Ala Gln Leu Met Glu Asn Tyr Val Glu Ala Asp Ala Glu Asp Ile Trp
                405                 410                 415

Ser Lys Leu Gly Thr Glu Asn Ala Leu Arg Thr His Val Leu Ser Thr
            420                 425                 430

Ile Val Asn Gly Phe Ala Ser Thr Arg Gln Glu Leu Phe Asp Phe Phe
        435                 440                 445

Gly Ala Thr Phe Phe Ala Tyr Gln Gln Asp Lys Trp Met Leu Glu Glu
    450                 455                 460

Val Ile Asn Asp Cys Leu Glu Phe Leu Ile Asp Lys Ala Met Val Ser
465                 470                 475                 480

Glu Thr Glu Asp Ile Glu Asp Ala Ser Lys Leu Phe Leu Arg Gly Thr
                485                 490                 495

Arg Leu Gly Ser Leu Val Ser Met Leu Tyr Ile Asp Pro Leu Ser Gly
            500                 505                 510

Ser Lys Ile Val Asp Gly Phe Lys Asp Ile Gly Lys Ser Thr Gly Gly
        515                 520                 525

Asn Met Gly Ser Leu Glu Asp Asp Lys Gly Asp Asp Ile Thr Val Thr
    530                 535                 540

Asp Met Thr Leu Leu His Leu Val Cys Ser Thr Pro Asp Met Arg Gln
545                 550                 555                 560

Leu Tyr Leu Arg Asn Thr Asp Tyr Thr Ile Val Asn Glu Tyr Ile Val
                565                 570                 575

Ala His Ser Asp Glu Phe His Glu Ile Pro Asp Lys Leu Lys Glu Thr
            580                 585                 590

Asp Tyr Glu Trp Phe Met Gly Glu Val Lys Thr Ala Met Leu Leu Glu
        595                 600                 605

Glu Trp Val Thr Glu Val Ser Ala Glu Asp Ile Thr Arg His Phe Asn
    610                 615                 620

Val Gly Glu Gly Asp Ile His Ala Leu Ala Asp Thr Ser Glu Trp Leu
625                 630                 635                 640

Met His Ala Ala Ala Lys Leu Ala Glu Leu Leu Gly Val Glu Tyr Ser
                645                 650                 655

Ser His Ala Tyr Ser Leu Glu Lys Arg Ile Arg Tyr Gly Ser Gly Leu
            660                 665                 670

Asp Leu Met Glu Leu Val Gly Ile Arg Gly Val Gly Arg Val Arg Ala
        675                 680                 685

Arg Lys Leu Tyr Asn Ala Gly Phe Val Ser Val Ala Lys Leu Lys Gly
    690                 695                 700

Ala Asp Ile Ser Val Leu Ser Lys Leu Val Gly Pro Lys Val Ala Tyr
705                 710                 715                 720
```

-continued

```
Asn Ile Leu Ser Gly Ile Gly Val Arg Val Asn Asp Lys His Phe Asn
                725                 730                 735

Ser Ala Pro Ile Ser Ser Asn Thr Leu Asp Thr Leu Leu Asp Lys Asn
            740                 745                 750

Gln Lys Thr Phe Asn Asp Phe Gln
        755                 760
```

<210> SEQ ID NO 19
<211> LENGTH: 707
<212> TYPE: PRT
<213> ORGANISM: Artificial Sequence
<220> FEATURE:
<223> OTHER INFORMATION: Hel308 Csy

<400> SEQUENCE: 19

```
Met Arg Ile Ser Glu Leu Asp Ile Pro Arg Pro Ala Ile Glu Phe Leu
1               5                   10                  15

Glu Gly Glu Gly Tyr Lys Lys Leu Tyr Pro Pro Gln Ala Ala Ala Ala
            20                  25                  30

Lys Ala Gly Leu Thr Asp Gly Lys Ser Val Leu Val Ser Ala Pro Thr
        35                  40                  45

Ala Ser Gly Lys Thr Leu Ile Ala Ala Ile Ala Met Ile Ser His Leu
    50                  55                  60

Ser Arg Asn Arg Gly Lys Ala Val Tyr Leu Ser Pro Leu Arg Ala Leu
65                  70                  75                  80

Ala Ala Glu Lys Phe Ala Glu Phe Gly Lys Ile Gly Gly Ile Pro Leu
                85                  90                  95

Gly Arg Pro Val Arg Val Gly Val Ser Thr Gly Asp Phe Glu Lys Ala
            100                 105                 110

Gly Arg Ser Leu Gly Asn Asn Asp Ile Leu Val Leu Thr Asn Glu Arg
        115                 120                 125

Met Asp Ser Leu Ile Arg Arg Arg Pro Asp Trp Met Asp Glu Val Gly
    130                 135                 140

Leu Val Ile Ala Asp Glu Ile His Leu Ile Gly Asp Arg Ser Arg Gly
145                 150                 155                 160

Pro Thr Leu Glu Met Val Leu Thr Lys Leu Arg Gly Leu Arg Ser Ser
                165                 170                 175

Pro Gln Val Val Ala Leu Ser Ala Thr Ile Ser Asn Ala Asp Glu Ile
            180                 185                 190

Ala Gly Trp Leu Asp Cys Thr Leu Val His Ser Thr Trp Arg Pro Val
        195                 200                 205

Pro Leu Ser Glu Gly Val Tyr Gln Asp Gly Glu Val Ala Met Gly Asp
    210                 215                 220

Gly Ser Arg His Glu Val Ala Ala Thr Gly Gly Gly Pro Ala Val Asp
225                 230                 235                 240

Leu Ala Ala Glu Ser Val Ala Glu Gly Gly Gln Ser Leu Ile Phe Ala
                245                 250                 255

Asp Thr Arg Ala Arg Ser Ala Ser Leu Ala Ala Lys Ala Ser Ala Val
            260                 265                 270

Ile Pro Glu Ala Lys Gly Ala Asp Ala Ala Lys Leu Ala Ala Ala Ala
        275                 280                 285

Lys Lys Ile Ile Ser Ser Gly Gly Glu Thr Lys Leu Ala Lys Thr Leu
    290                 295                 300

Ala Glu Leu Val Glu Lys Gly Ala Ala Phe His His Ala Gly Leu Asn
305                 310                 315                 320
```

```
Gln Asp Cys Arg Ser Val Val Glu Glu Glu Phe Arg Ser Gly Arg Ile
                325                 330                 335

Arg Leu Leu Ala Ser Thr Pro Thr Leu Ala Ala Gly Val Asn Leu Pro
            340                 345                 350

Ala Arg Arg Val Val Ile Ser Ser Val Met Arg Tyr Asn Ser Ser Ser
        355                 360                 365

Gly Met Ser Glu Pro Ile Ser Ile Leu Glu Tyr Lys Gln Leu Cys Gly
    370                 375                 380

Arg Ala Gly Arg Pro Gln Tyr Asp Lys Ser Gly Glu Ala Ile Val Val
385                 390                 395                 400

Gly Gly Val Asn Ala Asp Glu Ile Phe Asp Arg Tyr Ile Gly Gly Glu
                405                 410                 415

Pro Glu Pro Ile Arg Ser Ala Met Val Asp Asp Arg Ala Leu Arg Ile
            420                 425                 430

His Val Leu Ser Leu Val Thr Thr Ser Pro Gly Ile Lys Glu Asp Asp
        435                 440                 445

Val Thr Glu Phe Phe Leu Gly Thr Leu Gly Gly Gln Gln Ser Gly Glu
    450                 455                 460

Ser Thr Val Lys Phe Ser Val Ala Val Ala Leu Arg Phe Leu Gln Glu
465                 470                 475                 480

Glu Gly Met Leu Gly Arg Arg Gly Gly Arg Leu Ala Ala Thr Lys Met
                485                 490                 495

Gly Arg Leu Val Ser Arg Leu Tyr Met Asp Pro Met Thr Ala Val Thr
            500                 505                 510

Leu Arg Asp Ala Val Gly Glu Ala Ser Pro Gly Arg Met His Thr Leu
        515                 520                 525

Gly Phe Leu His Leu Val Ser Glu Cys Ser Glu Phe Met Pro Arg Phe
    530                 535                 540

Ala Leu Arg Gln Lys Asp His Glu Val Ala Glu Met Met Leu Glu Ala
545                 550                 555                 560

Gly Arg Gly Glu Leu Leu Arg Pro Val Tyr Ser Tyr Glu Cys Gly Arg
                565                 570                 575

Gly Leu Leu Ala Leu His Arg Trp Ile Gly Glu Ser Pro Glu Ala Lys
            580                 585                 590

Leu Ala Glu Asp Leu Lys Phe Glu Ser Gly Asp Val His Arg Met Val
        595                 600                 605

Glu Ser Ser Gly Trp Leu Leu Arg Cys Ile Trp Glu Ile Ser Lys His
    610                 615                 620

Gln Glu Arg Pro Asp Leu Leu Gly Glu Leu Asp Val Leu Arg Ser Arg
625                 630                 635                 640

Val Ala Tyr Gly Ile Lys Ala Glu Leu Val Pro Leu Val Ser Ile Lys
                645                 650                 655

Gly Ile Gly Arg Val Arg Ser Arg Arg Leu Phe Arg Gly Gly Ile Lys
            660                 665                 670

Gly Pro Gly Asp Leu Ala Ala Val Pro Val Glu Arg Leu Ser Arg Val
        675                 680                 685

Glu Gly Ile Gly Ala Thr Leu Ala Asn Asn Ile Lys Ser Gln Leu Arg
    690                 695                 700

Lys Gly Gly
705
```

<210> SEQ ID NO 20
<211> LENGTH: 720

<212> TYPE: PRT
<213> ORGANISM: Artificial Sequence
<220> FEATURE:
<223> OTHER INFORMATION: Hel308 Tga

<400> SEQUENCE: 20

```
Met Lys Val Asp Glu Leu Pro Val Asp Glu Arg Leu Lys Ala Val Leu
1               5                   10                  15

Lys Glu Arg Gly Ile Glu Glu Leu Tyr Pro Pro Gln Ala Glu Ala Leu
            20                  25                  30

Lys Ser Gly Ala Leu Glu Gly Arg Asn Leu Val Leu Ala Ile Pro Thr
        35                  40                  45

Ala Ser Gly Lys Thr Leu Val Ser Glu Ile Val Met Val Asn Lys Leu
    50                  55                  60

Ile Gln Glu Gly Gly Lys Ala Val Tyr Leu Val Pro Leu Lys Ala Leu
65                  70                  75                  80

Ala Glu Glu Lys Tyr Arg Glu Phe Lys Glu Trp Glu Lys Leu Gly Leu
                85                  90                  95

Lys Val Ala Ala Thr Thr Gly Asp Tyr Asp Ser Thr Asp Asp Trp Leu
            100                 105                 110

Gly Arg Tyr Asp Ile Ile Val Ala Thr Ala Glu Lys Phe Asp Ser Leu
        115                 120                 125

Leu Arg His Gly Ala Arg Trp Ile Asn Asp Val Lys Leu Val Val Ala
    130                 135                 140

Asp Glu Val His Leu Ile Gly Ser Tyr Asp Arg Gly Ala Thr Leu Glu
145                 150                 155                 160

Met Ile Leu Thr His Met Leu Gly Arg Ala Gln Ile Leu Ala Leu Ser
                165                 170                 175

Ala Thr Val Gly Asn Ala Glu Glu Leu Ala Glu Trp Leu Asp Ala Ser
            180                 185                 190

Leu Val Val Ser Asp Trp Arg Pro Val Gln Leu Arg Arg Gly Val Phe
        195                 200                 205

His Leu Gly Thr Leu Ile Trp Glu Asp Gly Lys Val Glu Ser Tyr Pro
    210                 215                 220

Glu Asn Trp Tyr Ser Leu Val Val Asp Ala Val Lys Arg Gly Lys Gly
225                 230                 235                 240

Ala Leu Val Phe Val Asn Thr Arg Arg Ser Ala Glu Lys Glu Ala Leu
                245                 250                 255

Ala Leu Ser Lys Leu Val Ser Ser His Leu Thr Lys Pro Glu Lys Arg
            260                 265                 270

Ala Leu Glu Ser Leu Ala Ser Gln Leu Glu Asp Asn Pro Thr Ser Glu
        275                 280                 285

Lys Leu Lys Arg Ala Leu Arg Gly Gly Val Ala Phe His His Ala Gly
    290                 295                 300

Leu Ser Arg Val Glu Arg Thr Leu Ile Glu Asp Ala Phe Arg Glu Gly
305                 310                 315                 320

Leu Ile Lys Val Ile Thr Ala Thr Pro Thr Leu Ser Ala Gly Val Asn
                325                 330                 335

Leu Pro Ser Phe Arg Val Ile Ile Arg Asp Thr Lys Arg Tyr Ala Gly
            340                 345                 350

Phe Gly Trp Thr Asp Ile Pro Val Leu Glu Ile Gln Gln Met Met Gly
        355                 360                 365

Arg Ala Gly Arg Pro Arg Tyr Asp Lys Tyr Gly Glu Ala Ile Ile Val
    370                 375                 380
```

-continued

```
Ala Arg Thr Asp Glu Pro Gly Lys Leu Met Glu Arg Tyr Ile Arg Gly
385                 390                 395                 400

Lys Pro Glu Lys Leu Phe Ser Met Leu Ala Asn Glu Gln Ala Phe Arg
                405                 410                 415

Ser Gln Val Leu Ala Leu Ile Thr Asn Phe Gly Ile Arg Ser Phe Pro
            420                 425                 430

Glu Leu Val Arg Phe Leu Glu Arg Thr Phe Tyr Ala His Gln Arg Lys
        435                 440                 445

Asp Leu Ser Ser Leu Glu Tyr Lys Ala Lys Glu Val Val Tyr Phe Leu
    450                 455                 460

Ile Glu Asn Glu Phe Ile Asp Leu Asp Leu Glu Asp Arg Phe Ile Pro
465                 470                 475                 480

Leu Pro Phe Gly Lys Arg Thr Ser Gln Leu Tyr Ile Asp Pro Leu Thr
                485                 490                 495

Ala Lys Lys Phe Lys Asp Ala Phe Pro Ala Ile Glu Arg Asn Pro Asn
            500                 505                 510

Pro Phe Gly Ile Phe Gln Leu Ile Ala Ser Thr Pro Asp Met Ala Thr
        515                 520                 525

Leu Thr Ala Arg Arg Arg Glu Met Glu Asp Tyr Leu Asp Leu Ala Tyr
    530                 535                 540

Glu Leu Glu Asp Lys Leu Tyr Ala Ser Ile Pro Tyr Tyr Glu Asp Ser
545                 550                 555                 560

Arg Phe Gln Gly Phe Leu Gly Gln Val Lys Thr Ala Lys Val Leu Leu
                565                 570                 575

Asp Trp Ile Asn Glu Val Pro Glu Ala Arg Ile Tyr Glu Thr Tyr Ser
            580                 585                 590

Ile Asp Pro Gly Asp Leu Tyr Arg Leu Leu Glu Leu Ala Asp Trp Leu
        595                 600                 605

Met Tyr Ser Leu Ile Glu Leu Tyr Lys Leu Phe Glu Pro Lys Glu Glu
    610                 615                 620

Ile Leu Asn Tyr Leu Arg Asp Leu His Leu Arg Leu Arg His Gly Val
625                 630                 635                 640

Arg Glu Glu Leu Leu Glu Leu Val Arg Leu Pro Asn Ile Gly Arg Lys
                645                 650                 655

Arg Ala Arg Ala Leu Tyr Asn Ala Gly Phe Arg Ser Val Glu Ala Ile
            660                 665                 670

Ala Asn Ala Lys Pro Ala Glu Leu Leu Ala Val Glu Gly Ile Gly Ala
        675                 680                 685

Lys Ile Leu Asp Gly Ile Tyr Arg His Leu Gly Ile Glu Lys Arg Val
    690                 695                 700

Thr Glu Glu Lys Pro Lys Arg Lys Gly Thr Leu Glu Asp Phe Leu Arg
705                 710                 715                 720


<210> SEQ ID NO 21
<211> LENGTH: 799
<212> TYPE: PRT
<213> ORGANISM: Artificial Sequence
<220> FEATURE:
<223> OTHER INFORMATION: Hel308 Mhu

<400> SEQUENCE: 21

Met Glu Ile Ala Ser Leu Pro Leu Pro Asp Ser Phe Ile Arg Ala Cys
1               5                   10                  15

His Ala Lys Gly Ile Arg Ser Leu Tyr Pro Pro Gln Ala Glu Cys Ile
            20                  25                  30
```

-continued

```
Glu Lys Gly Leu Leu Glu Gly Lys Asn Leu Leu Ile Ser Ile Pro Thr
        35                  40                  45

Ala Ser Gly Lys Thr Leu Leu Ala Glu Met Ala Met Trp Ser Arg Ile
    50                  55                  60

Ala Ala Gly Gly Lys Cys Leu Tyr Ile Val Pro Leu Arg Ala Leu Ala
65                  70                  75                  80

Ser Glu Lys Tyr Asp Glu Phe Ser Lys Lys Gly Val Ile Arg Val Gly
                85                  90                  95

Ile Ala Thr Gly Asp Leu Asp Arg Thr Asp Ala Tyr Leu Gly Glu Asn
            100                 105                 110

Asp Ile Ile Val Ala Thr Ser Glu Lys Thr Asp Ser Leu Leu Arg Asn
        115                 120                 125

Arg Thr Pro Trp Leu Ser Gln Ile Thr Cys Ile Val Leu Asp Glu Val
    130                 135                 140

His Leu Ile Gly Ser Glu Asn Arg Gly Ala Thr Leu Glu Met Val Ile
145                 150                 155                 160

Thr Lys Leu Arg Tyr Thr Asn Pro Val Met Gln Ile Ile Gly Leu Ser
                165                 170                 175

Ala Thr Ile Gly Asn Pro Ala Gln Leu Ala Glu Trp Leu Asp Ala Thr
            180                 185                 190

Leu Ile Thr Ser Thr Trp Arg Pro Val Asp Leu Arg Gln Gly Val Tyr
        195                 200                 205

Tyr Asn Gly Lys Ile Arg Phe Ser Asp Ser Glu Arg Pro Ile Gln Gly
    210                 215                 220

Lys Thr Lys His Asp Asp Leu Asn Leu Cys Leu Asp Thr Ile Glu Glu
225                 230                 235                 240

Gly Gly Gln Cys Leu Val Phe Val Ser Ser Arg Arg Asn Ala Glu Gly
                245                 250                 255

Phe Ala Lys Lys Ala Ala Gly Ala Leu Lys Ala Gly Ser Pro Asp Ser
            260                 265                 270

Lys Ala Leu Ala Gln Glu Leu Arg Arg Leu Arg Asp Arg Asp Glu Gly
        275                 280                 285

Asn Val Leu Ala Asp Cys Val Glu Arg Gly Ala Ala Phe His His Ala
    290                 295                 300

Gly Leu Ile Arg Gln Glu Arg Thr Ile Ile Glu Glu Gly Phe Arg Asn
305                 310                 315                 320

Gly Tyr Ile Glu Val Ile Ala Ala Thr Pro Thr Leu Ala Ala Gly Leu
                325                 330                 335

Asn Leu Pro Ala Arg Arg Val Ile Ile Arg Asp Tyr Asn Arg Phe Ala
            340                 345                 350

Ser Gly Leu Gly Met Val Pro Ile Pro Val Gly Glu Tyr His Gln Met
        355                 360                 365

Ala Gly Arg Ala Gly Arg Pro His Leu Asp Pro Tyr Gly Glu Ala Val
    370                 375                 380

Leu Leu Ala Lys Asp Ala Pro Ser Val Glu Arg Leu Phe Glu Thr Phe
385                 390                 395                 400

Ile Asp Ala Glu Ala Glu Arg Val Asp Ser Gln Cys Val Asp Asp Ala
                405                 410                 415

Ser Leu Cys Ala His Ile Leu Ser Leu Ile Ala Thr Gly Phe Ala His
            420                 425                 430

Asp Gln Glu Ala Leu Ser Ser Phe Met Glu Arg Thr Phe Tyr Phe Phe
        435                 440                 445

Gln His Pro Lys Thr Arg Ser Leu Pro Arg Leu Val Ala Asp Ala Ile
```

-continued

```
    450                 455                 460

Arg Phe Leu Thr Thr Ala Gly Met Val Glu Glu Arg Glu Asn Thr Leu
465                 470                 475                 480

Ser Ala Thr Arg Leu Gly Ser Leu Val Ser Arg Leu Tyr Leu Asn Pro
                485                 490                 495

Cys Thr Ala Arg Leu Ile Leu Asp Ser Leu Lys Ser Cys Lys Thr Pro
            500                 505                 510

Thr Leu Ile Gly Leu Leu His Val Ile Cys Val Ser Pro Asp Met Gln
        515                 520                 525

Arg Leu Tyr Leu Lys Ala Ala Asp Thr Gln Leu Leu Arg Thr Phe Leu
    530                 535                 540

Phe Lys His Lys Asp Asp Leu Ile Leu Pro Leu Pro Phe Glu Gln Glu
545                 550                 555                 560

Glu Glu Glu Leu Trp Leu Ser Gly Leu Lys Thr Ala Leu Val Leu Thr
                565                 570                 575

Asp Trp Ala Asp Glu Phe Ser Glu Gly Met Ile Glu Glu Arg Tyr Gly
            580                 585                 590

Ile Gly Ala Gly Asp Leu Tyr Asn Ile Val Asp Ser Gly Lys Trp Leu
        595                 600                 605

Leu His Gly Thr Glu Arg Leu Val Ser Val Glu Met Pro Glu Met Ser
    610                 615                 620

Gln Val Val Lys Thr Leu Ser Val Arg Val His His Gly Val Lys Ser
625                 630                 635                 640

Glu Leu Leu Pro Leu Val Ala Leu Arg Asn Ile Gly Arg Val Arg Ala
                645                 650                 655

Arg Thr Leu Tyr Asn Ala Gly Tyr Pro Asp Pro Glu Ala Val Ala Arg
            660                 665                 670

Ala Gly Leu Ser Thr Ile Ala Arg Ile Ile Gly Glu Gly Ile Ala Arg
        675                 680                 685

Gln Val Ile Asp Glu Ile Thr Gly Val Lys Arg Ser Gly Ile His Ser
    690                 695                 700

Ser Asp Asp Asp Tyr Gln Gln Lys Thr Pro Glu Leu Leu Thr Asp Ile
705                 710                 715                 720

Pro Gly Ile Gly Lys Lys Met Ala Glu Lys Leu Gln Asn Ala Gly Ile
                725                 730                 735

Ile Thr Val Ser Asp Leu Leu Thr Ala Asp Glu Val Leu Leu Ser Asp
            740                 745                 750

Val Leu Gly Ala Ala Arg Ala Arg Lys Val Leu Ala Phe Leu Ser Asn
        755                 760                 765

Ser Glu Lys Glu Asn Ser Ser Ser Asp Lys Thr Glu Glu Ile Pro Asp
    770                 775                 780

Thr Gln Lys Ile Arg Gly Gln Ser Ser Trp Glu Asp Phe Gly Cys
785                 790                 795


<210> SEQ ID NO 22
<211> LENGTH: 1756
<212> TYPE: PRT
<213> ORGANISM: Artificial Sequence
<220> FEATURE:
<223> OTHER INFORMATION: TraI Eco

<400> SEQUENCE: 22

Met Met Ser Ile Ala Gln Val Arg Ser Ala Gly Ser Ala Gly Asn Tyr
1               5                   10                  15

Tyr Thr Asp Lys Asp Asn Tyr Tyr Val Leu Gly Ser Met Gly Glu Arg
```

-continued

```
            20                  25                  30

Trp Ala Gly Lys Gly Ala Glu Gln Leu Gly Leu Gln Gly Ser Val Asp
        35                  40                  45

Lys Asp Val Phe Thr Arg Leu Leu Glu Gly Arg Leu Pro Asp Gly Ala
    50                  55                  60

Asp Leu Ser Arg Met Gln Asp Gly Ser Asn Lys His Arg Pro Gly Tyr
65                  70                  75                  80

Asp Leu Thr Phe Ser Ala Pro Lys Ser Val Ser Met Met Ala Met Leu
                85                  90                  95

Gly Gly Asp Lys Arg Leu Ile Asp Ala His Asn Gln Ala Val Asp Phe
            100                 105                 110

Ala Val Arg Gln Val Glu Ala Leu Ala Ser Thr Arg Val Met Thr Asp
        115                 120                 125

Gly Gln Ser Glu Thr Val Leu Thr Gly Asn Leu Val Met Ala Leu Phe
    130                 135                 140

Asn His Asp Thr Ser Arg Asp Gln Glu Pro Gln Leu His Thr His Ala
145                 150                 155                 160

Val Val Ala Asn Val Thr Gln His Asn Gly Glu Trp Lys Thr Leu Ser
                165                 170                 175

Ser Asp Lys Val Gly Lys Thr Gly Phe Ile Glu Asn Val Tyr Ala Asn
            180                 185                 190

Gln Ile Ala Phe Gly Arg Leu Tyr Arg Glu Lys Leu Lys Glu Gln Val
        195                 200                 205

Glu Ala Leu Gly Tyr Glu Thr Glu Val Val Gly Lys His Gly Met Trp
    210                 215                 220

Glu Met Pro Gly Val Pro Val Glu Ala Phe Ser Gly Arg Ser Gln Ala
225                 230                 235                 240

Ile Arg Glu Ala Val Gly Glu Asp Ala Ser Leu Lys Ser Arg Asp Val
                245                 250                 255

Ala Ala Leu Asp Thr Arg Lys Ser Lys Gln His Val Asp Pro Glu Ile
            260                 265                 270

Arg Met Ala Glu Trp Met Gln Thr Leu Lys Glu Thr Gly Phe Asp Ile
        275                 280                 285

Arg Ala Tyr Arg Asp Ala Ala Asp Gln Arg Thr Glu Ile Arg Thr Gln
    290                 295                 300

Ala Pro Gly Pro Ala Ser Gln Asp Gly Pro Asp Val Gln Gln Ala Val
305                 310                 315                 320

Thr Gln Ala Ile Ala Gly Leu Ser Glu Arg Lys Val Gln Phe Thr Tyr
                325                 330                 335

Thr Asp Val Leu Ala Arg Thr Val Gly Ile Leu Pro Pro Glu Asn Gly
            340                 345                 350

Val Ile Glu Arg Ala Arg Ala Gly Ile Asp Glu Ala Ile Ser Arg Glu
        355                 360                 365

Gln Leu Ile Pro Leu Asp Arg Glu Lys Gly Leu Phe Thr Ser Gly Ile
    370                 375                 380

His Val Leu Asp Glu Leu Ser Val Arg Ala Leu Ser Arg Asp Ile Met
385                 390                 395                 400

Lys Gln Asn Arg Val Thr Val His Pro Glu Lys Ser Val Pro Arg Thr
                405                 410                 415

Ala Gly Tyr Ser Asp Ala Val Ser Val Leu Ala Gln Asp Arg Pro Ser
            420                 425                 430

Leu Ala Ile Val Ser Gly Gln Gly Gly Ala Ala Gly Gln Arg Glu Arg
        435                 440                 445
```

-continued

```
Val Ala Glu Leu Val Met Met Ala Arg Glu Gln Gly Arg Glu Val Gln
    450                 455                 460

Ile Ile Ala Ala Asp Arg Arg Ser Gln Met Asn Leu Lys Gln Asp Glu
465                 470                 475                 480

Arg Leu Ser Gly Glu Leu Ile Thr Gly Arg Arg Gln Leu Leu Glu Gly
                485                 490                 495

Met Ala Phe Thr Pro Gly Ser Thr Val Ile Val Asp Gln Gly Glu Lys
            500                 505                 510

Leu Ser Leu Lys Glu Thr Leu Thr Leu Leu Asp Gly Ala Ala Arg His
        515                 520                 525

Asn Val Gln Val Leu Ile Thr Asp Ser Gly Gln Arg Thr Gly Thr Gly
    530                 535                 540

Ser Ala Leu Met Ala Met Lys Asp Ala Gly Val Asn Thr Tyr Arg Trp
545                 550                 555                 560

Gln Gly Gly Glu Gln Arg Pro Ala Thr Ile Ile Ser Glu Pro Asp Arg
                565                 570                 575

Asn Val Arg Tyr Ala Arg Leu Ala Gly Asp Phe Ala Ala Ser Val Lys
            580                 585                 590

Ala Gly Glu Glu Ser Val Ala Gln Val Ser Gly Val Arg Glu Gln Ala
        595                 600                 605

Ile Leu Thr Gln Ala Ile Arg Ser Glu Leu Lys Thr Gln Gly Val Leu
    610                 615                 620

Gly His Pro Glu Val Thr Met Thr Ala Leu Ser Pro Val Trp Leu Asp
625                 630                 635                 640

Ser Arg Ser Arg Tyr Leu Arg Asp Met Tyr Arg Pro Gly Met Val Met
                645                 650                 655

Glu Gln Trp Asn Pro Glu Thr Arg Ser His Asp Arg Tyr Val Ile Asp
            660                 665                 670

Arg Val Thr Ala Gln Ser His Ser Leu Thr Leu Arg Asp Ala Gln Gly
        675                 680                 685

Glu Thr Gln Val Val Arg Ile Ser Ser Leu Asp Ser Ser Trp Ser Leu
    690                 695                 700

Phe Arg Pro Glu Lys Met Pro Val Ala Asp Gly Glu Arg Leu Arg Val
705                 710                 715                 720

Thr Gly Lys Ile Pro Gly Leu Arg Val Ser Gly Gly Asp Arg Leu Gln
                725                 730                 735

Val Ala Ser Val Ser Glu Asp Ala Met Thr Val Val Val Pro Gly Arg
            740                 745                 750

Ala Glu Pro Ala Ser Leu Pro Val Ser Asp Ser Pro Phe Thr Ala Leu
        755                 760                 765

Lys Leu Glu Asn Gly Trp Val Glu Thr Pro Gly His Ser Val Ser Asp
    770                 775                 780

Ser Ala Thr Val Phe Ala Ser Val Thr Gln Met Ala Met Asp Asn Ala
785                 790                 795                 800

Thr Leu Asn Gly Leu Ala Arg Ser Gly Arg Asp Val Arg Leu Tyr Ser
                805                 810                 815

Ser Leu Asp Glu Thr Arg Thr Ala Glu Lys Leu Ala Arg His Pro Ser
            820                 825                 830

Phe Thr Val Val Ser Glu Gln Ile Lys Ala Arg Ala Gly Glu Thr Leu
        835                 840                 845

Leu Glu Thr Ala Ile Ser Leu Gln Lys Ala Gly Leu His Thr Pro Ala
    850                 855                 860
```

-continued

```
Gln Gln Ala Ile His Leu Ala Leu Pro Val Leu Glu Ser Lys Asn Leu
865                 870                 875                 880

Ala Phe Ser Met Val Asp Leu Leu Thr Glu Ala Lys Ser Phe Ala Ala
                885                 890                 895

Glu Gly Thr Gly Phe Thr Glu Leu Gly Gly Glu Ile Asn Ala Gln Ile
            900                 905                 910

Lys Arg Gly Asp Leu Leu Tyr Val Asp Val Ala Lys Gly Tyr Gly Thr
        915                 920                 925

Gly Leu Leu Val Ser Arg Ala Ser Tyr Glu Ala Glu Lys Ser Ile Leu
    930                 935                 940

Arg His Ile Leu Glu Gly Lys Glu Ala Val Thr Pro Leu Met Glu Arg
945                 950                 955                 960

Val Pro Gly Glu Leu Met Glu Thr Leu Thr Ser Gly Gln Arg Ala Ala
                965                 970                 975

Thr Arg Met Ile Leu Glu Thr Ser Asp Arg Phe Thr Val Val Gln Gly
            980                 985                 990

Tyr Ala Gly Val Gly Lys Thr Thr  Gln Phe Arg Ala Val  Met Ser Ala
        995                 1000                 1005

Val Asn  Met Leu Pro Ala Ser  Glu Arg Pro Arg Val  Val Gly Leu
    1010                 1015                 1020

Gly Pro  Thr His Arg Ala Val  Gly Glu Met Arg Ser  Ala Gly Val
    1025                 1030                 1035

Asp Ala  Gln Thr Leu Ala Ser  Phe Leu His Asp Thr  Gln Leu Gln
    1040                 1045                 1050

Gln Arg  Ser Gly Glu Thr Pro  Asp Phe Ser Asn Thr  Leu Phe Leu
    1055                 1060                 1065

Leu Asp  Glu Ser Ser Met Val  Gly Asn Thr Glu Met  Ala Arg Ala
    1070                 1075                 1080

Tyr Ala  Leu Ile Ala Ala Gly  Gly Gly Arg Ala Val  Ala Ser Gly
    1085                 1090                 1095

Asp Thr  Asp Gln Leu Gln Ala  Ile Ala Pro Gly Gln  Ser Phe Arg
    1100                 1105                 1110

Leu Gln  Gln Thr Arg Ser Ala  Ala Asp Val Val Ile  Met Lys Glu
    1115                 1120                 1125

Ile Val  Arg Gln Thr Pro Glu  Leu Arg Glu Ala Val  Tyr Ser Leu
    1130                 1135                 1140

Ile Asn  Arg Asp Val Glu Arg  Ala Leu Ser Gly Leu  Glu Ser Val
    1145                 1150                 1155

Lys Pro  Ser Gln Val Pro Arg  Leu Glu Gly Ala Trp  Ala Pro Glu
    1160                 1165                 1170

His Ser  Val Thr Glu Phe Ser  His Ser Gln Glu Ala  Lys Leu Ala
    1175                 1180                 1185

Glu Ala  Gln Gln Lys Ala Met  Leu Lys Gly Glu Ala  Phe Pro Asp
    1190                 1195                 1200

Ile Pro  Met Thr Leu Tyr Glu  Ala Ile Val Arg Asp  Tyr Thr Gly
    1205                 1210                 1215

Arg Thr  Pro Glu Ala Arg Glu  Gln Thr Leu Ile Val  Thr His Leu
    1220                 1225                 1230

Asn Glu  Asp Arg Arg Val Leu  Asn Ser Met Ile His  Asp Ala Arg
    1235                 1240                 1245

Glu Lys  Ala Gly Glu Leu Gly  Lys Glu Gln Val Met  Val Pro Val
    1250                 1255                 1260

Leu Asn  Thr Ala Asn Ile Arg  Asp Gly Glu Leu Arg  Arg Leu Ser
```

-continued

```
    1265                1270                1275

Thr Trp  Glu Lys Asn Pro Asp  Ala Leu Ala Leu Val  Asp Asn Val
    1280                1285                1290

Tyr His  Arg Ile Ala Gly Ile  Ser Lys Asp Asp Gly  Leu Ile Thr
    1295                1300                1305

Leu Gln  Asp Ala Glu Gly Asn  Thr Arg Leu Ile Ser  Pro Arg Glu
    1310                1315                1320

Ala Val  Ala Glu Gly Val Thr  Leu Tyr Thr Pro Asp  Lys Ile Arg
    1325                1330                1335

Val Gly  Thr Gly Asp Arg Met  Arg Phe Thr Lys Ser  Asp Arg Glu
    1340                1345                1350

Arg Gly  Tyr Val Ala Asn Ser  Val Trp Thr Val Thr  Ala Val Ser
    1355                1360                1365

Gly Asp  Ser Val Thr Leu Ser  Asp Gly Gln Gln Thr  Arg Val Ile
    1370                1375                1380

Arg Pro  Gly Gln Glu Arg Ala  Glu Gln His Ile Asp  Leu Ala Tyr
    1385                1390                1395

Ala Ile  Thr Ala His Gly Ala  Gln Gly Ala Ser Glu  Thr Phe Ala
    1400                1405                1410

Ile Ala  Leu Glu Gly Thr Glu  Gly Asn Arg Lys Leu  Met Ala Gly
    1415                1420                1425

Phe Glu  Ser Ala Tyr Val Ala  Leu Ser Arg Met Lys  Gln His Val
    1430                1435                1440

Gln Val  Tyr Thr Asp Asn Arg  Gln Gly Trp Thr Asp  Ala Ile Asn
    1445                1450                1455

Asn Ala  Val Gln Lys Gly Thr  Ala His Asp Val Leu  Glu Pro Lys
    1460                1465                1470

Pro Asp  Arg Glu Val Met Asn  Ala Gln Arg Leu Phe  Ser Thr Ala
    1475                1480                1485

Arg Glu  Leu Arg Asp Val Ala  Ala Gly Arg Ala Val  Leu Arg Gln
    1490                1495                1500

Ala Gly  Leu Ala Gly Gly Asp  Ser Pro Ala Arg Phe  Ile Ala Pro
    1505                1510                1515

Gly Arg  Lys Tyr Pro Gln Pro  Tyr Val Ala Leu Pro  Ala Phe Asp
    1520                1525                1530

Arg Asn  Gly Lys Ser Ala Gly  Ile Trp Leu Asn Pro  Leu Thr Thr
    1535                1540                1545

Asp Asp  Gly Asn Gly Leu Arg  Gly Phe Ser Gly Glu  Gly Arg Val
    1550                1555                1560

Lys Gly  Ser Gly Asp Ala Gln  Phe Val Ala Leu Gln  Gly Ser Arg
    1565                1570                1575

Asn Gly  Glu Ser Leu Leu Ala  Asp Asn Met Gln Asp  Gly Val Arg
    1580                1585                1590

Ile Ala  Arg Asp Asn Pro Asp  Ser Gly Val Val Val  Arg Ile Ala
    1595                1600                1605

Gly Glu  Gly Arg Pro Trp Asn  Pro Gly Ala Ile Thr  Gly Gly Arg
    1610                1615                1620

Val Trp  Gly Asp Ile Pro Asp  Asn Ser Val Gln Pro  Gly Ala Gly
    1625                1630                1635

Asn Gly  Glu Pro Val Thr Ala  Glu Val Leu Ala Gln  Arg Gln Ala
    1640                1645                1650

Glu Glu  Ala Ile Arg Arg Glu  Thr Glu Arg Arg Ala  Asp Glu Ile
    1655                1660                1665
```

```
Val Arg  Lys Met Ala Glu Asn  Lys Pro Asp Leu Pro  Asp Gly Lys
    1670                 1675                 1680

Thr Glu  Leu Ala Val Arg Asp  Ile Ala Gly Gln Glu  Arg Asp Arg
    1685                 1690                 1695

Ser Ala  Ile Ser Glu Arg Glu  Thr Ala Leu Pro Glu  Ser Val Leu
    1700                 1705                 1710

Arg Glu  Ser Gln Arg Glu Arg  Glu Ala Val Arg Glu  Val Ala Arg
    1715                 1720                 1725

Glu Asn  Leu Leu Gln Glu Arg  Leu Gln Gln Met Glu  Arg Asp Met
    1730                 1735                 1740

Val Arg  Asp Leu Gln Lys Glu  Lys Thr Leu Gly Gly  Asp
    1745                 1750                 1755


<210> SEQ ID NO 23
<211> LENGTH: 726
<212> TYPE: PRT
<213> ORGANISM: Artificial Sequence
<220> FEATURE:
<223> OTHER INFORMATION: XPD Mbu

<400> SEQUENCE: 23

Met Ser Asp Lys Pro Ala Phe Met Lys Tyr Phe Thr Gln Ser Ser Cys
1               5                   10                  15

Tyr Pro Asn Gln Gln Glu Ala Met Asp Arg Ile His Ser Ala Leu Met
            20                  25                  30

Gln Gln Gln Leu Val Leu Phe Glu Gly Ala Cys Gly Thr Gly Lys Thr
        35                  40                  45

Leu Ser Ala Leu Val Pro Ala Leu His Val Gly Lys Met Leu Gly Lys
    50                  55                  60

Thr Val Ile Ile Ala Thr Asn Val His Gln Gln Met Val Gln Phe Ile
65                  70                  75                  80

Asn Glu Ala Arg Asp Ile Lys Lys Val Gln Asp Val Lys Val Ala Val
                85                  90                  95

Ile Lys Gly Lys Thr Ala Met Cys Pro Gln Glu Ala Asp Tyr Glu Glu
            100                 105                 110

Cys Ser Val Lys Arg Glu Asn Thr Phe Glu Leu Met Glu Thr Glu Arg
        115                 120                 125

Glu Ile Tyr Leu Lys Arg Gln Glu Leu Asn Ser Ala Arg Asp Ser Tyr
    130                 135                 140

Lys Lys Ser His Asp Pro Ala Phe Val Thr Leu Arg Asp Glu Leu Ser
145                 150                 155                 160

Lys Glu Ile Asp Ala Val Glu Glu Lys Ala Arg Gly Leu Arg Asp Arg
                165                 170                 175

Ala Cys Asn Asp Leu Tyr Glu Val Leu Arg Ser Asp Ser Glu Lys Phe
            180                 185                 190

Arg Glu Trp Leu Tyr Lys Glu Val Arg Ser Pro Glu Glu Ile Asn Asp
        195                 200                 205

His Ala Ile Lys Asp Gly Met Cys Gly Tyr Glu Leu Val Lys Arg Glu
    210                 215                 220

Leu Lys His Ala Asp Leu Leu Ile Cys Asn Tyr His His Val Leu Asn
225                 230                 235                 240

Pro Asp Ile Phe Ser Thr Val Leu Gly Trp Ile Glu Lys Glu Pro Gln
                245                 250                 255

Glu Thr Ile Val Ile Phe Asp Glu Ala His Asn Leu Glu Ser Ala Ala
            260                 265                 270
```

-continued

```
Arg Ser His Ser Ser Leu Ser Leu Thr Glu His Ser Ile Glu Lys Ala
        275                 280                 285

Ile Thr Glu Leu Glu Ala Asn Leu Asp Leu Leu Ala Asp Asp Asn Ile
    290                 295                 300

His Asn Leu Phe Asn Ile Phe Leu Glu Val Ile Ser Asp Thr Tyr Asn
305                 310                 315                 320

Ser Arg Phe Lys Phe Gly Glu Arg Glu Arg Val Arg Lys Asn Trp Tyr
                325                 330                 335

Asp Ile Arg Ile Ser Asp Pro Tyr Glu Arg Asn Asp Ile Val Arg Gly
            340                 345                 350

Lys Phe Leu Arg Gln Ala Lys Gly Asp Phe Gly Glu Lys Asp Asp Ile
        355                 360                 365

Gln Ile Leu Leu Ser Glu Ala Ser Glu Leu Gly Ala Lys Leu Asp Glu
    370                 375                 380

Thr Tyr Arg Asp Gln Tyr Lys Lys Gly Leu Ser Ser Val Met Lys Arg
385                 390                 395                 400

Ser His Ile Arg Tyr Val Ala Asp Phe Met Ser Ala Tyr Ile Glu Leu
                405                 410                 415

Ser His Asn Leu Asn Tyr Tyr Pro Ile Leu Asn Val Arg Arg Asp Met
            420                 425                 430

Asn Asp Glu Ile Tyr Gly Arg Val Glu Leu Phe Thr Cys Ile Pro Lys
        435                 440                 445

Asn Val Thr Glu Pro Leu Phe Asn Ser Leu Phe Ser Val Ile Leu Met
    450                 455                 460

Ser Ala Thr Leu His Pro Phe Glu Met Val Lys Lys Thr Leu Gly Ile
465                 470                 475                 480

Thr Arg Asp Thr Cys Glu Met Ser Tyr Gly Thr Ser Phe Pro Glu Glu
                485                 490                 495

Lys Arg Leu Ser Ile Ala Val Ser Ile Pro Pro Leu Phe Ala Lys Asn
            500                 505                 510

Arg Asp Asp Arg His Val Thr Glu Leu Leu Glu Gln Val Leu Leu Asp
        515                 520                 525

Ser Ile Glu Asn Ser Lys Gly Asn Val Ile Leu Phe Phe Gln Ser Ala
    530                 535                 540

Phe Glu Ala Lys Arg Tyr Tyr Ser Lys Ile Glu Pro Leu Val Asn Val
545                 550                 555                 560

Pro Val Phe Leu Asp Glu Val Gly Ile Ser Ser Gln Asp Val Arg Glu
                565                 570                 575

Glu Phe Phe Ser Ile Gly Glu Glu Asn Gly Lys Ala Val Leu Leu Ser
            580                 585                 590

Tyr Leu Trp Gly Thr Leu Ser Glu Gly Ile Asp Tyr Arg Asp Gly Arg
        595                 600                 605

Gly Arg Thr Val Ile Ile Ile Gly Val Gly Tyr Pro Ala Leu Asn Asp
    610                 615                 620

Arg Met Asn Ala Val Glu Ser Ala Tyr Asp His Val Phe Gly Tyr Gly
625                 630                 635                 640

Ala Gly Trp Glu Phe Ala Ile Gln Val Pro Thr Ile Arg Lys Ile Arg
                645                 650                 655

Gln Ala Met Gly Arg Val Val Arg Ser Pro Thr Asp Tyr Gly Ala Arg
            660                 665                 670

Ile Leu Leu Asp Gly Arg Phe Leu Thr Asp Ser Lys Lys Arg Phe Gly
        675                 680                 685
```

-continued

```
Lys Phe Ser Val Phe Glu Val Phe Pro Pro Ala Glu Arg Ser Glu Phe
    690                 695                 700

Val Asp Val Asp Pro Glu Lys Val Lys Tyr Ser Leu Met Asn Phe Phe
705                 710                 715                 720

Met Asp Asn Asp Glu Gln
                725


<210> SEQ ID NO 24
<211> LENGTH: 439
<212> TYPE: PRT
<213> ORGANISM: Artificial Sequence
<220> FEATURE:
<223> OTHER INFORMATION: Dda 1993

<400> SEQUENCE: 24

Met Thr Phe Asp Asp Leu Thr Glu Gly Gln Lys Asn Ala Phe Asn Ile
1               5                   10                  15

Val Met Lys Ala Ile Lys Glu Lys Lys His His Val Thr Ile Asn Gly
            20                  25                  30

Pro Ala Gly Thr Gly Lys Thr Thr Leu Thr Lys Phe Ile Ile Glu Ala
        35                  40                  45

Leu Ile Ser Thr Gly Glu Thr Gly Ile Ile Leu Ala Ala Pro Thr His
    50                  55                  60

Ala Ala Lys Lys Ile Leu Ser Lys Leu Ser Gly Lys Glu Ala Ser Thr
65                  70                  75                  80

Ile His Ser Ile Leu Lys Ile Asn Pro Val Thr Tyr Glu Glu Asn Val
                85                  90                  95

Leu Phe Glu Gln Lys Glu Val Pro Asp Leu Ala Lys Cys Arg Val Leu
            100                 105                 110

Ile Cys Asp Glu Val Ser Met Tyr Asp Arg Lys Leu Phe Lys Ile Leu
        115                 120                 125

Leu Ser Thr Ile Pro Pro Trp Cys Thr Ile Ile Gly Ile Gly Asp Asn
    130                 135                 140

Lys Gln Ile Arg Pro Val Asp Pro Gly Glu Asn Thr Ala Tyr Ile Ser
145                 150                 155                 160

Pro Phe Phe Thr His Lys Asp Phe Tyr Gln Cys Glu Leu Thr Glu Val
                165                 170                 175

Lys Arg Ser Asn Ala Pro Ile Ile Asp Val Ala Thr Asp Val Arg Asn
            180                 185                 190

Gly Lys Trp Ile Tyr Asp Lys Val Val Asp Gly His Gly Val Arg Gly
        195                 200                 205

Phe Thr Gly Asp Thr Ala Leu Arg Asp Phe Met Val Asn Tyr Phe Ser
    210                 215                 220

Ile Val Lys Ser Leu Asp Asp Leu Phe Glu Asn Arg Val Met Ala Phe
225                 230                 235                 240

Thr Asn Lys Ser Val Asp Lys Leu Asn Ser Ile Ile Arg Lys Lys Ile
                245                 250                 255

Phe Glu Thr Asp Lys Asp Phe Ile Val Gly Glu Ile Ile Val Met Gln
            260                 265                 270

Glu Pro Leu Phe Lys Thr Tyr Lys Ile Asp Gly Lys Pro Val Ser Glu
        275                 280                 285

Ile Ile Phe Asn Asn Gly Gln Leu Val Arg Ile Ile Glu Ala Glu Tyr
    290                 295                 300

Thr Ser Thr Phe Val Lys Ala Arg Gly Val Pro Gly Glu Tyr Leu Ile
305                 310                 315                 320
```

```
Arg His Trp Asp Leu Thr Val Glu Thr Tyr Gly Asp Asp Glu Tyr Tyr
                325                 330                 335

Arg Glu Lys Ile Lys Ile Ile Ser Ser Asp Glu Glu Leu Tyr Lys Phe
            340                 345                 350

Asn Leu Phe Leu Gly Lys Thr Ala Glu Thr Tyr Lys Asn Trp Asn Lys
        355                 360                 365

Gly Gly Lys Ala Pro Trp Ser Asp Phe Trp Asp Ala Lys Ser Gln Phe
    370                 375                 380

Ser Lys Val Lys Ala Leu Pro Ala Ser Thr Phe His Lys Ala Gln Gly
385                 390                 395                 400

Met Ser Val Asp Arg Ala Phe Ile Tyr Thr Pro Cys Ile His Tyr Ala
                405                 410                 415

Asp Val Glu Leu Ala Gln Gln Leu Leu Tyr Val Gly Val Thr Arg Gly
            420                 425                 430

Arg Tyr Asp Val Phe Tyr Val
        435


<210> SEQ ID NO 25
<211> LENGTH: 970
<212> TYPE: PRT
<213> ORGANISM: Artificial Sequence
<220> FEATURE:
<223> OTHER INFORMATION: Trwc Cba

<400> SEQUENCE: 25

Met Leu Ser Val Ala Asn Val Arg Ser Pro Ser Ala Ala Ala Ser Tyr
1               5                   10                  15

Phe Ala Ser Asp Asn Tyr Tyr Ala Ser Ala Asp Ala Asp Arg Ser Gly
            20                  25                  30

Gln Trp Ile Gly Asp Gly Ala Lys Arg Leu Gly Leu Glu Gly Lys Val
        35                  40                  45

Glu Ala Arg Ala Phe Asp Ala Leu Leu Arg Gly Glu Leu Pro Asp Gly
    50                  55                  60

Ser Ser Val Gly Asn Pro Gly Gln Ala His Arg Pro Gly Thr Asp Leu
65                  70                  75                  80

Thr Phe Ser Val Pro Lys Ser Trp Ser Leu Leu Ala Leu Val Gly Lys
                85                  90                  95

Asp Glu Arg Ile Ile Ala Ala Tyr Arg Glu Ala Val Val Glu Ala Leu
            100                 105                 110

His Trp Ala Glu Lys Asn Ala Ala Glu Thr Arg Val Val Glu Lys Gly
        115                 120                 125

Met Val Val Thr Gln Ala Thr Gly Asn Leu Ala Ile Gly Leu Phe Gln
    130                 135                 140

His Asp Thr Asn Arg Asn Gln Glu Pro Asn Leu His Phe His Ala Val
145                 150                 155                 160

Ile Ala Asn Val Thr Gln Gly Lys Asp Gly Lys Trp Arg Thr Leu Lys
                165                 170                 175

Asn Asp Arg Leu Trp Gln Leu Asn Thr Thr Leu Asn Ser Ile Ala Met
            180                 185                 190

Ala Arg Phe Arg Val Ala Val Glu Lys Leu Gly Tyr Glu Pro Gly Pro
        195                 200                 205

Val Leu Lys His Gly Asn Phe Glu Ala Arg Gly Ile Ser Arg Glu Gln
    210                 215                 220

Val Met Ala Phe Ser Thr Arg Arg Lys Glu Val Leu Glu Ala Arg Arg
225                 230                 235                 240
```

-continued

```
Gly Pro Gly Leu Asp Ala Gly Arg Ile Ala Ala Leu Asp Thr Arg Ala
                245                 250                 255

Ser Lys Glu Gly Ile Glu Asp Arg Ala Thr Leu Ser Lys Gln Trp Ser
            260                 265                 270

Glu Ala Ala Gln Ser Ile Gly Leu Asp Leu Lys Pro Leu Val Asp Arg
        275                 280                 285

Ala Arg Thr Lys Ala Leu Gly Gln Gly Met Glu Ala Thr Arg Ile Gly
    290                 295                 300

Ser Leu Val Glu Arg Gly Arg Ala Trp Leu Ser Arg Phe Ala Ala His
305                 310                 315                 320

Val Arg Gly Asp Pro Ala Asp Pro Leu Val Pro Pro Ser Val Leu Lys
                325                 330                 335

Gln Asp Arg Gln Thr Ile Ala Ala Ala Gln Ala Val Ala Ser Ala Val
            340                 345                 350

Arg His Leu Ser Gln Arg Glu Ala Ala Phe Glu Arg Thr Ala Leu Tyr
        355                 360                 365

Lys Ala Ala Leu Asp Phe Gly Leu Pro Thr Thr Ile Ala Asp Val Glu
    370                 375                 380

Lys Arg Thr Arg Ala Leu Val Arg Ser Gly Asp Leu Ile Ala Gly Lys
385                 390                 395                 400

Gly Glu His Lys Gly Trp Leu Ala Ser Arg Asp Ala Val Val Thr Glu
                405                 410                 415

Gln Arg Ile Leu Ser Glu Val Ala Ala Gly Lys Gly Asp Ser Ser Pro
            420                 425                 430

Ala Ile Thr Pro Gln Lys Ala Ala Ala Ser Val Gln Ala Ala Ala Leu
        435                 440                 445

Thr Gly Gln Gly Phe Arg Leu Asn Glu Gly Gln Leu Ala Ala Ala Arg
    450                 455                 460

Leu Ile Leu Ile Ser Lys Asp Arg Thr Ile Ala Val Gln Gly Ile Ala
465                 470                 475                 480

Gly Ala Gly Lys Ser Ser Val Leu Lys Pro Val Ala Glu Val Leu Arg
                485                 490                 495

Asp Glu Gly His Pro Val Ile Gly Leu Ala Ile Gln Asn Thr Leu Val
            500                 505                 510

Gln Met Leu Glu Arg Asp Thr Gly Ile Gly Ser Gln Thr Leu Ala Arg
        515                 520                 525

Phe Leu Gly Gly Trp Asn Lys Leu Leu Asp Asp Pro Gly Asn Val Ala
    530                 535                 540

Leu Arg Ala Glu Ala Gln Ala Ser Leu Lys Asp His Val Leu Val Leu
545                 550                 555                 560

Asp Glu Ala Ser Met Val Ser Asn Glu Asp Lys Glu Lys Leu Val Arg
                565                 570                 575

Leu Ala Asn Leu Ala Gly Val His Arg Leu Val Leu Ile Gly Asp Arg
            580                 585                 590

Lys Gln Leu Gly Ala Val Asp Ala Gly Lys Pro Phe Ala Leu Leu Gln
        595                 600                 605

Arg Ala Gly Ile Ala Arg Ala Glu Met Ala Thr Asn Leu Arg Ala Arg
    610                 615                 620

Asp Pro Val Val Arg Glu Ala Gln Ala Ala Ala Gln Ala Gly Asp Val
625                 630                 635                 640

Arg Lys Ala Leu Arg His Leu Lys Ser His Thr Val Glu Ala Arg Gly
                645                 650                 655

Asp Gly Ala Gln Val Ala Ala Glu Thr Trp Leu Ala Leu Asp Lys Glu
```

660 665 670

Thr Arg Ala Arg Thr Ser Ile Tyr Ala Ser Gly Arg Ala Ile Arg Ser
675 680 685

Ala Val Asn Ala Ala Val Gln Gln Gly Leu Leu Ala Ser Arg Glu Ile
690 695 700

Gly Pro Ala Lys Met Lys Leu Glu Val Leu Asp Arg Val Asn Thr Thr
705 710 715 720

Arg Glu Glu Leu Arg His Leu Pro Ala Tyr Arg Ala Gly Arg Val Leu
725 730 735

Glu Val Ser Arg Lys Gln Gln Ala Leu Gly Leu Phe Ile Gly Glu Tyr
740 745 750

Arg Val Ile Gly Gln Asp Arg Lys Gly Lys Leu Val Glu Val Glu Asp
755 760 765

Lys Arg Gly Lys Arg Phe Arg Phe Asp Pro Ala Arg Ile Arg Ala Gly
770 775 780

Lys Gly Asp Asp Asn Leu Thr Leu Leu Glu Pro Arg Lys Leu Glu Ile
785 790 795 800

His Glu Gly Asp Arg Ile Arg Trp Thr Arg Asn Asp His Arg Arg Gly
805 810 815

Leu Phe Asn Ala Asp Gln Ala Arg Val Val Glu Ile Ala Asn Gly Lys
820 825 830

Val Thr Phe Glu Thr Ser Lys Gly Asp Leu Val Glu Leu Lys Lys Asp
835 840 845

Asp Pro Met Leu Lys Arg Ile Asp Leu Ala Tyr Ala Leu Asn Val His
850 855 860

Met Ala Gln Gly Leu Thr Ser Asp Arg Gly Ile Ala Val Met Asp Ser
865 870 875 880

Arg Glu Arg Asn Leu Ser Asn Gln Lys Thr Phe Leu Val Thr Val Thr
885 890 895

Arg Leu Arg Asp His Leu Thr Leu Val Val Asp Ser Ala Asp Lys Leu
900 905 910

Gly Ala Ala Val Ala Arg Asn Lys Gly Glu Lys Ala Ser Ala Ile Glu
915 920 925

Val Thr Gly Ser Val Lys Pro Thr Ala Thr Lys Gly Ser Gly Val Asp
930 935 940

Gln Pro Lys Ser Val Glu Ala Asn Lys Ala Glu Lys Glu Leu Thr Arg
945 950 955 960

Ser Lys Ser Lys Thr Leu Asp Phe Gly Ile
965 970

<210> SEQ ID NO 26
<211> LENGTH: 786
<212> TYPE: DNA
<213> ORGANISM: Artificial Sequence
<220> FEATURE:
<223> OTHER INFORMATION: Wild-type CsgG monomer from Escherichia coli
Str. K-12 substr. MC4100

<400> SEQUENCE: 26
tgtctgaccg caccgccgaa agaagcggca cgtccgaccc tgatgccgcg tgcacagtct 60
tataaagatc tgacccatct gccggctccg acgggcaaaa tttttgttag cgtctataac 120
atccaggacg aaaccggtca atttaaaccg tacccggcga gtaatttctc cacggccgtt 180
ccgcagagtg caaccgctat gctggtcacg gcactgaaag attcccgttg gttcattccg 240
ctggaacgcc agggcctgca aaacctgctg aatgaacgta aaattatccg cgcagctcag 300

-continued

```
gaaaacggta ccgtggccat taacaatcgt attccgctgc aaagcctgac cgccgcaaac    360

atcatggttg aaggctctat catcggttac gaatcaaacg tcaaatcggg cggtgtgggc    420

gcacgttatt ttggcattgg tgctgatacc cagtaccaac tggaccagat cgcagttaac    480

ctgcgcgtgg ttaatgtcag caccggcgaa attctgagct ctgtgaatac cagcaaaacg    540

atcctgtctt acgaagtgca ggctggtgtt tttcgtttca ttgattatca acgcctgctg    600

gaaggcgaag tcggttacac ctcaaacgaa ccggtgatgc tgtgtctgat gtcggcgatt    660

gaaacgggtg ttattttcct gatcaatgat ggcatcgacc gtggtctgtg ggatctgcag    720

aacaaagccg aacgtcaaaa tgacattctg gtgaaatacc gccacatgag tgttccgccg    780

gaatcc                                                               786
```

<210> SEQ ID NO 27
<211> LENGTH: 262
<212> TYPE: PRT
<213> ORGANISM: Artificial Sequence
<220> FEATURE:
<223> OTHER INFORMATION: Mature form of the wild-type CsgG monomer from Escherichia coli Str. K-12 substr. MC4100

<400> SEQUENCE: 27

```
Cys Leu Thr Ala Pro Pro Lys Glu Ala Ala Arg Pro Thr Leu Met Pro
1               5                   10                  15

Arg Ala Gln Ser Tyr Lys Asp Leu Thr His Leu Pro Ala Pro Thr Gly
            20                  25                  30

Lys Ile Phe Val Ser Val Tyr Asn Ile Gln Asp Glu Thr Gly Gln Phe
        35                  40                  45

Lys Pro Tyr Pro Ala Ser Asn Phe Ser Thr Ala Val Pro Gln Ser Ala
    50                  55                  60

Thr Ala Met Leu Val Thr Ala Leu Lys Asp Ser Arg Trp Phe Ile Pro
65                  70                  75                  80

Leu Glu Arg Gln Gly Leu Gln Asn Leu Leu Asn Glu Arg Lys Ile Ile
                85                  90                  95

Arg Ala Ala Gln Glu Asn Gly Thr Val Ala Ile Asn Asn Arg Ile Pro
            100                 105                 110

Leu Gln Ser Leu Thr Ala Ala Asn Ile Met Val Glu Gly Ser Ile Ile
        115                 120                 125

Gly Tyr Glu Ser Asn Val Lys Ser Gly Gly Val Gly Ala Arg Tyr Phe
    130                 135                 140

Gly Ile Gly Ala Asp Thr Gln Tyr Gln Leu Asp Gln Ile Ala Val Asn
145                 150                 155                 160

Leu Arg Val Val Asn Val Ser Thr Gly Glu Ile Leu Ser Ser Val Asn
                165                 170                 175

Thr Ser Lys Thr Ile Leu Ser Tyr Glu Val Gln Ala Gly Val Phe Arg
            180                 185                 190

Phe Ile Asp Tyr Gln Arg Leu Leu Glu Gly Glu Val Gly Tyr Thr Ser
        195                 200                 205

Asn Glu Pro Val Met Leu Cys Leu Met Ser Ala Ile Glu Thr Gly Val
    210                 215                 220

Ile Phe Leu Ile Asn Asp Gly Ile Asp Arg Gly Leu Trp Asp Leu Gln
225                 230                 235                 240

Asn Lys Ala Glu Arg Gln Asn Asp Ile Leu Val Lys Tyr Arg His Met
                245                 250                 255

Ser Val Pro Pro Glu Ser
```

260

<210> SEQ ID NO 28
<211> LENGTH: 35
<212> TYPE: DNA
<213> ORGANISM: Artificial Sequence
<220> FEATURE:
<223> OTHER INFORMATION: Partial sequence of leader strand

<400> SEQUENCE: 28
ggcgtctgct tgggtgttta accttttttt ttttt 35

<210> SEQ ID NO 29
<211> LENGTH: 28
<212> TYPE: DNA
<213> ORGANISM: Artificial Sequence
<220> FEATURE:
<223> OTHER INFORMATION: Partial sequence of leader strand

<400> SEQUENCE: 29
ggttgtttct gttggtgctg atattgct 28

<210> SEQ ID NO 30
<211> LENGTH: 54
<212> TYPE: DNA
<213> ORGANISM: Artificial Sequence
<220> FEATURE:
<223> OTHER INFORMATION: Partial sequence of bottom strand with 3' hairpin

<400> SEQUENCE: 30
gcaatatcag caccaacaga aacaaccgcc atcagattgt gtttgttagt cgct 54

<210> SEQ ID NO 31
<211> LENGTH: 15
<212> TYPE: DNA
<213> ORGANISM: Artificial Sequence
<220> FEATURE:
<223> OTHER INFORMATION: Partial sequence of bottom strand with 3' hairpin

<400> SEQUENCE: 31
gaggcgagcg gtcaa 15

<210> SEQ ID NO 32
<211> LENGTH: 25
<212> TYPE: DNA
<213> ORGANISM: Artificial Sequence
<220> FEATURE:
<223> OTHER INFORMATION: Partial sequence of bottom strand containing a 3' hairpin

<400> SEQUENCE: 32
agcgactaac aaacacaatc tgatg 25

<210> SEQ ID NO 33
<211> LENGTH: 20
<212> TYPE: DNA
<213> ORGANISM: Artificial Sequence
<220> FEATURE:
<223> OTHER INFORMATION: Sequence of blocker strand

<400> SEQUENCE: 33
aacacccaag cagacgcctt 20

<210> SEQ ID NO 34

```
<211> LENGTH: 48
<212> TYPE: DNA
<213> ORGANISM: Artificial Sequence
<220> FEATURE:
<223> OTHER INFORMATION: Partial sequence of HP-adapter

<400> SEQUENCE: 34

cgttctgttt atgtttcttg gacactgatt gacacggttt agtagaac                48


<210> SEQ ID NO 35
<211> LENGTH: 28
<212> TYPE: DNA
<213> ORGANISM: Artificial Sequence
<220> FEATURE:
<223> OTHER INFORMATION: Partial sequence of HP-adapter

<400> SEQUENCE: 35

tttttttttt tttttttttt tttttttt                                      28


<210> SEQ ID NO 36
<211> LENGTH: 21
<212> TYPE: DNA
<213> ORGANISM: Artificial Sequence
<220> FEATURE:
<223> OTHER INFORMATION: Partial sequence of HP-adapter

<400> SEQUENCE: 36

caagaaacat aaacagaacg t                                             21


<210> SEQ ID NO 37
<211> LENGTH: 15
<212> TYPE: DNA
<213> ORGANISM: Artificial Sequence
<220> FEATURE:
<223> OTHER INFORMATION: Tether

<400> SEQUENCE: 37

ttgaccgctc gcctc                                                    15


<210> SEQ ID NO 38
<211> LENGTH: 32
<212> TYPE: DNA
<213> ORGANISM: Artificial Sequence
<220> FEATURE:
<223> OTHER INFORMATION: Sequence of hairpin tether

<400> SEQUENCE: 38

ttgttctact aaaccgtgtc aatcagtgtc tt                                 32


<210> SEQ ID NO 39
<211> LENGTH: 10
<212> TYPE: DNA
<213> ORGANISM: Artificial Sequence
<220> FEATURE:
<223> OTHER INFORMATION: Partial sequence of leader strand

<400> SEQUENCE: 39

ggttgtttct                                                          10


<210> SEQ ID NO 40
<211> LENGTH: 41
<212> TYPE: DNA
<213> ORGANISM: Artificial Sequence
<220> FEATURE:
<223> OTHER INFORMATION: Blocker strand containing a tether
      hybridisation site
```

-continued

```
<400> SEQUENCE: 40

ggttaaacac ccaagcagac gcctttgagg cgagcggtca a                     41


<210> SEQ ID NO 41
<211> LENGTH: 52
<212> TYPE: DNA
<213> ORGANISM: Artificial Sequence
<220> FEATURE:
<223> OTHER INFORMATION: Partial sequence of bottom strand containing a
      3' hairpin

<400> SEQUENCE: 41

gcaatatcag caccaacaga aacaacccat cagattgtgt ttgttagtcg ct         52


<210> SEQ ID NO 42
<211> LENGTH: 53
<212> TYPE: DNA
<213> ORGANISM: Artificial Sequence
<220> FEATURE:
<223> OTHER INFORMATION: Blocker strand containing a tether
      hybridisation site and a polyA 5' extension

<400> SEQUENCE: 42

aaaaaaaaaa aaggttaaac acccaagcag acgcctttga ggcgagcggt caa        53


<210> SEQ ID NO 43

<400> SEQUENCE: 43

000
```